US010008679B2

(12) United States Patent
Chen et al.

(10) Patent No.: US 10,008,679 B2
(45) Date of Patent: *Jun. 26, 2018

(54) ORGANIC ELECTROLUMINESCENT MATERIALS AND DEVICES

(71) Applicant: Universal Display Corporation, Ewing, NJ (US)

(72) Inventors: Hsiao-Fan Chen, Ewing, NJ (US); Scott Beers, Ewing, NJ (US); Geza Szigethy, Ewing, NJ (US); Jason Brooks, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 368 days.

This patent is subject to a terminal disclaimer.

(21) Appl. No.: 14/672,034

(22) Filed: Mar. 27, 2015

(65) Prior Publication Data

US 2015/0295190 A1  Oct. 15, 2015

Related U.S. Application Data

(60) Provisional application No. 61/979,103, filed on Apr. 14, 2014, provisional application No. 61/991,720, filed on May 12, 2014.

(51) Int. Cl.
*C07F 15/00* (2006.01)
*H01L 51/00* (2006.01)
*C09K 11/06* (2006.01)
*C09B 57/00* (2006.01)
*C09B 57/10* (2006.01)
*H01L 51/50* (2006.01)

(52) U.S. Cl.
CPC ...... H01L 51/0085 (2013.01); C07F 15/0033 (2013.01); C07F 15/0086 (2013.01); C09B 57/00 (2013.01); C09B 57/10 (2013.01); C09K 11/06 (2013.01); *C09K 2211/1007* (2013.01); *C09K 2211/1011* (2013.01); *C09K 2211/1096* (2013.01); *H01L 51/5016* (2013.01)

(58) Field of Classification Search
CPC .. C07F 15/0033; C07F 15/0086; C09K 11/06; H01L 51/0085; H01L 51/0087; H01L 51/0094
USPC ...................................... 428/411.1, 490, 690
See application file for complete search history.

(56) References Cited

U.S. PATENT DOCUMENTS

| 4,769,292 | A | 9/1988 | Tang et al. |
|---|---|---|---|
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 7,968,146 | B2 | 6/2011 | Wanger et al. |
| 8,142,909 | B2 * | 3/2012 | Beers ............... C07F 15/0033 252/301.16 |
| 8,383,249 | B2 * | 2/2013 | Walters ............... C07F 15/002 257/40 |
| 9,548,462 | B2 * | 1/2017 | Knowles ........... C07F 15/0033 |
| 9,722,193 | B2 * | 8/2017 | Knowles ........... H01L 51/0085 |
| 9,728,731 | B2 * | 8/2017 | La .................. C07D 401/14 |
| 9,847,498 | B2 * | 12/2017 | Brooks .............. H01L 51/0085 |
| 9,882,151 | B2 * | 1/2018 | Kwong .............. H01L 51/009 |
| 2002/0034656 | A1 | 3/2002 | Thompson et al. |
| 2002/0134984 | A1 | 9/2002 | Igarashi |

(Continued)

FOREIGN PATENT DOCUMENTS

| CN | 101827834 | 9/2010 |
|---|---|---|
| EP | 650955 | 5/1995 |

(Continued)

OTHER PUBLICATIONS

Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 3, 4-6 (1999).
U.S. Appl. No. 13/193,221, filed Jul. 28, 2011.
U.S. Appl. No. 13/296,806, filed Nov. 15, 2011.
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

(Continued)

*Primary Examiner* — Douglas J McGinty
(74) *Attorney, Agent, or Firm* — Riverside Law LLP

(57) ABSTRACT

Phosphorescent complexes are designed with intramolecular H-bonding properties to prevent deprotonation of neighboring molecules.

17 Claims, 12 Drawing Sheets

(56) References Cited

U.S. PATENT DOCUMENTS

| | | |
|---|---|---|
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1* | 8/2007 | Knowles ............. C07F 15/0033 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0223634 A1* | 9/2012 | Xia ......................... C09K 11/06 313/504 |
| 2013/0026452 A1 | 1/2013 | Kottas et al. |
| 2013/0119354 A1 | 5/2013 | Ma et al. |
| 2013/0181190 A1 | 7/2013 | Ma et al. |
| 2015/0295189 A1* | 10/2015 | Brooks ............... H01L 51/0085 257/40 |
| 2015/0295190 A1* | 10/2015 | Chen .................. H01L 51/0085 257/40 |
| 2017/0012224 A1* | 1/2017 | Li ........................... C09K 11/06 |
| 2017/0040538 A1* | 2/2017 | Matsumoto ............ C09K 11/06 |
| 2017/0141325 A1* | 5/2017 | Lee ..................... H01L 51/0067 |
| 2017/0162802 A1* | 6/2017 | Weaver ............... H01L 51/0085 |
| 2017/0317295 A1* | 11/2017 | No ....................... H01L 51/0072 |
| 2018/0040829 A1* | 2/2018 | Lee ..................... H01L 51/0071 |

FOREIGN PATENT DOCUMENTS

| | | |
|---|---|---|
| EP | 1238981 | 9/2002 |
| EP | 1725079 | 11/2006 |
| EP | 2034538 | 3/2009 |
| EP | 2551274 | 1/2013 |
| EP | 2565249 | 3/2013 |
| EP | 2574613 | 4/2013 |
| JP | 200511610 | 1/2005 |
| JP | 2007123392 | 5/2007 |
| JP | 2007254297 | 10/2007 |
| JP | 2008074939 | 4/2008 |
| JP | 2010118591 | 5/2010 |
| JP | 2010/135467 | 6/2010 |
| JP | 2013191804 | 9/2013 |
| WO | 2001/039234 | 5/2001 |
| WO | 2002/002714 | 1/2002 |
| WO | 2002/15645 | 2/2002 |
| WO | 2003/040257 | 5/2003 |
| WO | 2003/060956 | 7/2003 |
| WO | 2004/093207 | 10/2004 |
| WO | 2004/107822 | 12/2004 |
| WO | 2004/111066 | 12/2004 |
| WO | 2005/014551 | 2/2005 |
| WO | 2005/019373 | 3/2005 |
| WO | 2005/030900 | 4/2005 |
| WO | 2005/089025 | 9/2005 |
| WO | 2005/123873 | 12/2005 |
| WO | 2006/009024 | 1/2006 |
| WO | 2006/056418 | 6/2006 |
| WO | 2006/072002 | 7/2006 |
| WO | 2006/082742 | 8/2006 |
| WO | 2006/098120 | 9/2006 |
| WO | 2006/100298 | 9/2006 |
| WO | 2006/103874 | 10/2006 |
| WO | 2006/114966 | 11/2006 |
| WO | 2006/132173 | 12/2006 |
| WO | 2007/002683 | 1/2007 |
| WO | 2007/004380 | 1/2007 |
| WO | 2007/063754 | 6/2007 |
| WO | 2007/063796 | 6/2007 |
| WO | 2008/044723 | 4/2008 |
| WO | 2008057394 | 5/2008 |
| WO | 2008/101842 | 8/2008 |
| WO | 2008/132085 | 11/2008 |
| WO | 2008/156879 | 12/2008 |
| WO | 2009/000673 | 12/2008 |
| WO | 2008156879 | 12/2008 |
| WO | 2009/003898 | 1/2009 |
| WO | 2009/008311 | 1/2009 |
| WO | 2009/018009 | 2/2009 |
| WO | 2009/050290 | 4/2009 |
| WO | 2008/056746 | 5/2009 |
| WO | 2009/021126 | 5/2009 |
| WO | 2009/062578 | 5/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 2009/100991 | 8/2009 |
| WO | 2010011390 | 1/2010 |
| WO | 2010/111175 | 9/2010 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru∥ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

MA, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

(56) References Cited

OTHER PUBLICATIONS

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing N N^C^N- C N^C^N- N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on p-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

U.S. Appl. No. 14/616,438, Szigethy et al., filed Feb. 6, 2015.

Elangannan Arunan et al, "Definition of the hydrogen bond (IUPAC Recommendations 2011)" Pure and Applied Chemistry, vol. 83, No. 8, Jan. 2011; ISSN: 0033-4545, DOI: 10.1351/PAC-REC-10-01-02.

* cited by examiner

ORGANIC ELECTROLUMINESCENT MATERIALS AND DEVICES

CROSS-REFERENCE TO RELATED APPLICATIONS

This application claims priority from U.S. Provisional Patent Application Ser. Nos. 61/979,103, filed Apr. 14, 2014, and 61/991,720, filed May 12, 2014, the entire contents of each of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

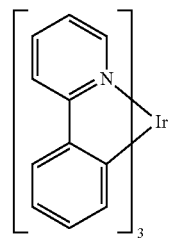

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

A proposed mechanism for the decomposition of complexes that contain an uncoordinated nitrogen is an event where the uncoordinated nitrogen acts as a base by deprotonating a neighboring molecule, leading to non-emissive and potentially ionic reaction products. This event may happen in the excited state or in the presence of charged states found in the device environment. However, some methods used to minimize protonation of the uncoordinated nitrogen may negatively affect other properties of the complex, such as by decreasing photoluminescent quantum yield (PLQY). There is a need in the art for novel compounds that are not susceptible to protonation of the uncoordinated nitrogen while maintaining desirable physical properties. The present invention addresses this unmet need.

SUMMARY OF THE INVENTION

According to an embodiment, a compound is provided comprising a ligand L selected from the group A consisting of:

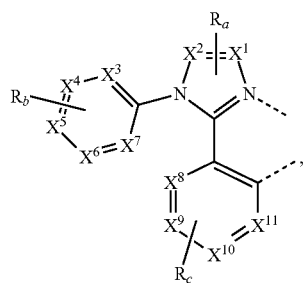

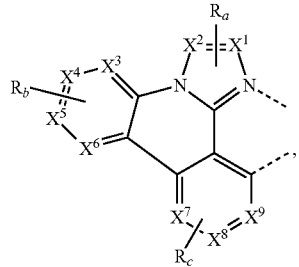

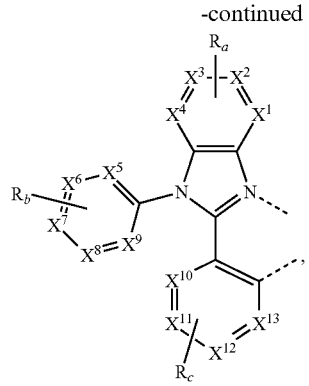

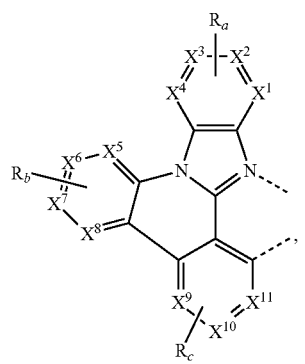

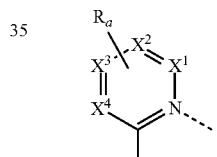

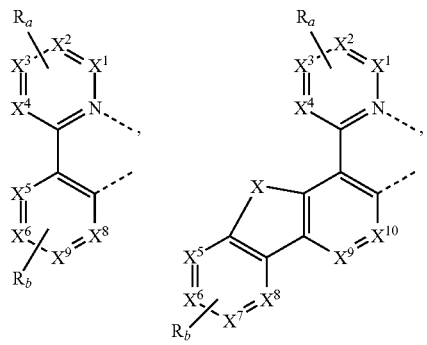

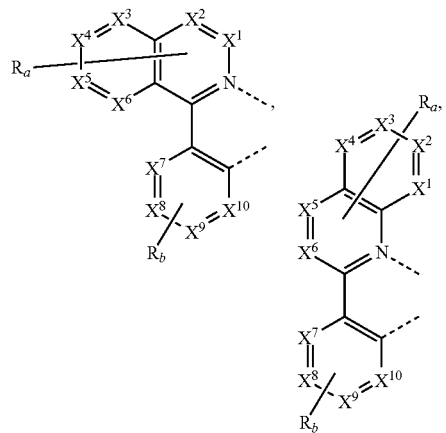

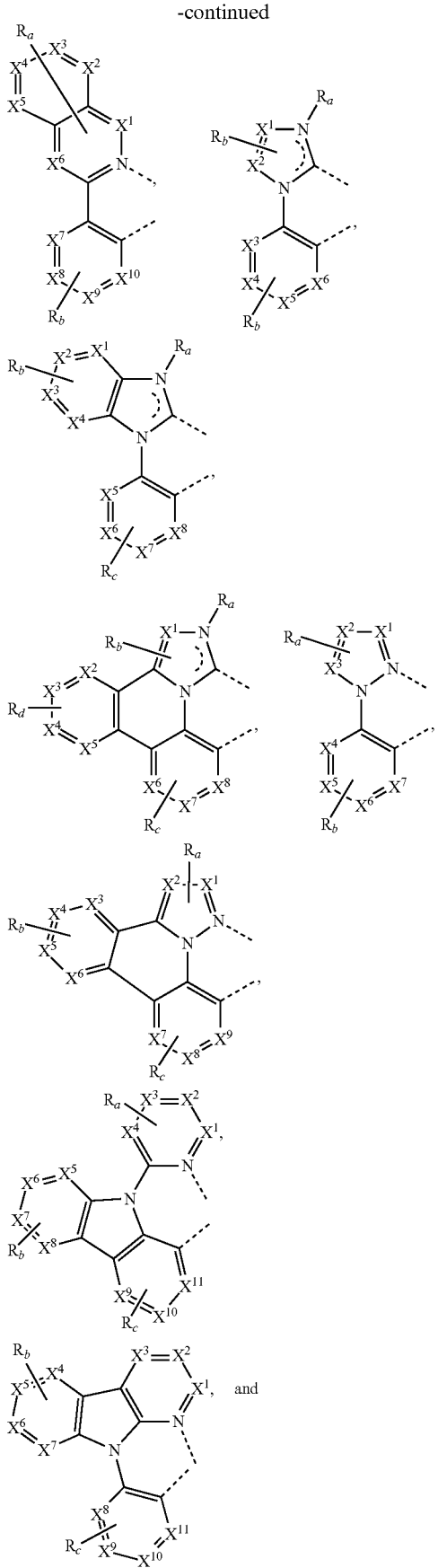

wherein each $X^1$ to $X^{13}$ are independently selected from the group consisting of carbon and nitrogen;

wherein X is selected from the group consisting of BR, NR, PR, O, S, Se, C=O, S=O, $SO_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound comprises at least one intramolecular hydrogen bonding interaction as shown in the scheme:

$$Z^1\text{—H---}Z^2, \qquad \text{scheme 1;}$$

wherein $Z^1$ is selected from the group consisting of carbon, silicon, nitrogen, and oxygen;

wherein $Z^2$ is selected from the group consisting of nitrogen, oxygen, and fluorine; and wherein in scheme 1, the proton NMR chemical shift of H is shifted downfield by at least 1.3 ppm compared to the compound when $Z^2$ is carbon.

In one embodiment, in scheme 1, the proton NMR chemical shift of H is shifted downfield by at least 1.4 ppm compared to the compound when $Z^2$ is carbon. In another embodiment, the compound has an emission with the first peak wavelength at the high energy end smaller at room temperature than that at 77K. In another embodiment, $Z^1$ is carbon, and $Z^2$ is nitrogen. In another embodiment, $Z^1$ is carbon of alkyl, and $Z^2$ is nitrogen of pyridine. In another embodiment, M is selected from the group consisting of Ir, Rh, Re, Ru, Os, Pt, Au, and Cu. In another embodiment, M is Ir or Pt. In another embodiment, the compound is homoleptic. In another embodiment, the compound is heteroleptic. In another embodiment, $Z^2$ is one of $X^1$ to $X^{13}$, and is nitrogen. In another embodiment, $Z^1$ is at least 4 covalent bonds away from $Z^2$. In another embodiment, $Z^1$ is at least 5 covalent bonds away from $Z^2$. In another embodiment, X is O.

In one embodiment, the compound has a formula of Ir(L)$_n$(L')$_{3-n}$;

wherein L' is selected from group A; and wherein n is 1, 2, or 3.

In one embodiment, n is 3. In another embodiment, L' is different from L.

In one embodiment, the compound has a formula of Pt(L)$_m$(L')$_{2-m}$;

wherein L' is selected from group A; and wherein m is 1, or 2.

In one embodiment, m is 1, and L and L' are connected to form a tetradentate ligand. In another embodiment, m is 1; and L and L' are connected at two places to form a macrocyclic tetradentate ligand.

In one embodiment, the ligand L is selected from the group consisting of:

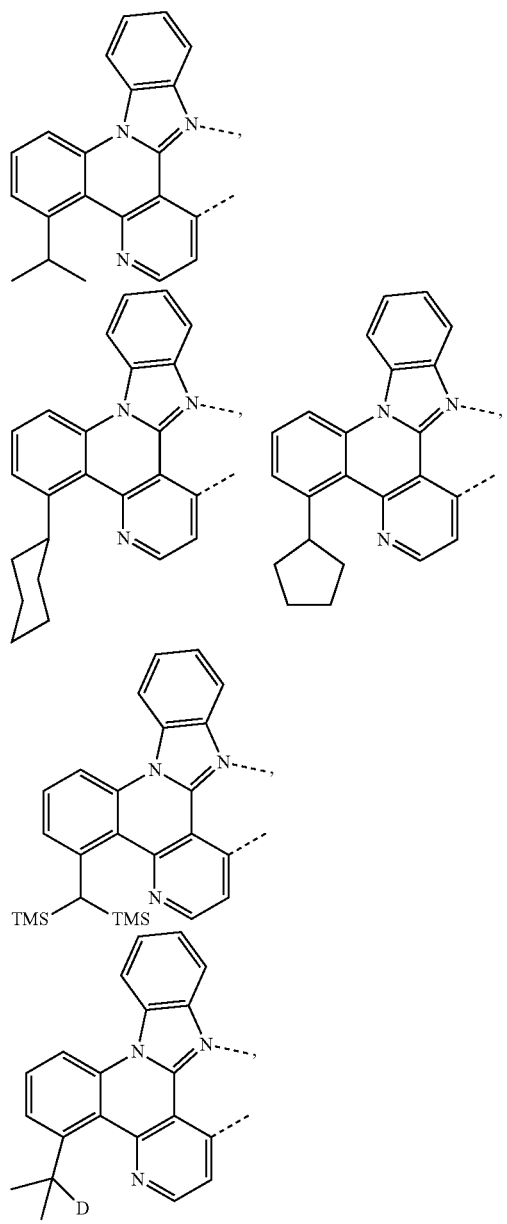

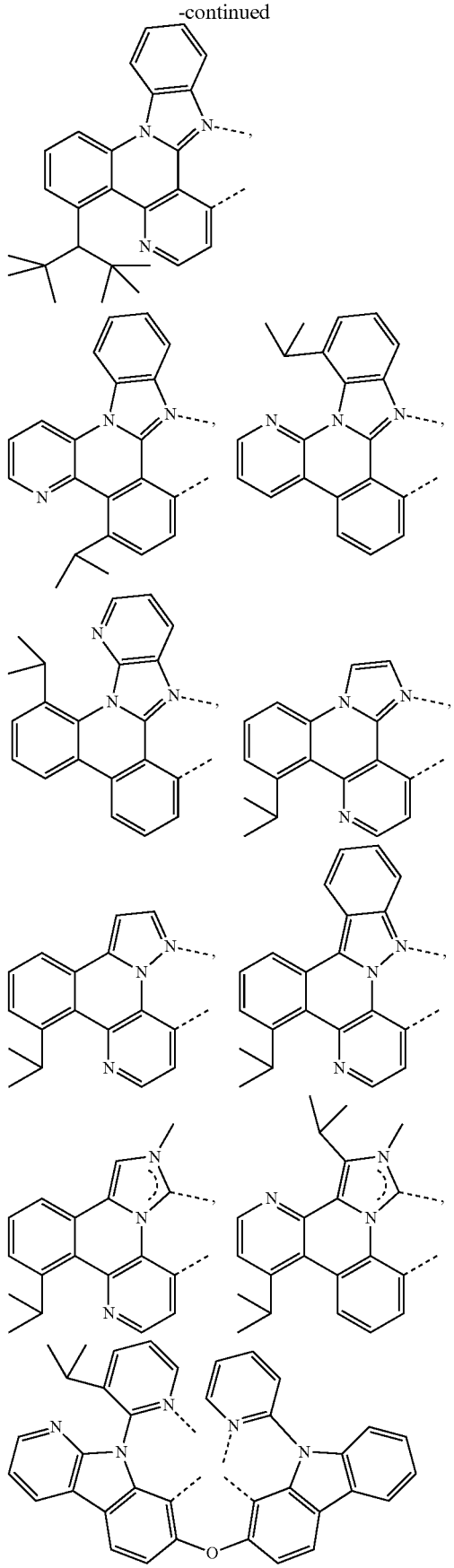

-continued

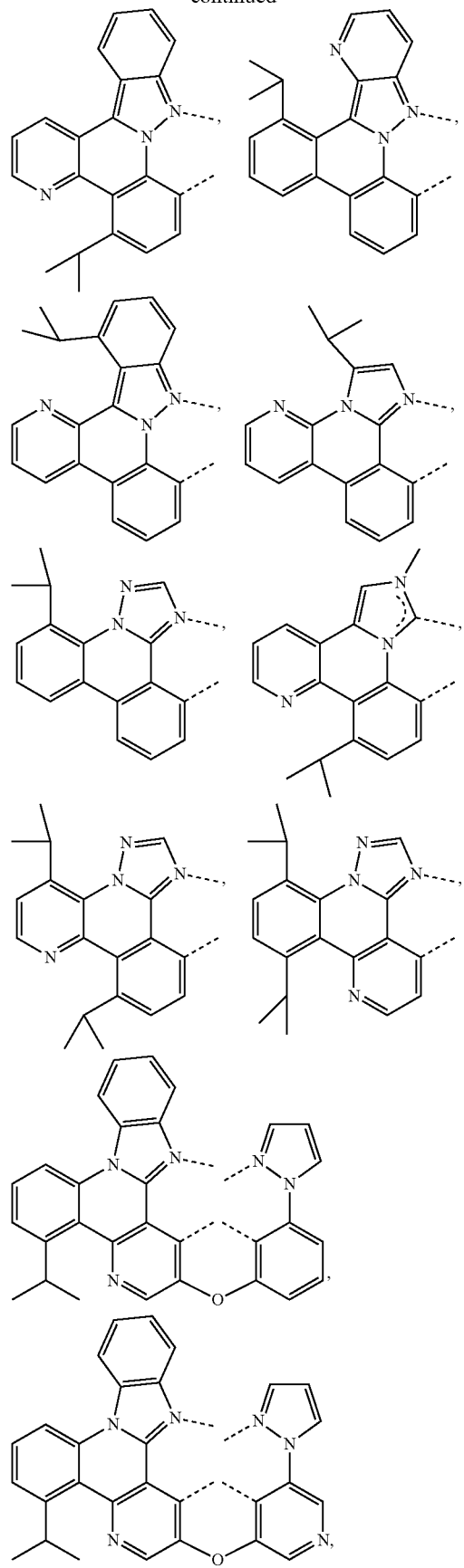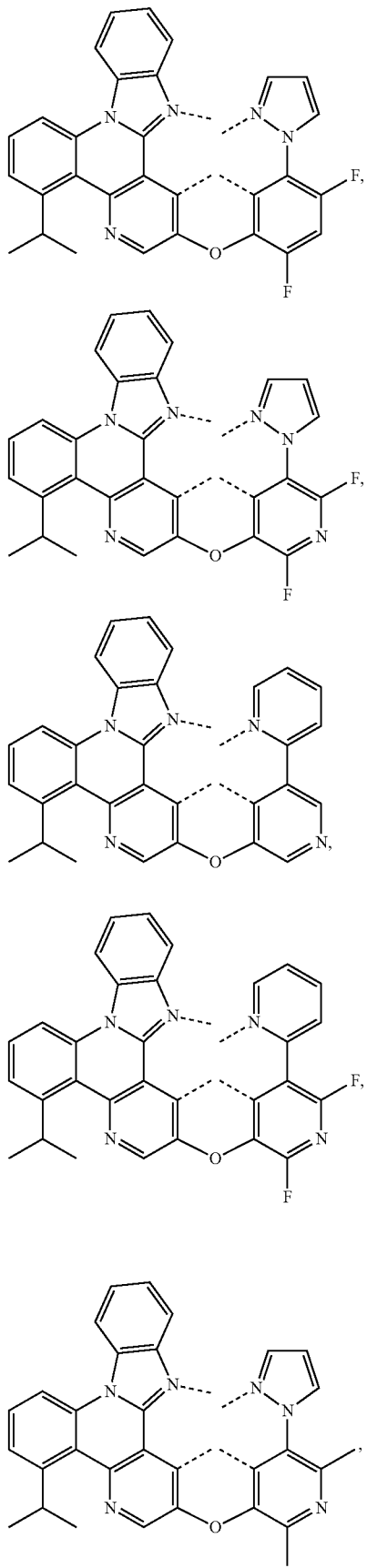

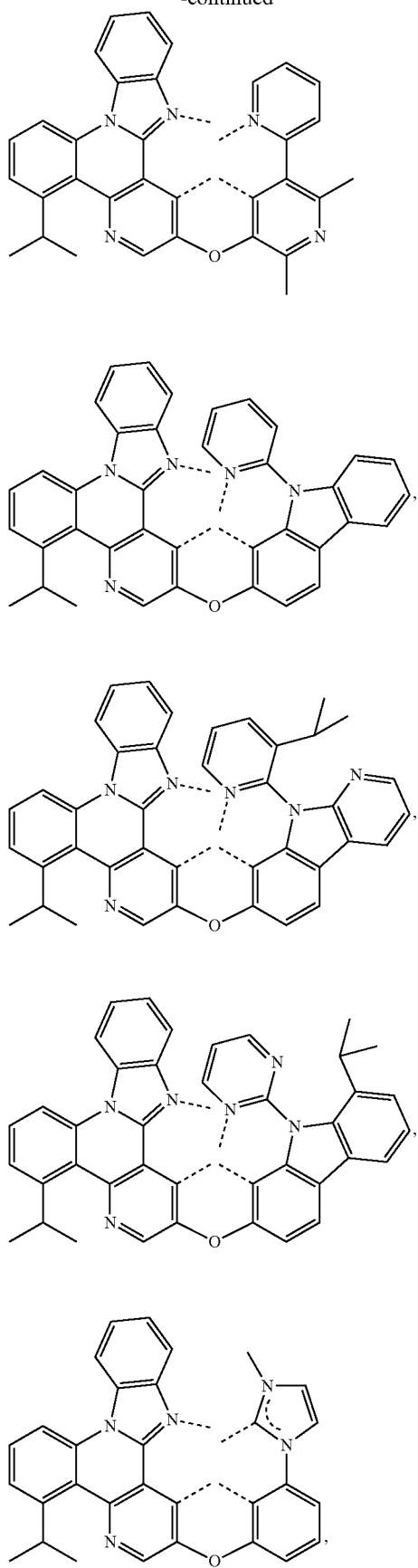
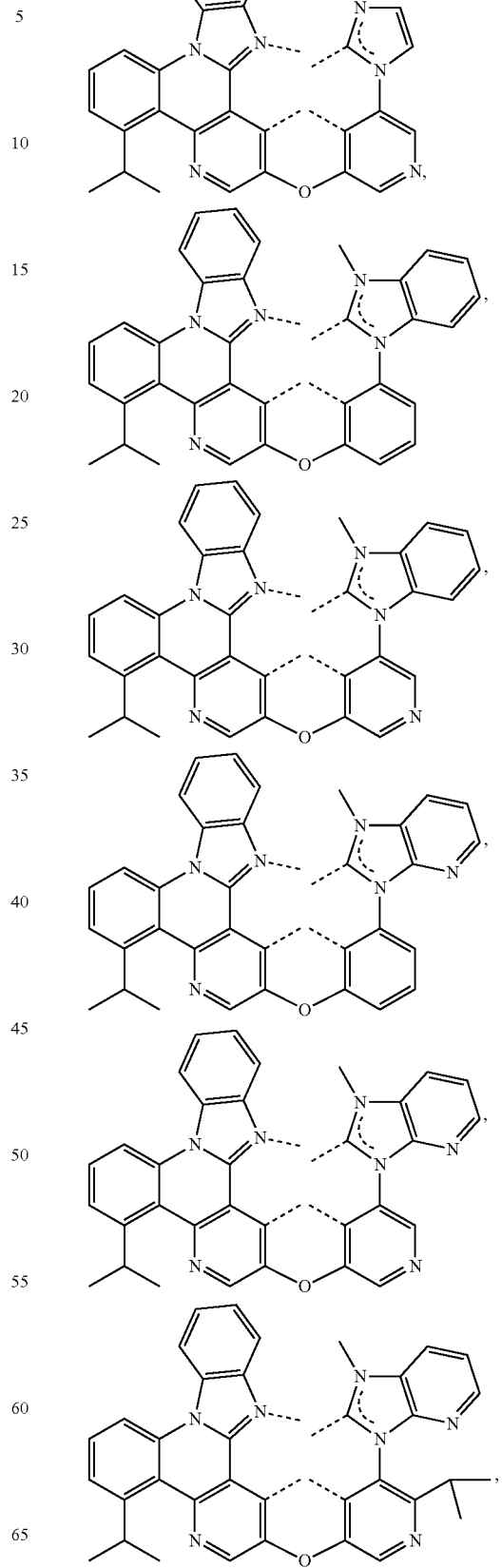

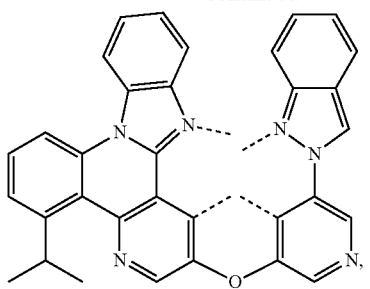
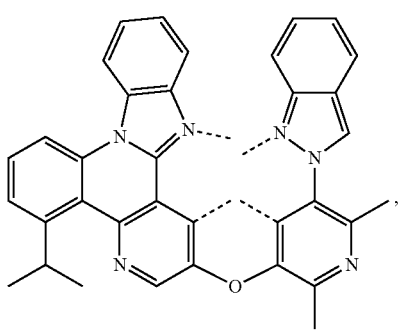
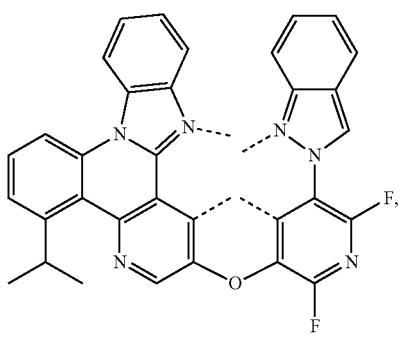
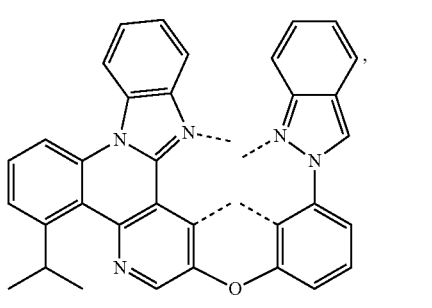
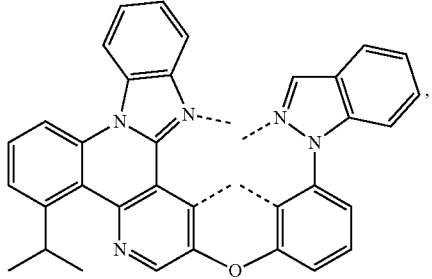
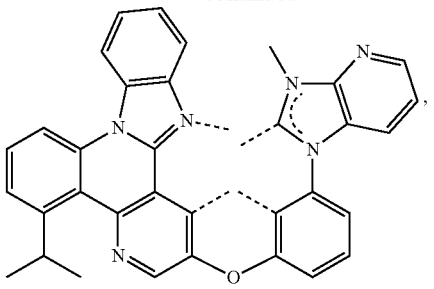
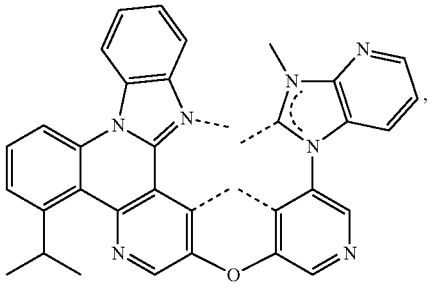
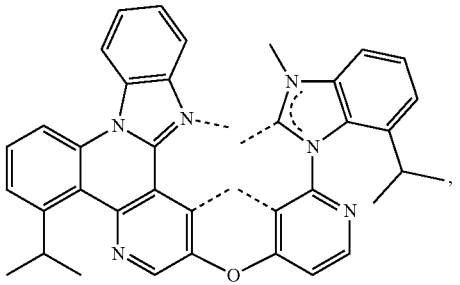
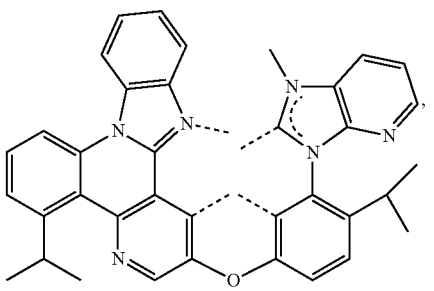
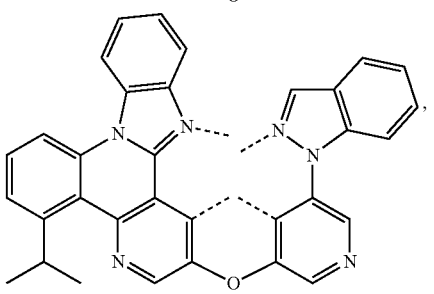
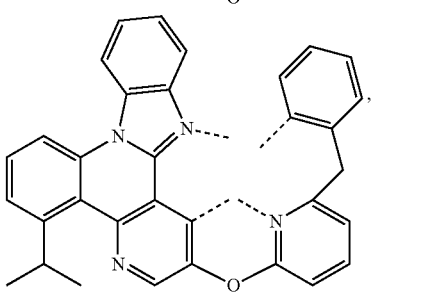

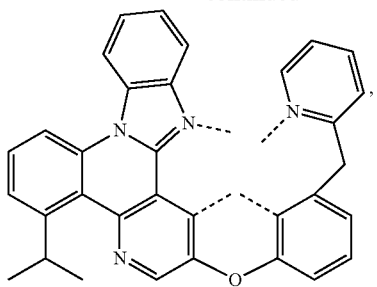
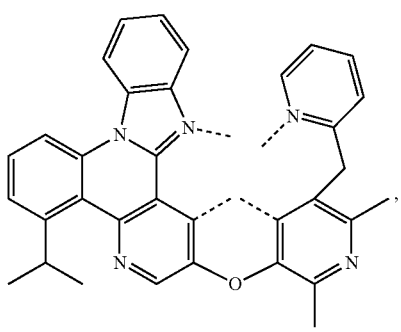
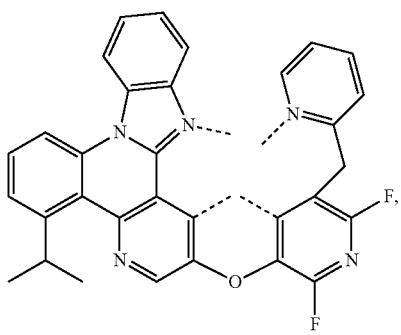
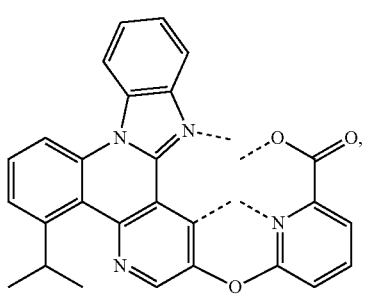
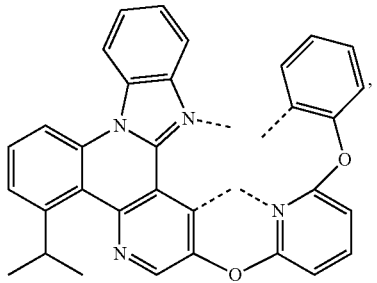
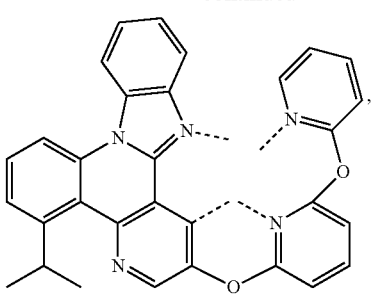
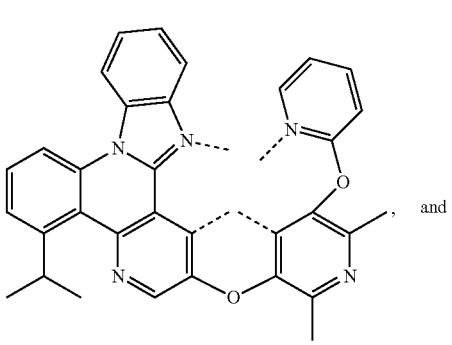, and
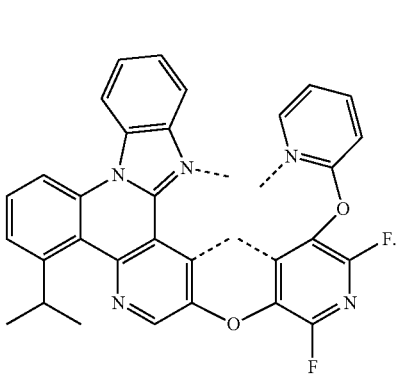
In one embodiment, the compound is selected from the group consisting of:
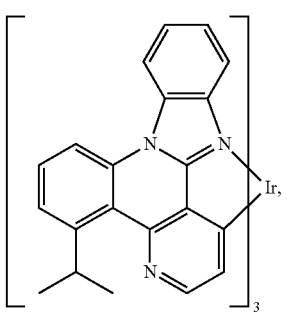

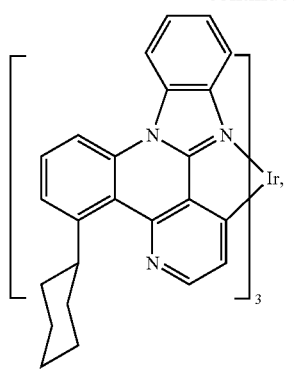
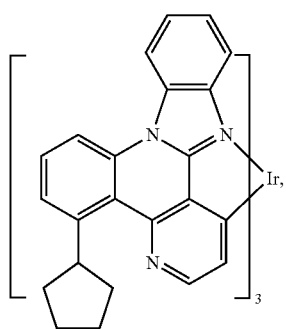
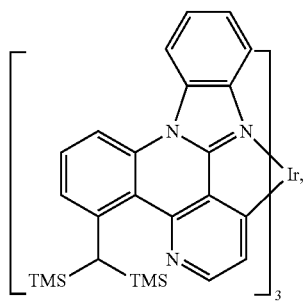
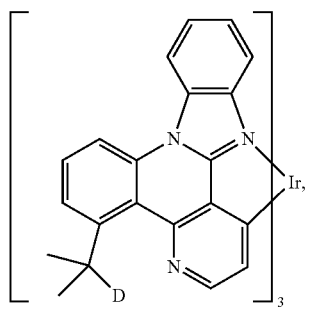
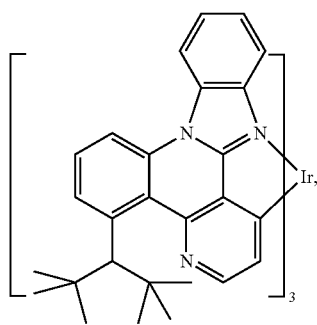
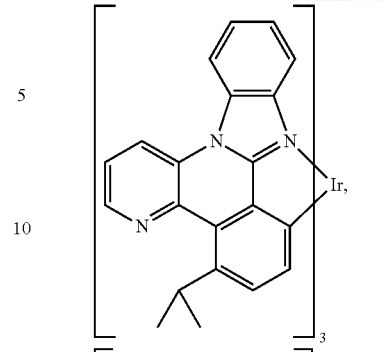
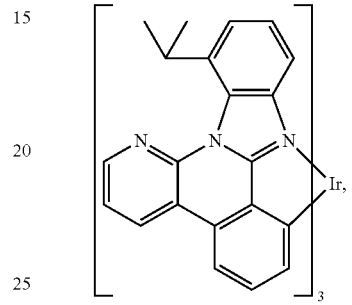
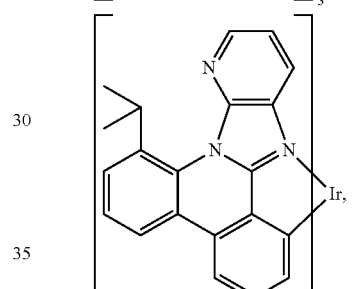
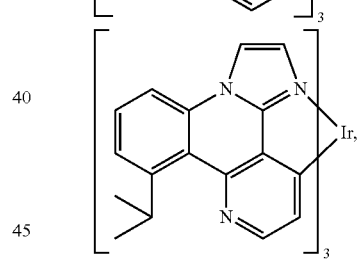
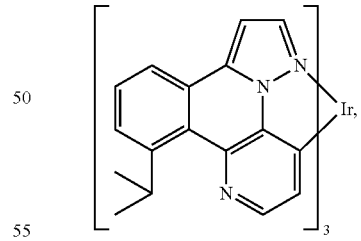
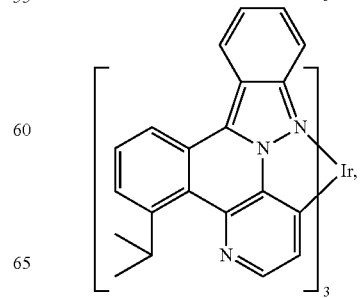

-continued
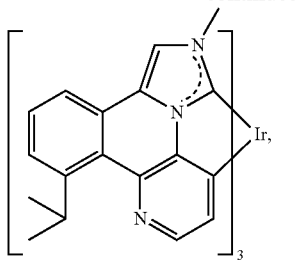
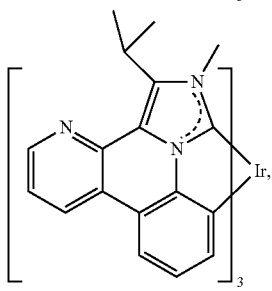
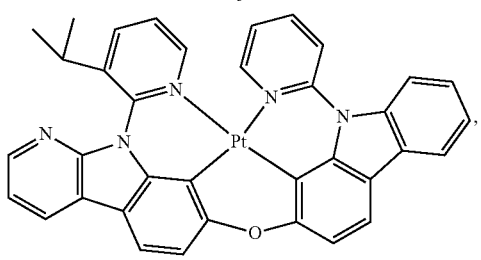
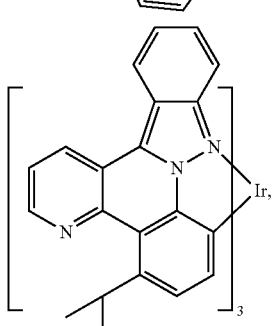
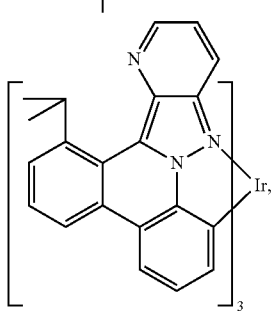
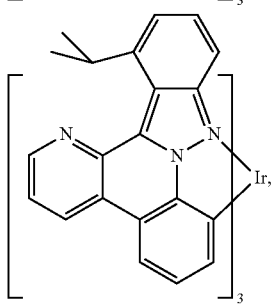
-continued
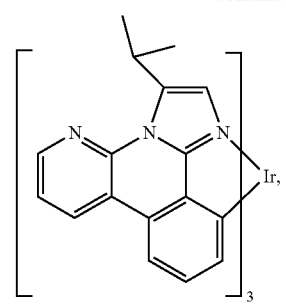
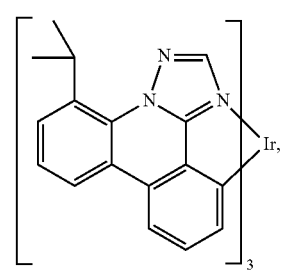
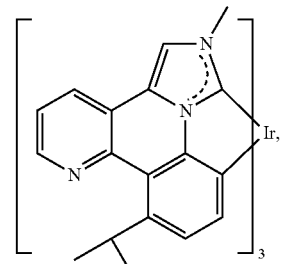
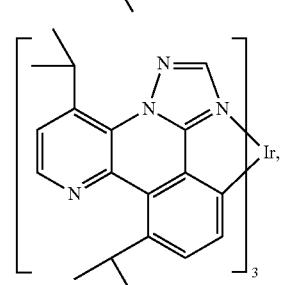
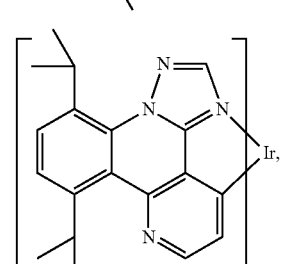
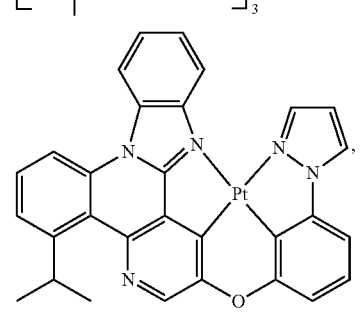

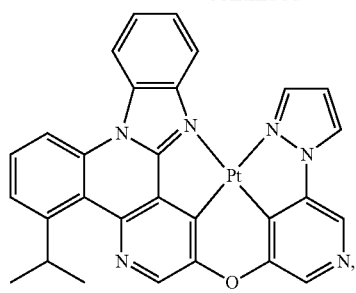
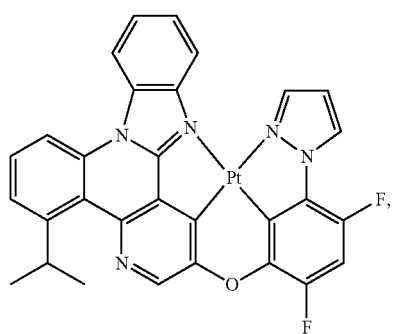
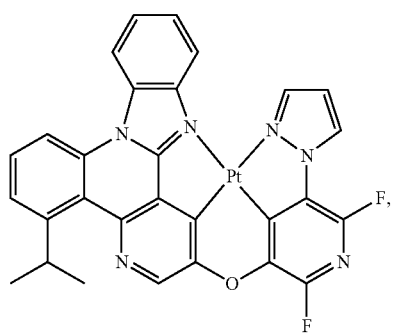
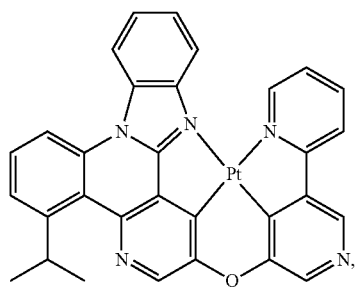
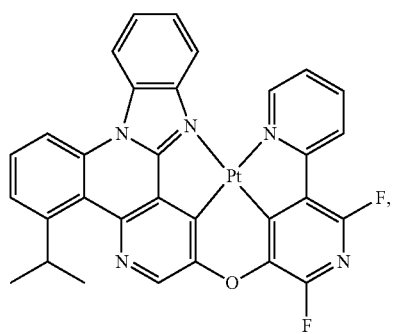
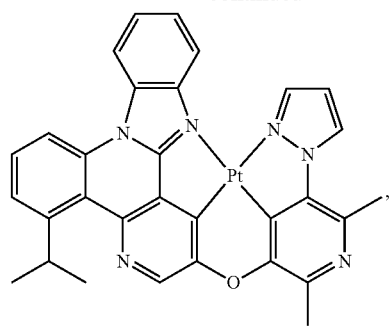
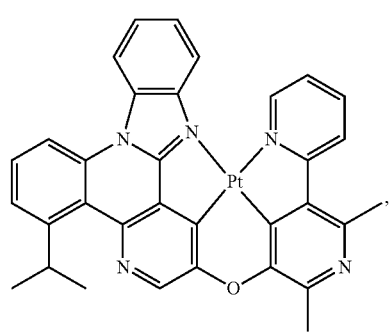
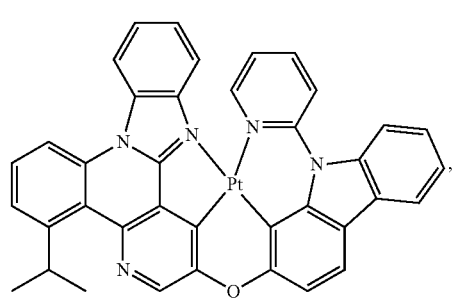
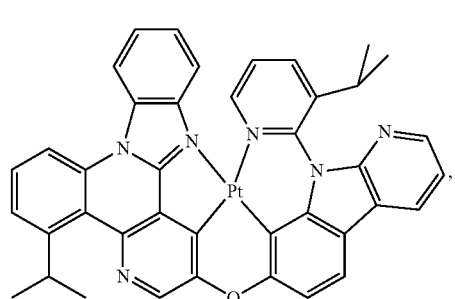
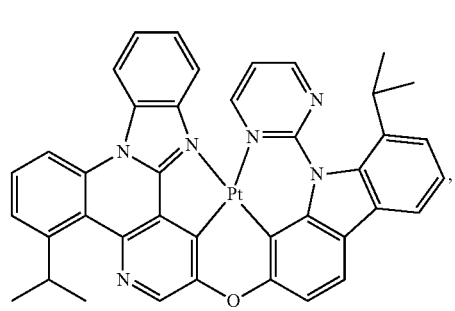

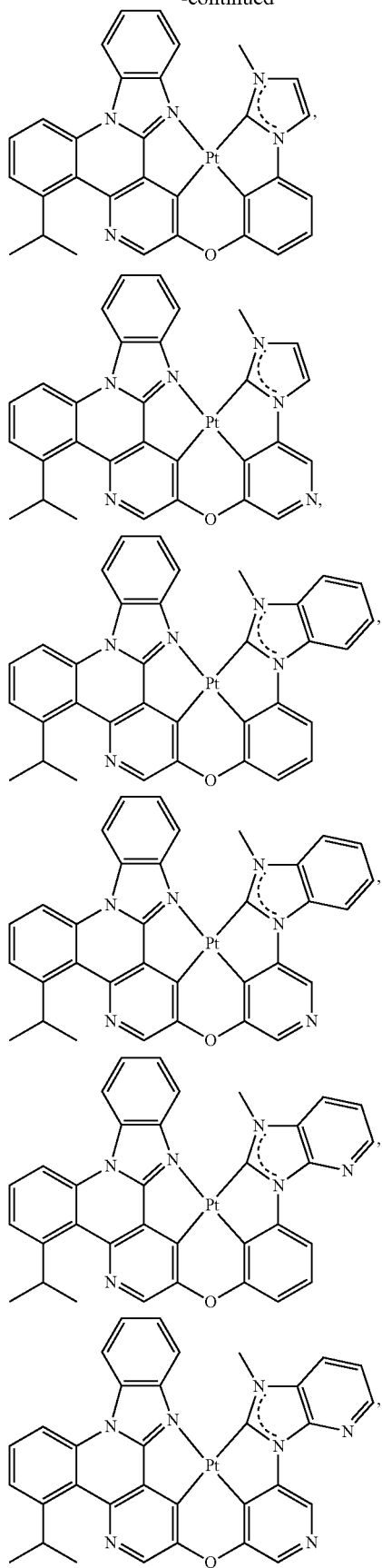
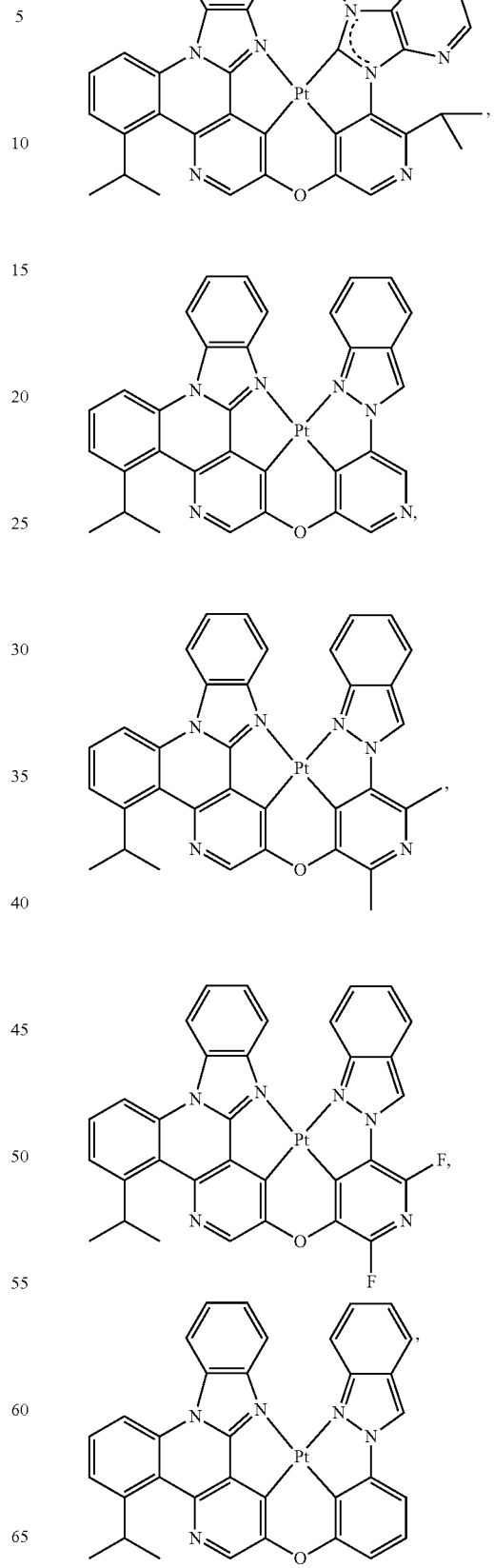

25
-continued
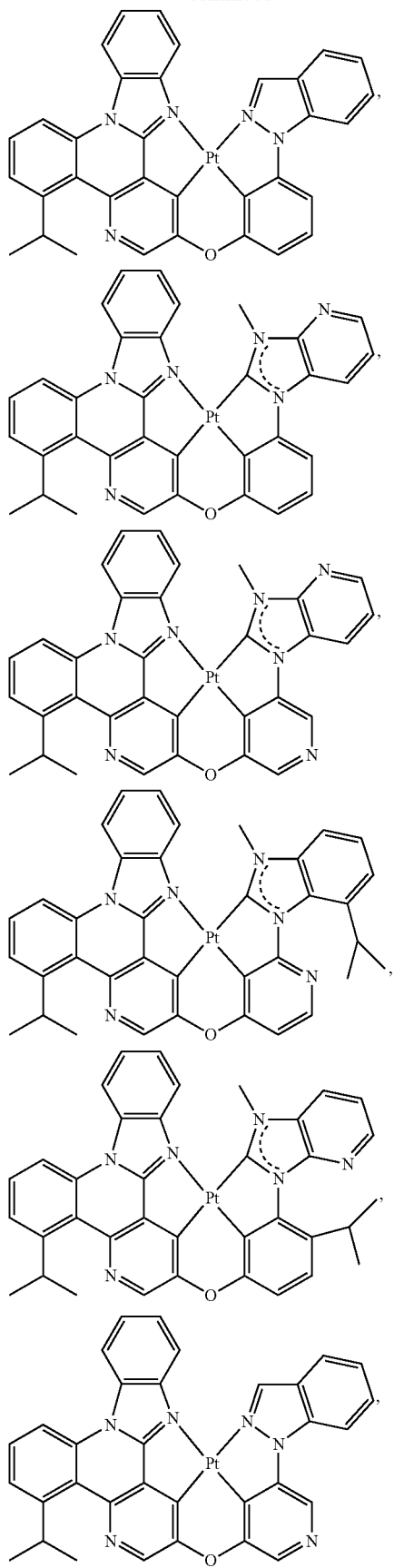
26
-continued
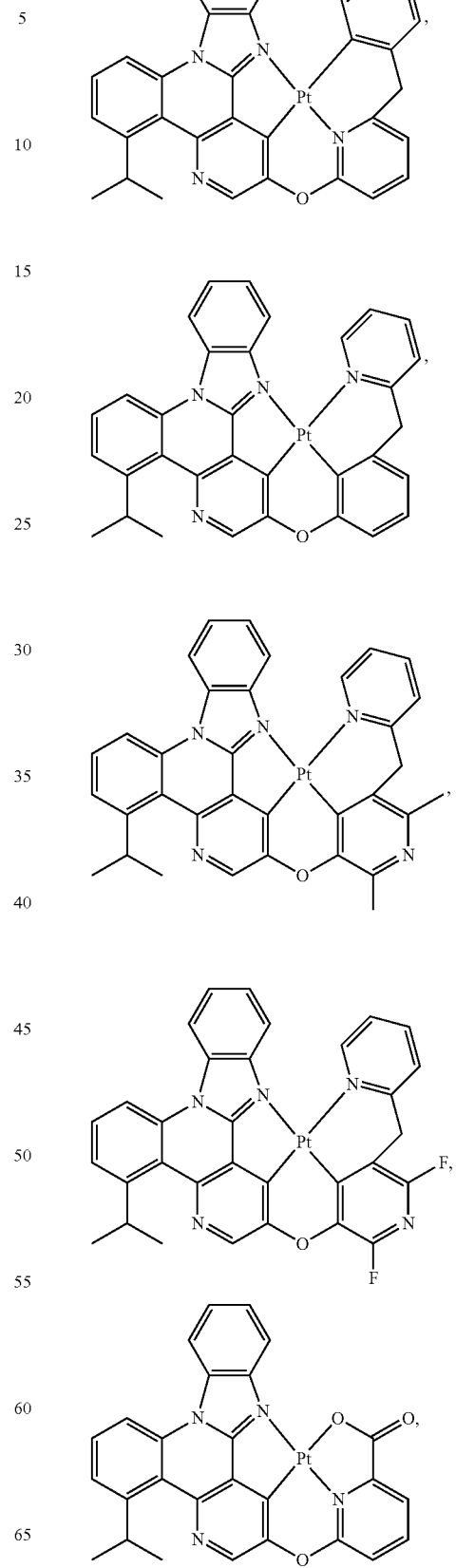

-continued
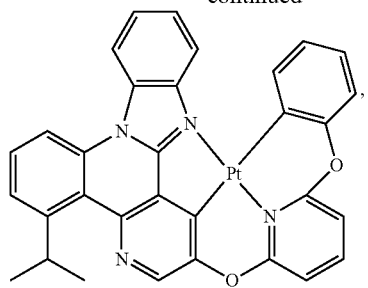
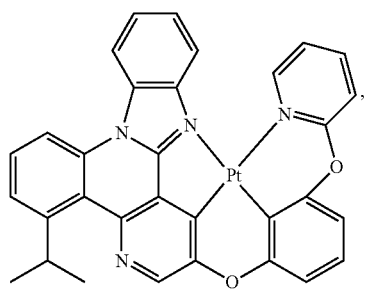
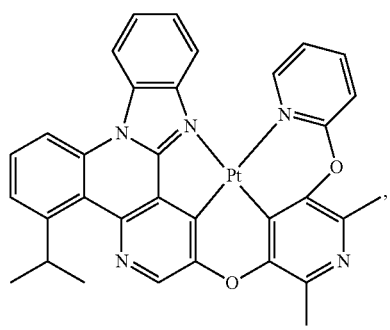
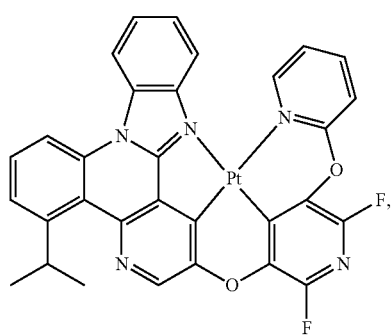
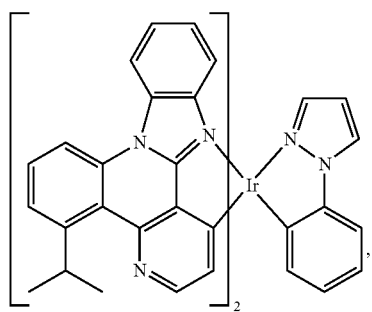
-continued
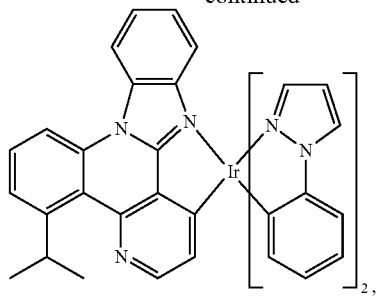
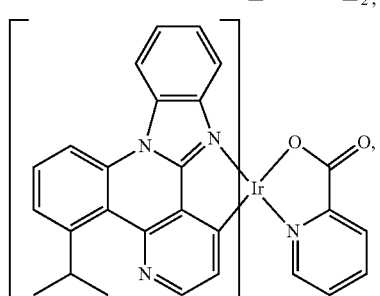
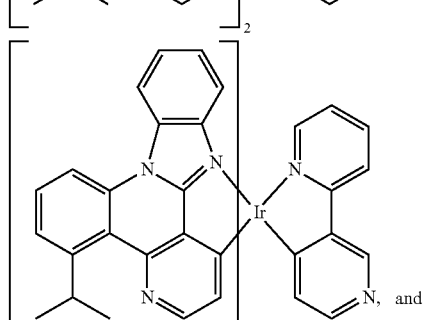, and
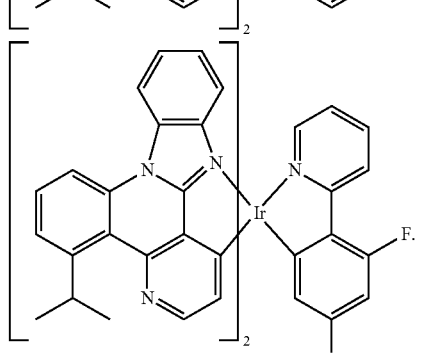
According to another embodiment, a compound is provided that comprises a ligand L selected from the group A consisting of:
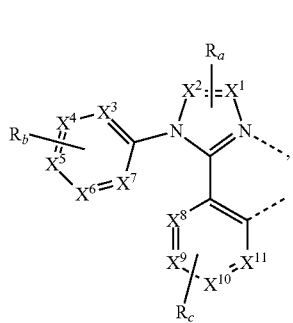

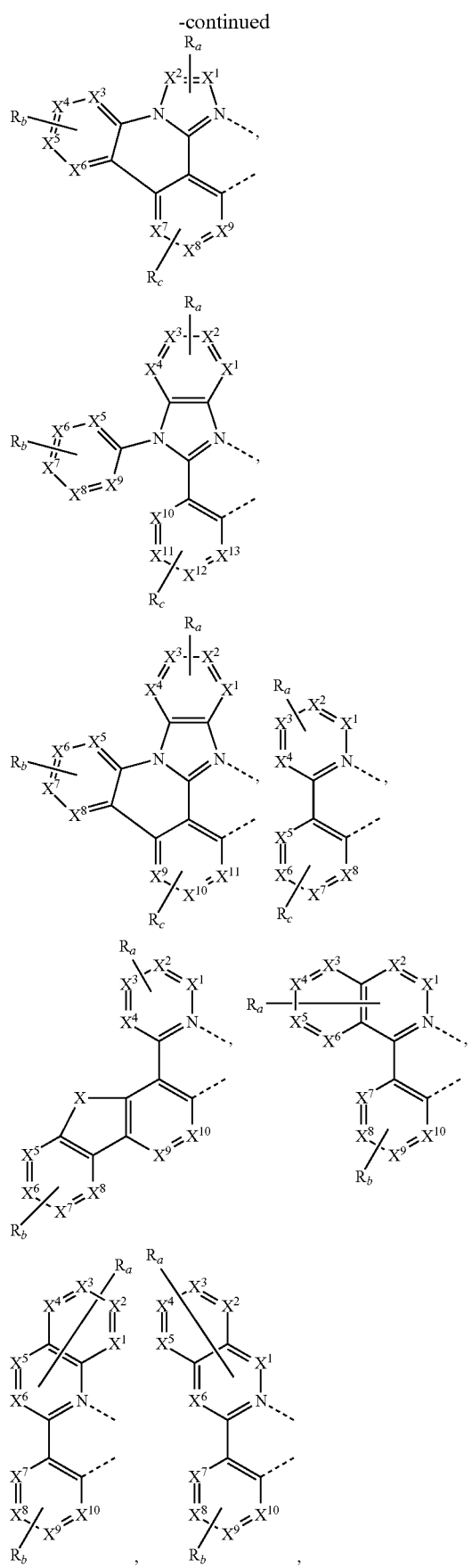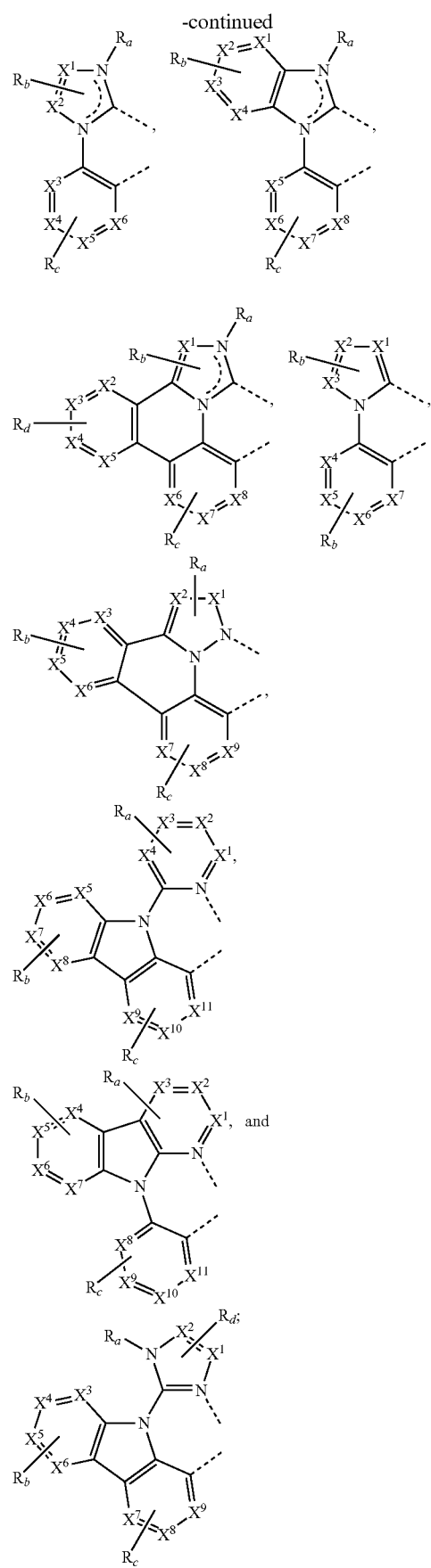

wherein each $X^1$ to $X^{13}$ are independently selected from the group consisting of carbon and nitrogen;

wherein X is selected from the group consisting of BR, NR, PR, O, S, Se, C=O, S=O, SO$_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound comprises at least one intramolecular hydrogen bonding interaction as shown in the scheme:

$$Z^1\text{---}H\text{----}Z^2, \qquad \text{scheme 1;}$$

wherein $Z^1$ is selected from the group consisting of carbon, silicon, nitrogen, and oxygen;

wherein $Z^2$ is selected from the group consisting of nitrogen, oxygen, and fluorine; and wherein in scheme 1, the proton NMR chemical shift of H is shifted downfield by at least 35% compared to the compound when $Z^2$ is carbon.

In one embodiment, the proton NMR chemical shift of H is shifted downfield by at least 37% compared to the compound when $Z^2$ is carbon.

According to another embodiment, a first device comprising a first organic light emitting device is also provided. The first organic light emitting device can include an anode, a cathode, and an organic layer, disposed between the anode and the cathode. The organic layer can include a compound comprising a ligand L. The first device can be a consumer product, an organic light-emitting device, an electronic component module, and/or a lighting panel.

In one embodiment, the first device comprises a first organic light emitting device, the first organic light emitting device comprising:
an anode;
a cathode; and
an organic layer, disposed between the anode and the cathode, comprising a compound comprising a ligand L selected from the group A consisting of

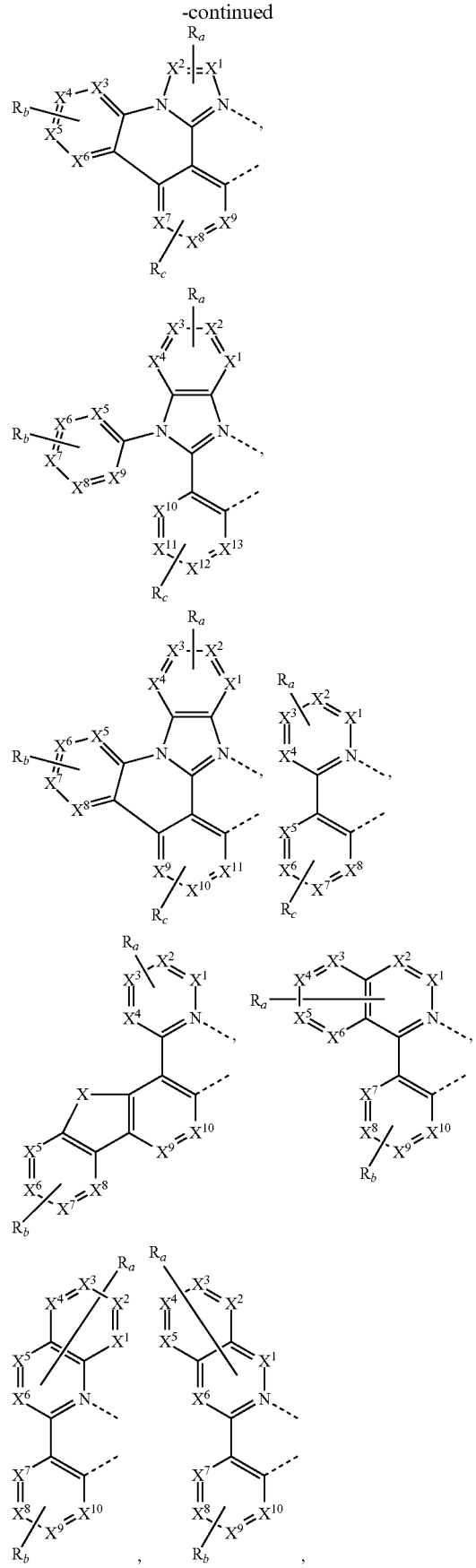

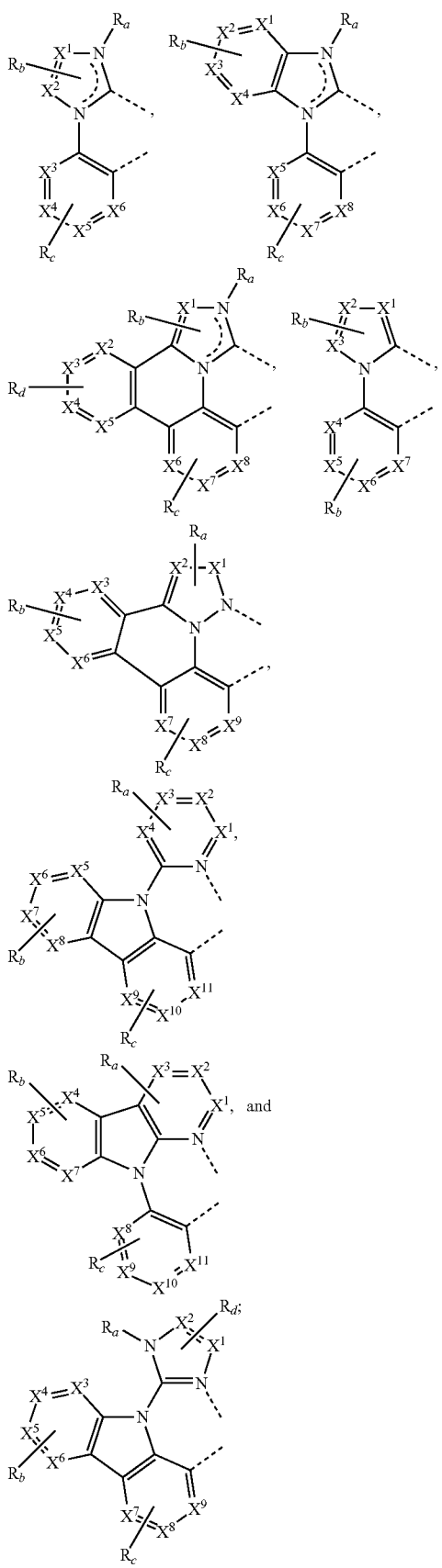

wherein each $X^1$ to $X^{13}$ are independently selected from the group consisting of carbon and nitrogen;

wherein X is selected from the group consisting of BR, NR, PR, O, S, Se, C=O, S=O, $SO_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound has at least one intramolecular hydrogen bonding interaction as shown in the scheme:

$$Z^1—H\text{----}Z^2, \qquad \text{scheme 1;}$$

wherein $Z^1$ is selected from the group consisting of carbon, silicon, nitrogen, and oxygen;

wherein $Z^2$ is selected from the group consisting of nitrogen, oxygen, and fluorine; and wherein;

(a) in scheme 1, the proton NMR chemical shift of H is shifted downfield by at least 1.3 ppm compared to the compound when $Z^2$ is carbon; or (b) in scheme 1, the proton NMR chemical shift of H is shifted downfield by at least 35% compared to the compound when $Z^2$ is carbon.

In one embodiment, the first device is selected from the group consisting of a consumer product, an electronic component module, an organic light-emitting device, and a lighting panel. In another embodiment, the organic layer is an emissive layer and the compound is an emissive dopant or a non-emissive dopant. In another embodiment, the organic layer is a charge transporting layer and the compound is a charge transporting material in the organic layer. In another embodiment, the organic layer is a blocking layer and the compound is a blocking material in the organic layer.

In one embodiment, the organic layer further comprises a host; wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$-$Ar_2$, $C_nH_{2n}$—$Ar_1$, or no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In one embodiment, the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

In one embodiment, the organic layer further comprises a host and the host is selected from the group consisting of:
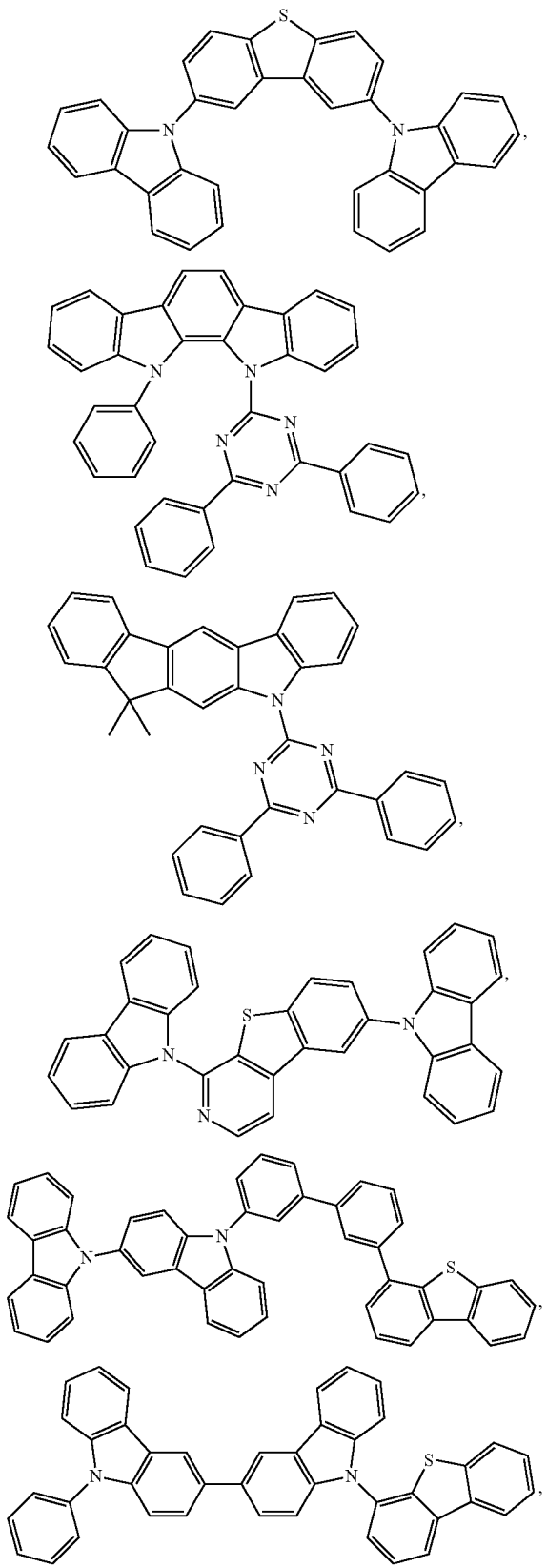
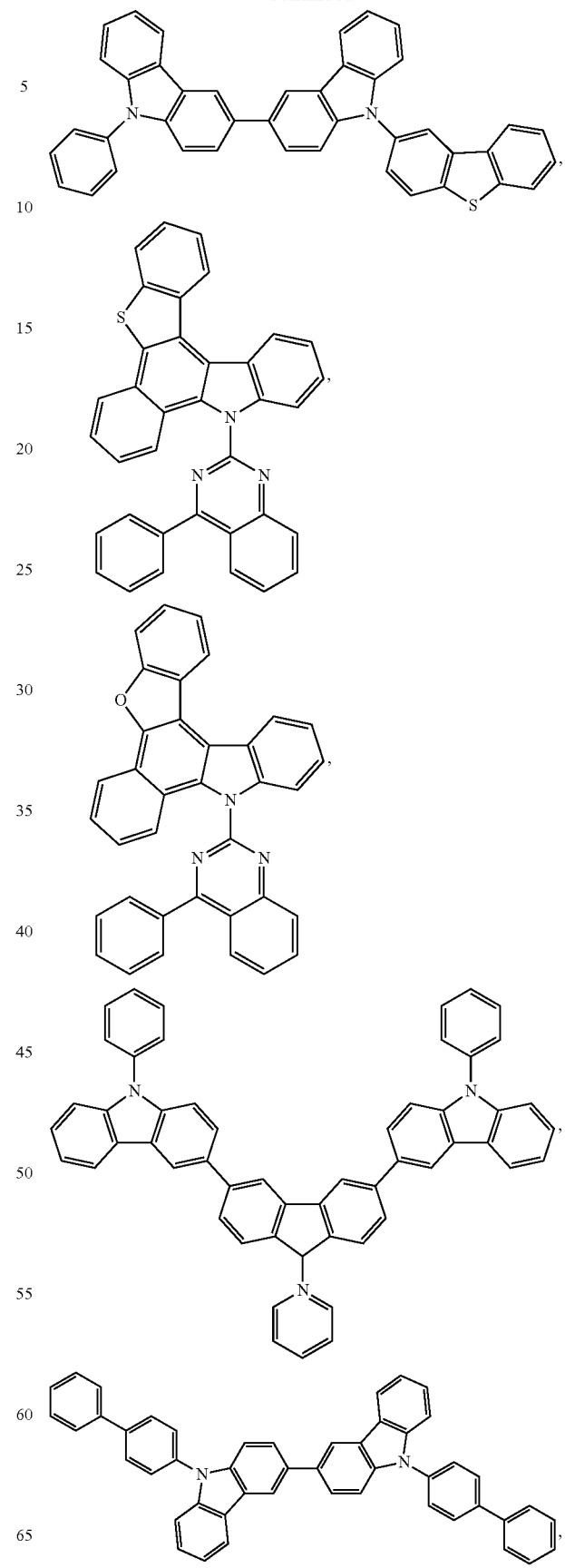

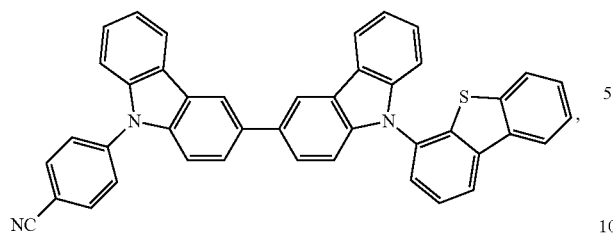

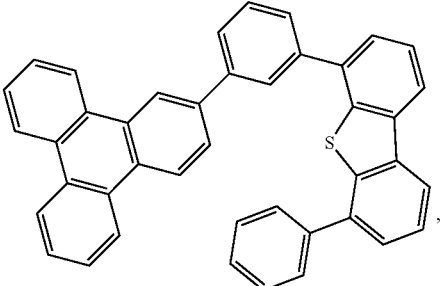

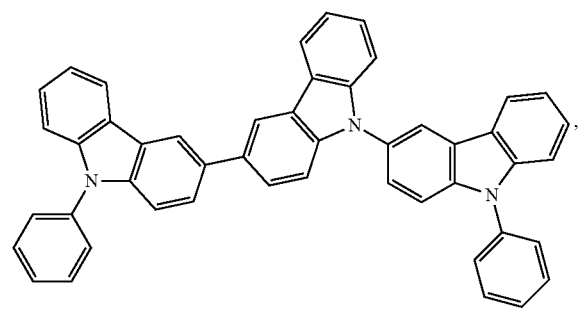

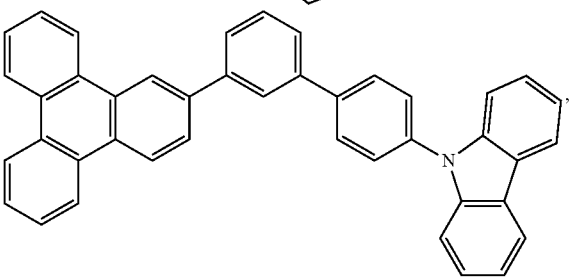

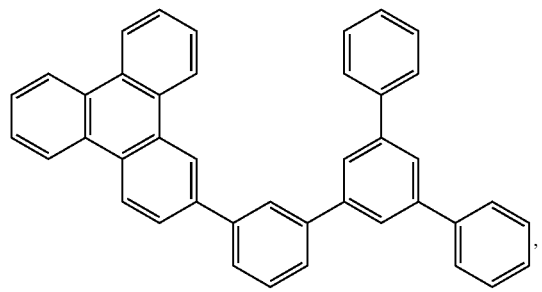

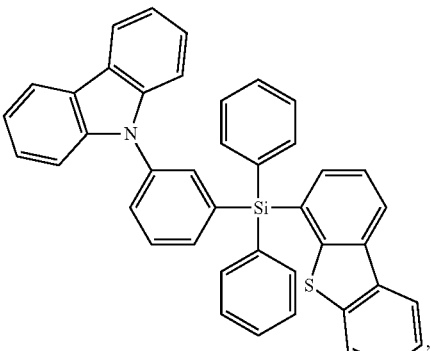

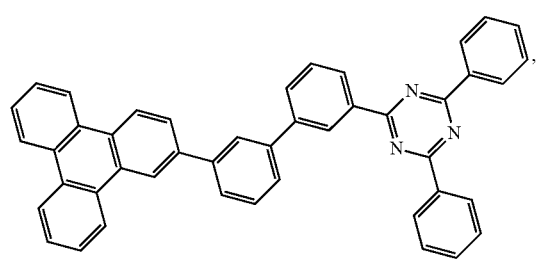

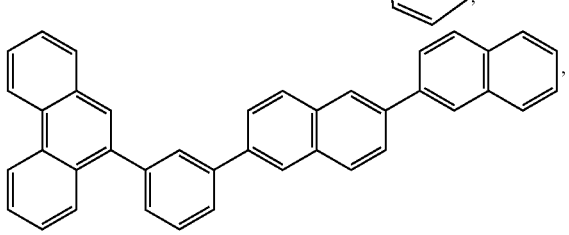

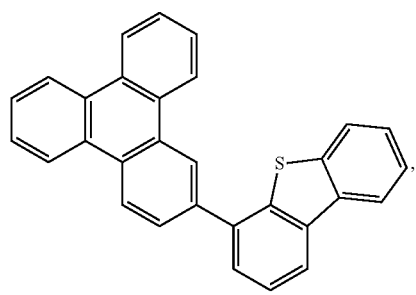

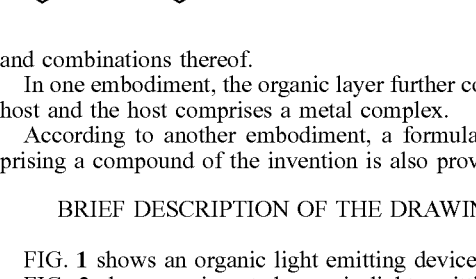

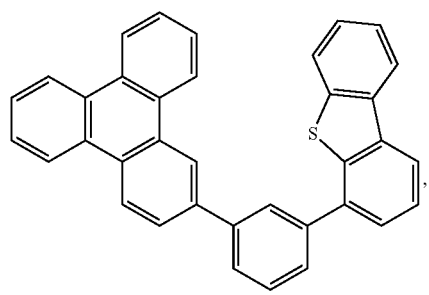

and combinations thereof.

In one embodiment, the organic layer further comprises a host and the host comprises a metal complex.

According to another embodiment, a formulation comprising a compound of the invention is also provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 which is incorporated by reference in its entirety.

Figure 1:
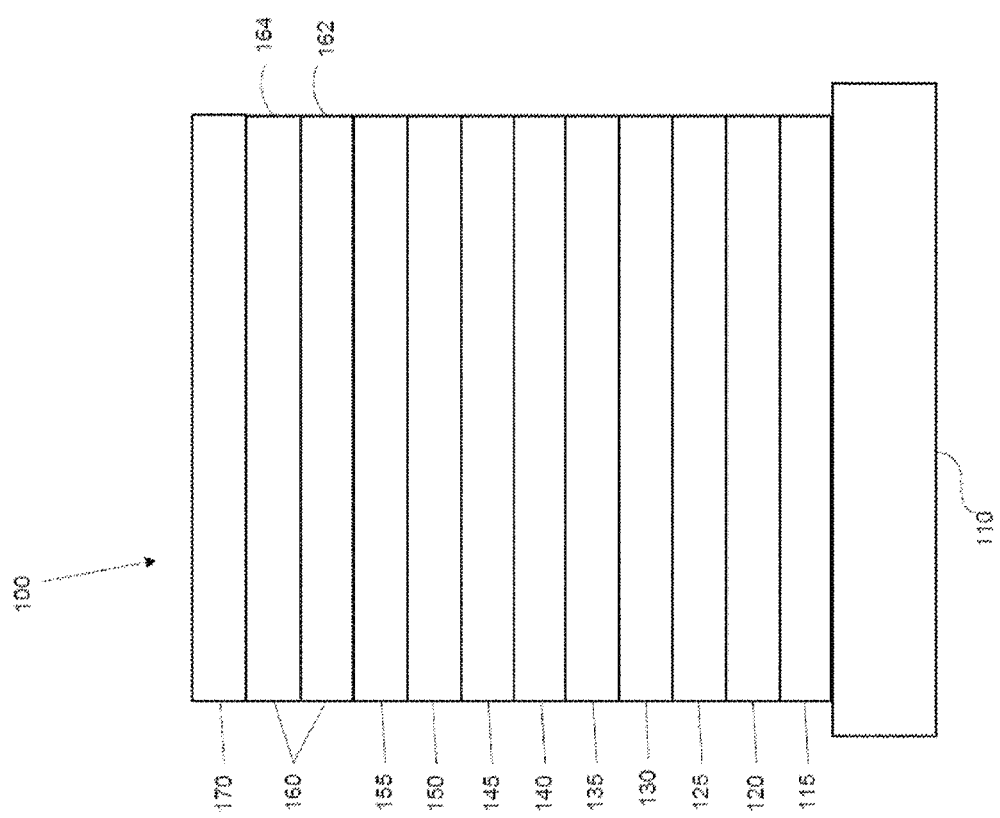
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 which is incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
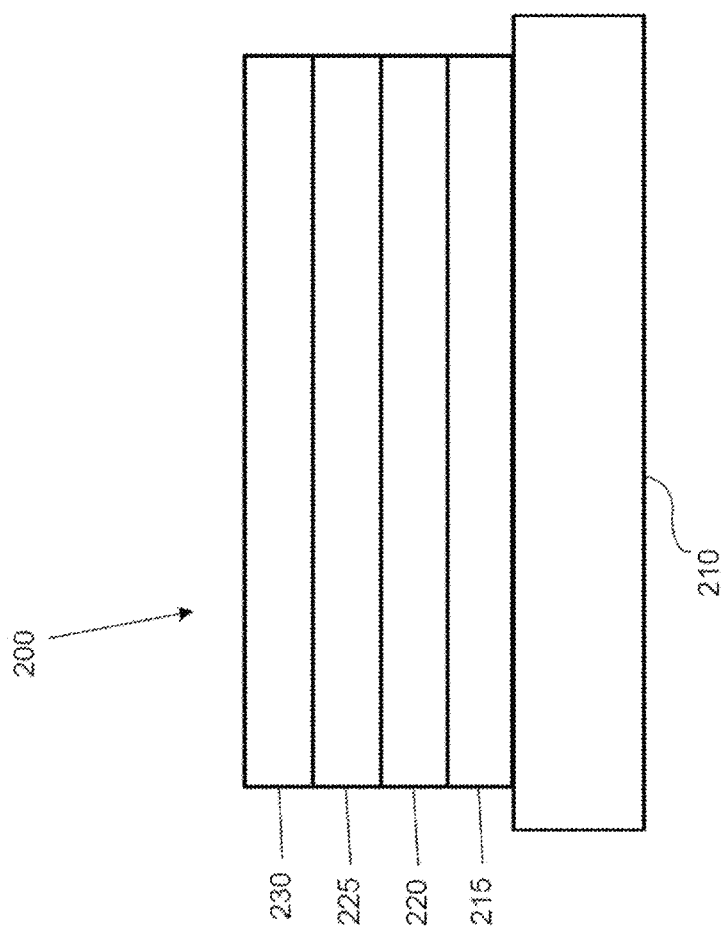
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

A proposed mechanism for the decomposition of complexes that contain an uncoordinated nitrogen is an event where the uncoordinated nitrogen acts as a base by deprotonating a neighboring molecule, leading to non-emissive and potentially ionic reaction products. This event may happen in the excited state or in the presence of charged states found in the device environment. Multi-ring scaffolds, such as the azaphenanthridine benzimidazole (APBI) ligand, may be useful to provide a functional site that can be substituted in order to address this decomposition mechanism.

Two approaches have been pursued in order to improve stability. The first approach places a steric group at the site in order to shield the lone pair of the uncoordinated nitrogen from exposure to protons on a neighboring molecule. For example, Compounds 1-6 contain substitution designed to sterically shield the nitrogen from protonation:

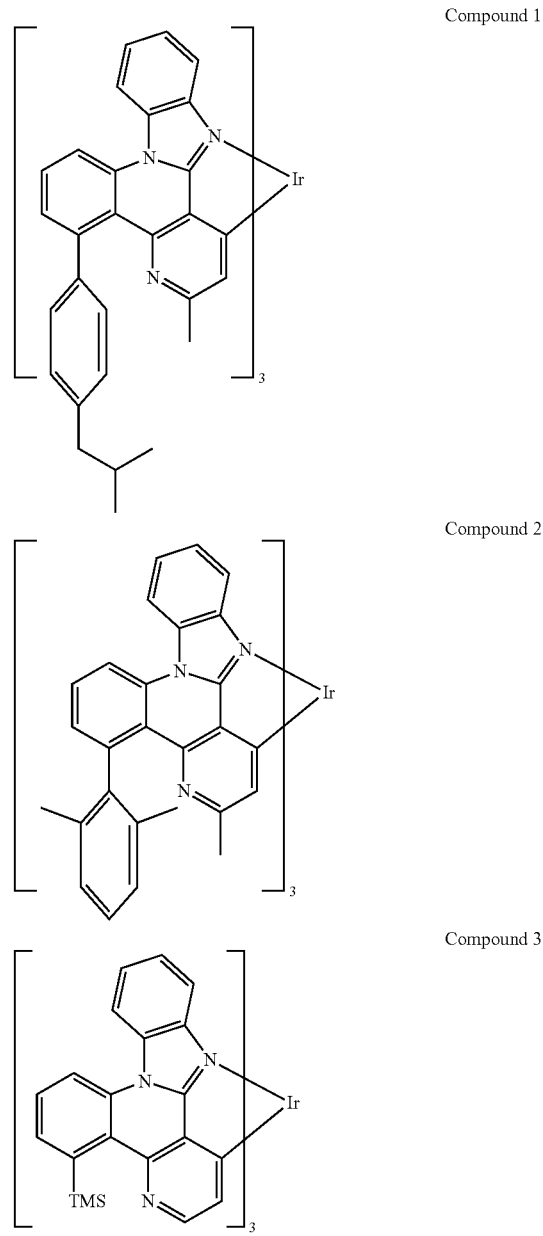

Compound 1

Compound 2

Compound 3

Compound 4

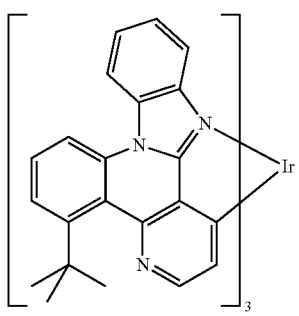

Compound 5

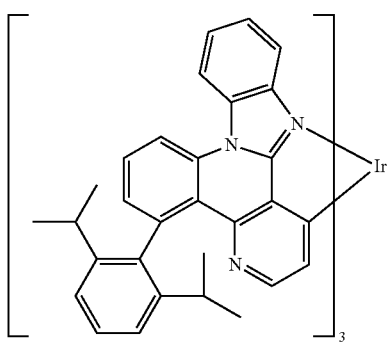

Compound 6

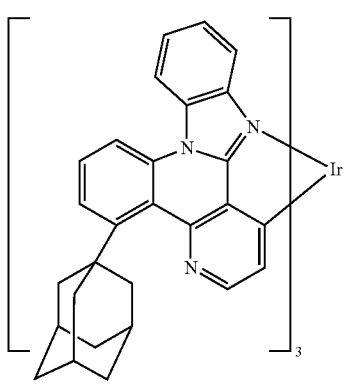

Figure 3:
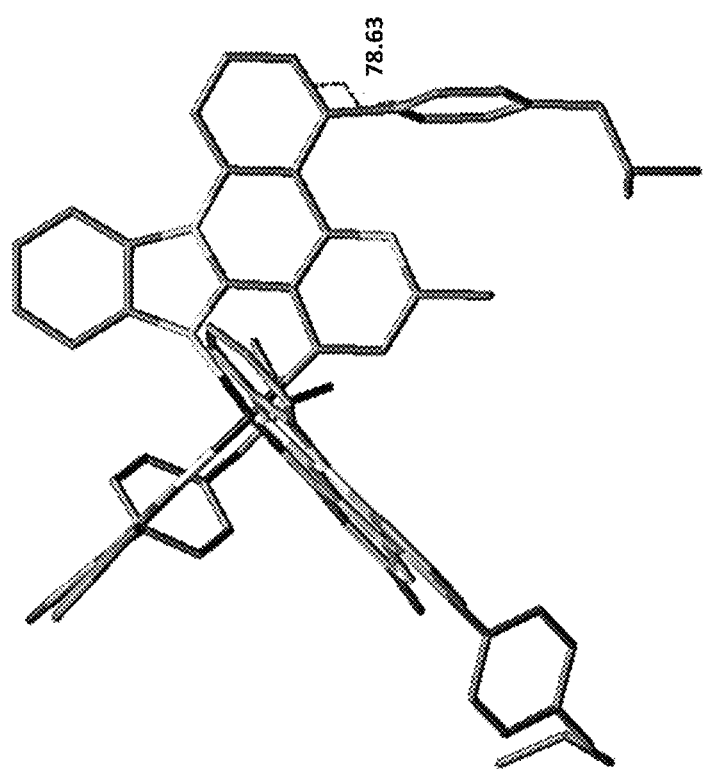
FIG. 3 shows the X-Ray crystal structure of Compound 1. The aryl substitution is twisted out of plane, shielding the lone pair of the uncoordinated nitrogen.
Figure 4:
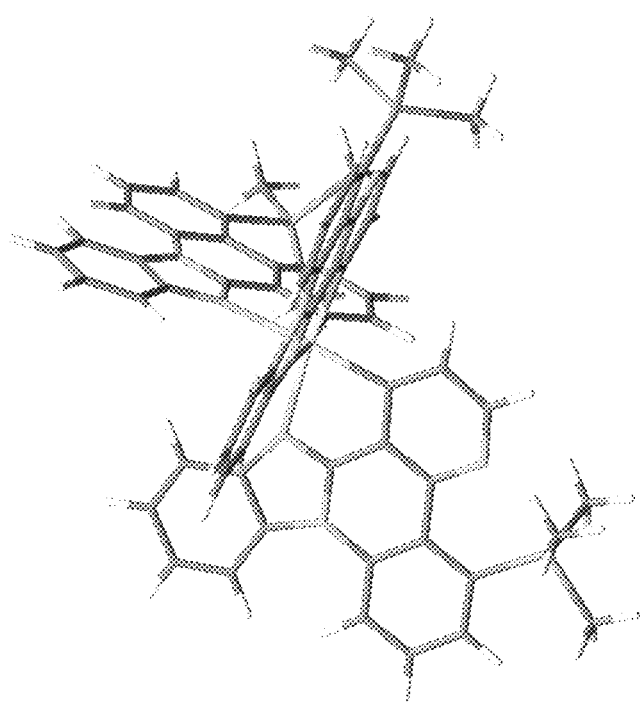
FIG. 4 shows an image of the minimized geometry for Compound 3. The methyl groups are configured to minimize steric interaction, forming a pocket around the nitrogen lone pair.

In Compound 1 and Compound 2, an aryl group is substituted on the ring opposite the uncoordinated nitrogen. Due to steric interaction, the ring is largely twisted out of plane, leading to a minimal increase in triplet energy. In addition, the plane of the aryl ring sits over the lone pair of the uncoordinated nitrogen, which should inhibit its exposure to nearby protons of neighboring molecules. The configuration of the aryl ring can be seen in the X-Ray crystal structure of Compound 1 (FIG. 3). However, an unexpected negative consequence of an aromatic substitution at this site is a decrease in PLQY. This can be mitigated to some extent by making the ring system more rigid by introducing 2,6-alkyl substitutions on the twisted aryl ring, such as in Compound 2. Compound 1 is measured to have a PLQY of 13% in a polymethylmethcrylate (PMMA) matrix. This improves markedly to 28% for Compound 2 with a more rigid 2,6-dimethyl phenyl substitution. However APBI complexes without aryl substitutions at this position typically have PLQY of 70-90%. The use of a non-aromatic substituent at the site of the uncoordinated nitrogen may be preferable in order to avoid the decrease in PLQY observed when the substituent is aromatic. For example, in the energy-minimized calculated geometry of Compound 3, which has non-aromatic substitution with a trimethylsilyl (TMS) group, the methyl groups of the TMS group point out of plane from the aromatic ring system, creating a pocket around the potentially-reactive lone pair of the uncoordinated nitrogen (FIG. 4).

As demonstrated herein, a second approach to improve stability comprises providing a hydrogen atom such that a static hydrogen bonding interaction is established between it and the lone pair of electrons on the uncoordinated nitrogen.

This configuration serves to mitigate the reactivity of the lone pair, stabilizing the molecule from intermolecular degradation, and therefore improving the stability of the complex in a device. An exemplary azaphenanthridine benzimidazole (APBI) ligand is depicted below, wherein the hydrogen is defined as H*:

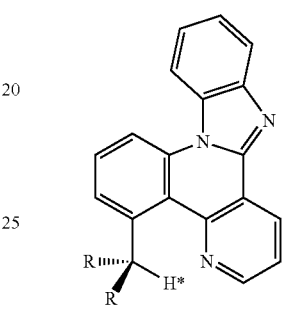

It can be seen that H* points towards the lone pair of the nitrogen. It is believed that the proximity of the proton to the uncoordinated nitrogen is caused by steric repulsion between the methyl substituents on the isopropyl group and the ring system on the APBI. Using this strategy, complexes can be designed to place a proton in close proximity to the lone pair of the nitrogen in order to form a static intramolecular hydrogen bond. Therefore if the lone pair of the nitrogen were to increase in basicity in the excited or charged state, then the lone pair and H* should be able to reversibly interact. On the other hand, a molecule without an intramolecular hydrogen bond could induce an irreversible degradation event by deprotonating a nearby molecule in the excited or charged state.

Compounds of the Invention:

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound comprising a ligand L selected from the group A consisting of:

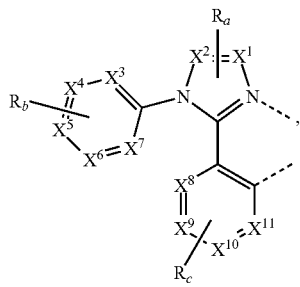

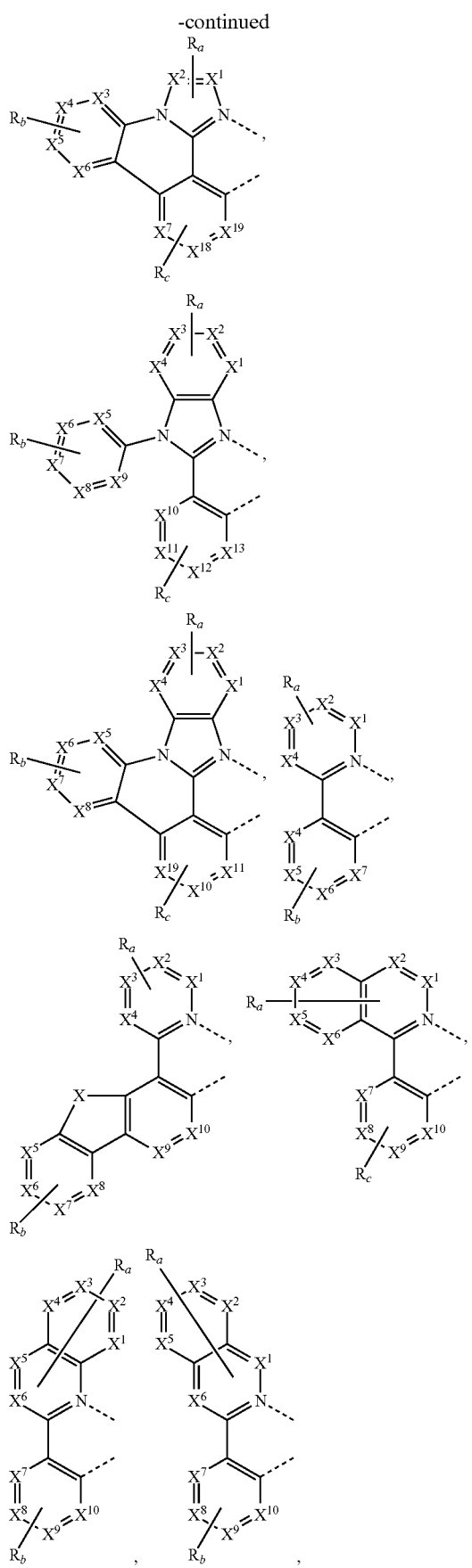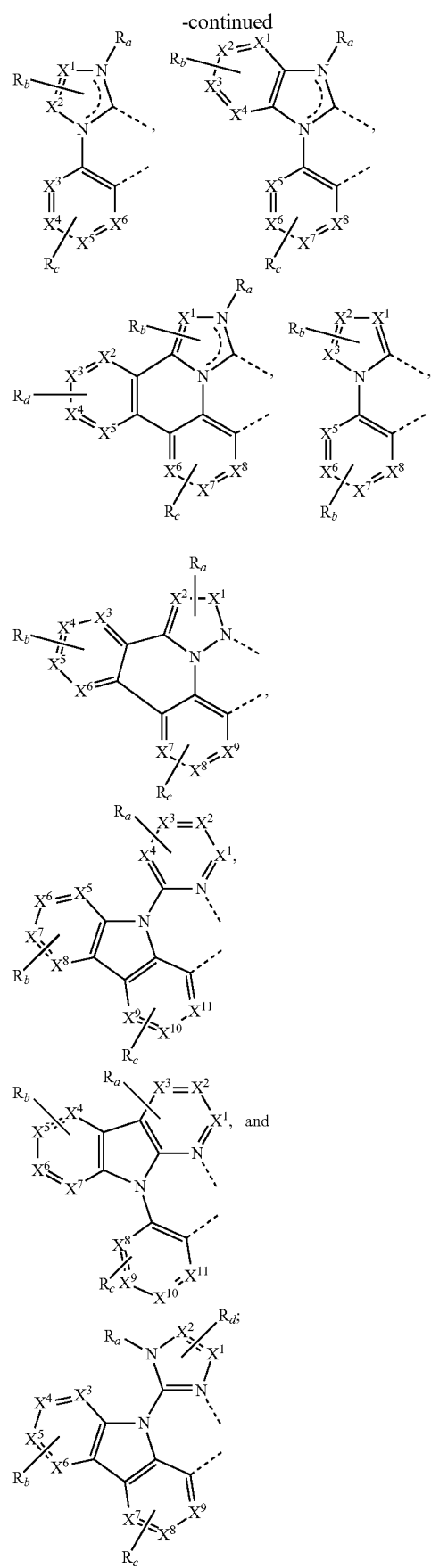

wherein each $X^1$ to $X^{13}$ are independently selected from the group consisting of carbon and nitrogen;

wherein X is selected from the group consisting of BR, NR, PR, O, S, Se, C=O, S=O, $SO_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound has at least one intramolecular hydrogen bonding interaction as shown in the scheme:

$$Z^1\text{—H----}Z^2, \qquad \text{scheme 1;}$$

wherein $Z^1$ is selected from the group consisting of carbon, silicon, nitrogen, and oxygen;

wherein $Z^2$ is selected from the group consisting of nitrogen, oxygen, and fluorine; and wherein in scheme 1, the proton NMR chemical shift of H is shifted downfield by at least 1.3 ppm compared to the compound when $Z^2$ is carbon.

In another aspect, the compound of the invention is a compound comprising a ligand L selected from the group A consisting of

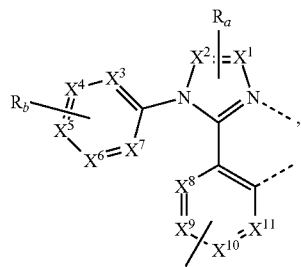

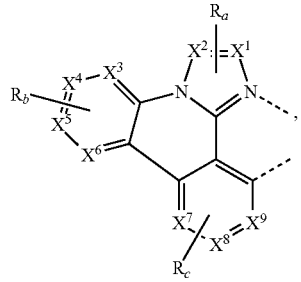

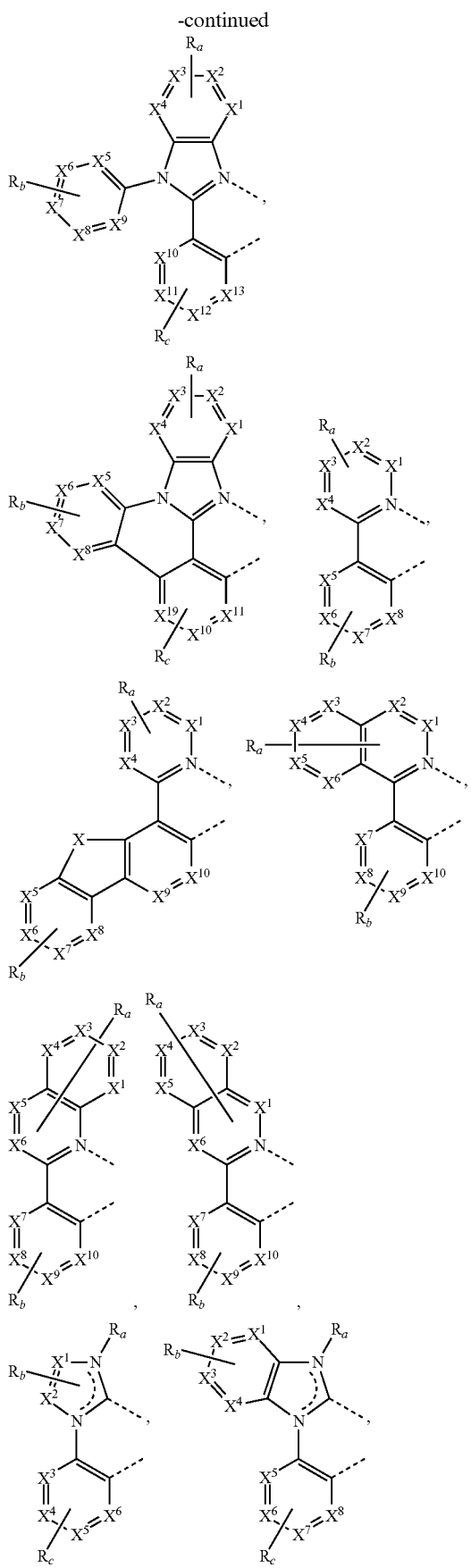

-continued

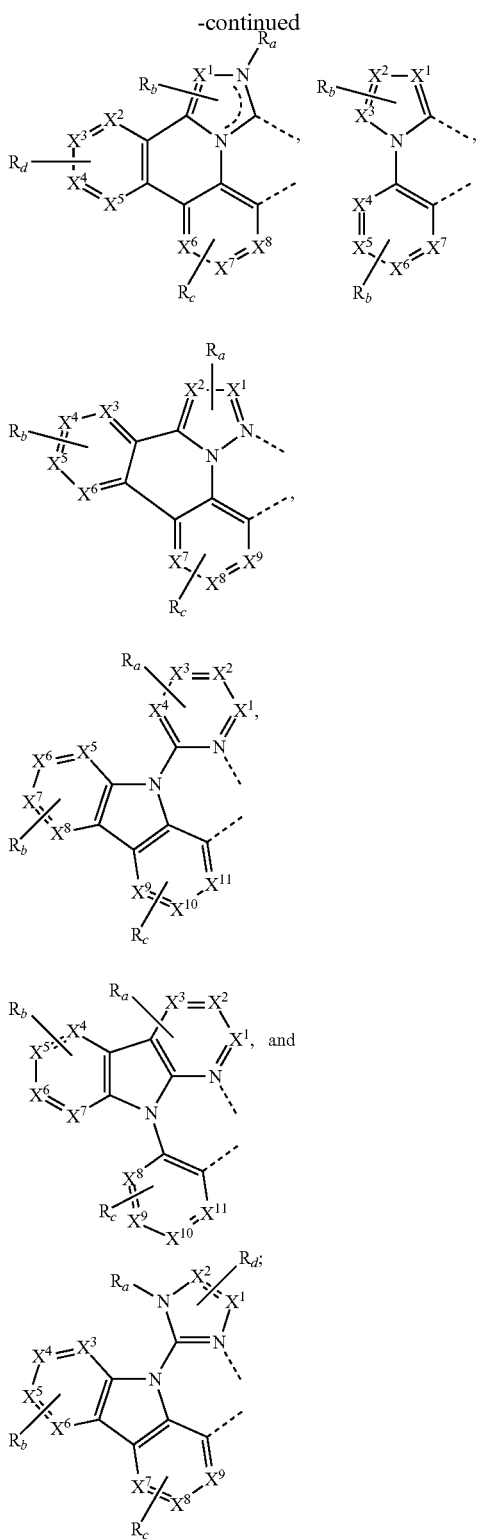

wherein each $X^1$ to $X^{13}$ are independently selected from the group consisting of carbon and nitrogen;

wherein X is selected from the group consisting of BR, NR, PR, O, S, Se, C=O, S=O, $SO_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound has at least one intramolecular hydrogen bonding interaction as shown in the scheme:

$$Z^1\text{—H----}Z^2, \qquad \text{scheme 1;}$$

wherein $Z^1$ is selected from the group consisting of carbon, silicon, nitrogen, and oxygen;

wherein $Z^2$ is selected from the group consisting of nitrogen, oxygen, and fluorine; and wherein;

(a) in scheme 1, the proton NMR chemical shift of H is shifted downfield by at least 1.3 ppm compared to the compound when $Z^2$ is carbon; or (b) in scheme 1, the proton NMR chemical shift of H is shifted downfield by at least 35% compared to the compound when $Z^2$ is carbon.

In another aspect, the compound of the invention is a compound comprising a ligand L selected from the group A consisting of:

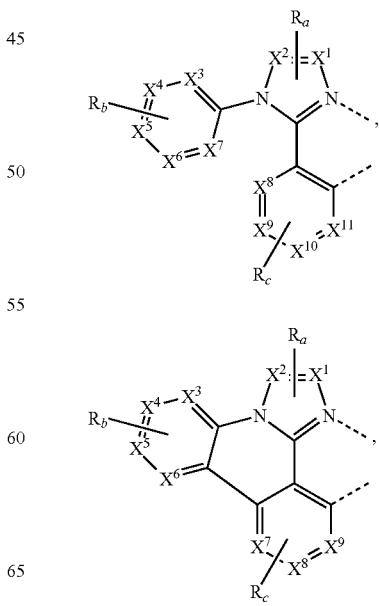

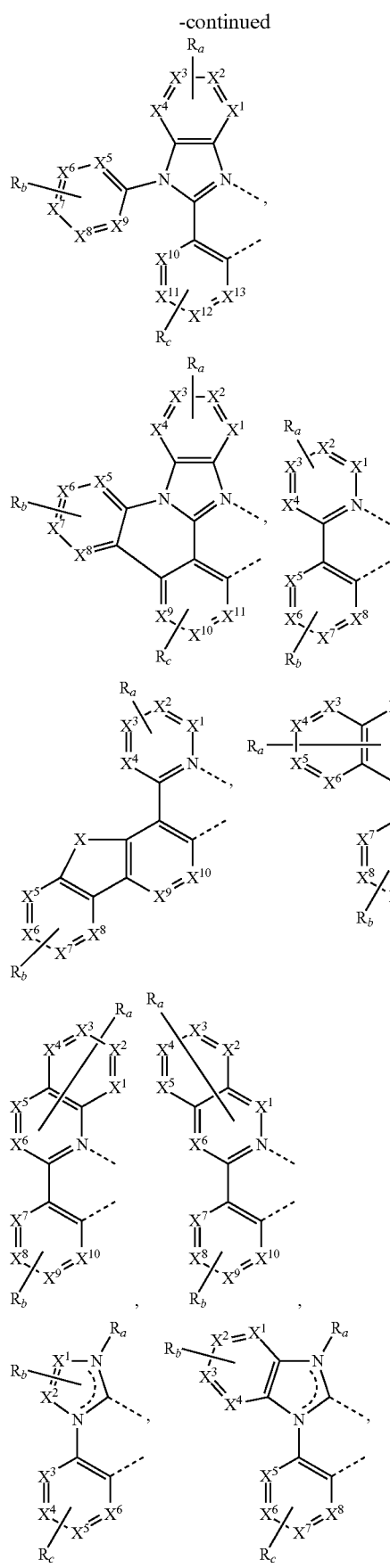
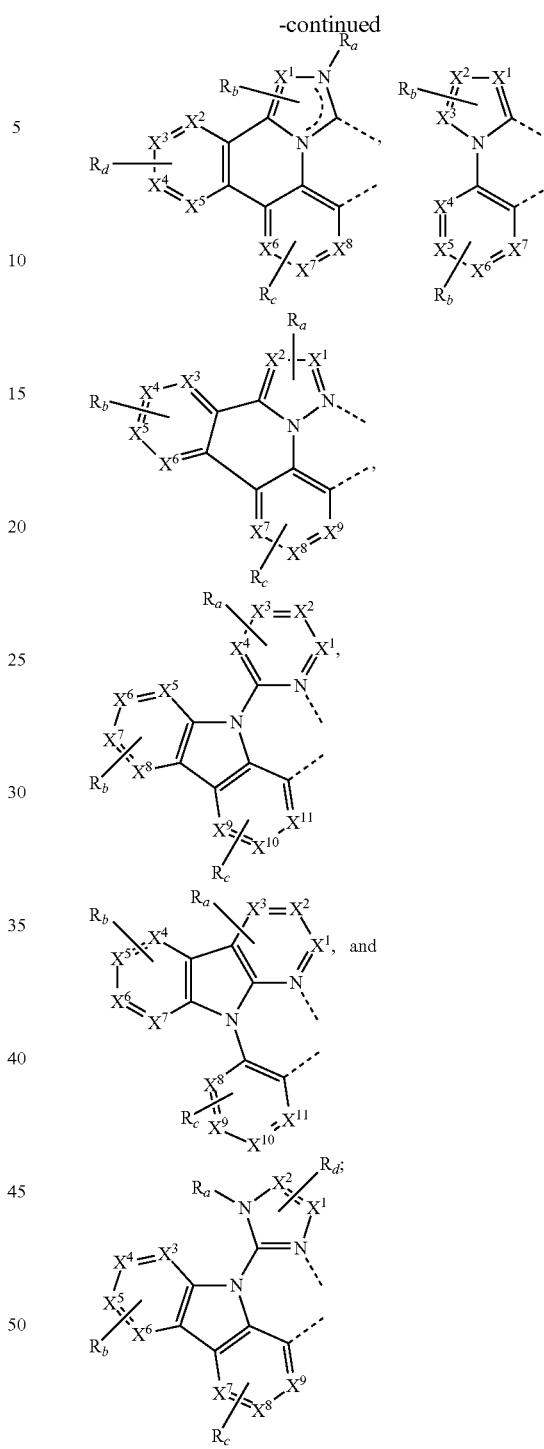

wherein each $X^1$ to $X^{13}$ are independently selected from the group consisting of carbon and nitrogen;

wherein X is selected from the group consisting of BR, NR, PR, O, S, Se, C=O, S=O, $SO_2$, CRR', SiRR', and GeRR';

wherein R and R' are optionally fused or joined to form a ring;

wherein each $R_a$, $R_b$, $R_c$, and $R_d$ may represent from mono substitution to the possible maximum number of substitution, or no substitution;

wherein each R, R', $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring;

wherein the ligand L is coordinated to a metal M;

wherein the ligand L is optionally linked with other ligands to comprise a tridentate, tetradentate, pentadentate or hexadentate ligand;

wherein the compound comprises at least one intramolecular hydrogen bonding interaction as shown in the scheme:

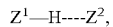    scheme 1;

wherein $Z^1$ is selected from the group consisting of carbon, silicon, nitrogen, and oxygen;

wherein $Z^2$ is selected from the group consisting of nitrogen, oxygen, and fluorine; and wherein in scheme 1, the proton NMR chemical shift of H is shifted downfield by at least 35% compared to the compound when $Z^2$ is carbon.

The metal M is not particularly limited. Examples of metals useful in the compounds of the present invention include, but are not limited to, transition metals such as Ir, Pt, Au, Re, Ru, W, Rh, Ru, Os, Pd, Ag, Cu, Co, Zn, Ni, Pb, Al, and Ga. In one embodiment, M is selected from the group consisting of Ir, Rh, Re, Ru, Os, Pt, Au, and Cu. In another embodiment, M is Ir or Pt. In one embodiment, M is Ir. In another embodiment, M is Pt.

In one embodiment, X is selected from the group consisting of BR, NR, PR, O, S, Se, C=O, S=O, $SO_2$, CRR', SiRR', and GeRR'. In one embodiment, X is O.

In one aspect, the compounds of the invention include at least one intramolecular hydrogen bonding interaction to prevent deprotonation of neighboring molecules and to prevent protonation of an uncoordinated nitrogen. An exemplary intramolecular hydrogen bonding interaction can be found in scheme 1:

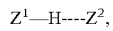    scheme 1;

As would be understood by one of ordinary skill in the art, $Z^1$ can be any atom capable of forming a covalent bond with H, while $Z^2$ can be any atom capable of forming a hydrogen bonding interaction with H. In one embodiment, $Z^1$ is selected from the group consisting of carbon, silicon, nitrogen, and oxygen. In one embodiment, $Z^2$ is selected from the group consisting of nitrogen, oxygen, and fluorine. In another embodiment, $Z^1$ is carbon, and $Z^2$ is nitrogen. In another embodiment, $Z^1$ is carbon of alkyl, and $Z^2$ is nitrogen of pyridine. In another embodiment, $Z^2$ is one of $X^1$ to $X^{13}$, and is nitrogen. In some embodiments, the location within the compound of $Z^1$ relative to $Z^2$ may be determined by the number of covalent bonds between $Z^1$ and $Z^2$. In one embodiment, $Z^1$ is at least 3 covalent bonds away from $Z^2$. In one embodiment, $Z^1$ is at least 4 covalent bonds away from $Z^2$. In another embodiment, $Z^1$ is at least 5 covalent bonds away from $Z^2$. In one embodiment, $Z^1$ is at least 6 covalent bonds away from $Z^2$.

An interaction between the hydrogen and $Z^2$ can be determined using any method known in the art. In one embodiment, the interaction is determined using computational methods, such as by inspecting the $Z^2$—H distance and spatial positioning in the minimized geometry. In one embodiment, the distance between H and $Z^2$ ranges from 1.5 Å to 2.4 Å. In one embodiment, the distance between H and $Z^2$ is equal to or less than 2.2 Å. In another embodiment, the distance between H and $Z^2$ is equal to or less than 2.16 Å. In another embodiment, the distance between H and $Z^2$ is equal to or less than 2.15 Å. In another embodiment, the interaction is determined using experimental methods, such as by measuring the $^1$H (proton) NMR chemical shift of the hydrogen-bonding proton. In one embodiment, the proton NMR chemical shift of H is shifted downfield by between 4.5 ppm and 7.0 ppm compared to the compound when $Z^2$ is carbon. In some embodiments, the NMR chemical shift of H may be shifted downfield by at least 1.3 ppm, at least 1.4 ppm, at least 1.5 ppm, at least 1.6 ppm, at least 1.7 ppm, at least 1.8 ppm, at least 1.9 ppm, or at least 2.0 ppm compared to the compound when $Z^2$ is carbon. In one embodiment, the proton NMR chemical shift of H is shifted downfield by at least 1.3 ppm compared to the compound when $Z^2$ is carbon. In another embodiment, the proton NMR chemical shift of H is shifted downfield by at least 1.4 ppm compared to the compound when $Z^2$ is carbon. In one embodiment, the proton NMR chemical shift of H is shifted downfield by between 30% and 60% compared to the compound when $Z^2$ is carbon. In some embodiments, the proton NMR chemical shift of H may be shifted downfield by at least 35%, at least 37%, at least 39%, at least 40%, at least 45%, or at least 50% compared to the compound when $Z^2$ is carbon. In one embodiment, the proton NMR chemical shift of H is shifted downfield by at least 35% compared to the compound when $Z^2$ is carbon. In another embodiment, the proton NMR chemical shift of H is shifted downfield by at least 37% compared to the compound when $Z^2$ is carbon In one embodiment, the interaction is determined by measuring the emission of the first peak wavelength at the high energy end at room temperature and comparing it to the emission at a different temperature. As used herein, the term "room temperature" refers to a temperature from about 20° C. to about 30° C. As demonstrated herein, it was observed that compounds exhibiting an intramolecular hydrogen bonding interaction may also have an unusual triplet emission blue-shift in room temperature solution compared to the emission at a lower temperature. In one embodiment, the compound has an emission with the first peak wavelength at the high energy end smaller at room temperature than that at 77K.

In one embodiment, the ligand L is selected from the group consisting of:

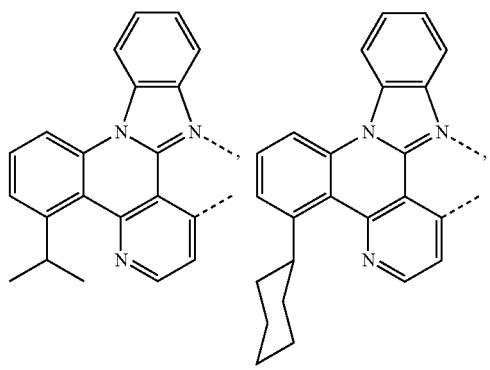

-continued
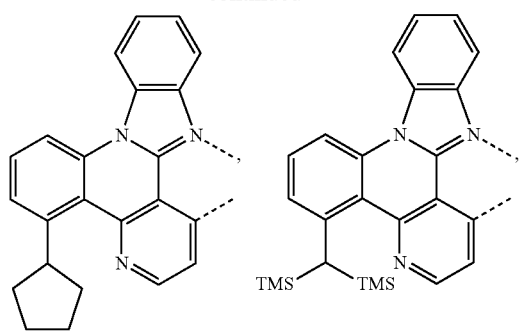
-continued
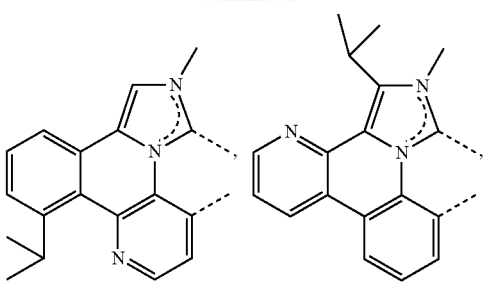
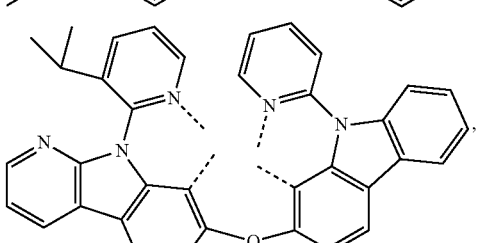
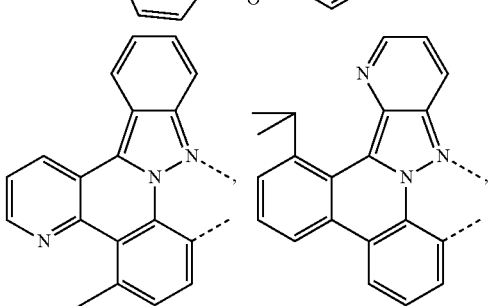
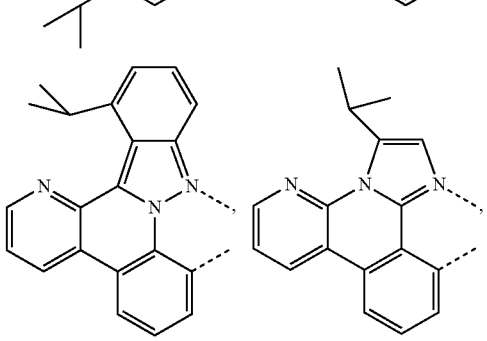
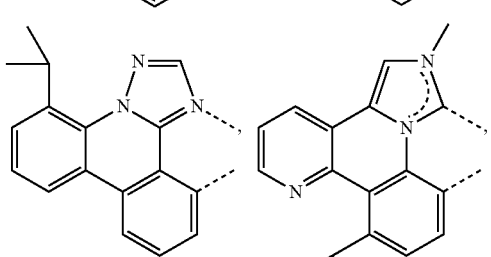
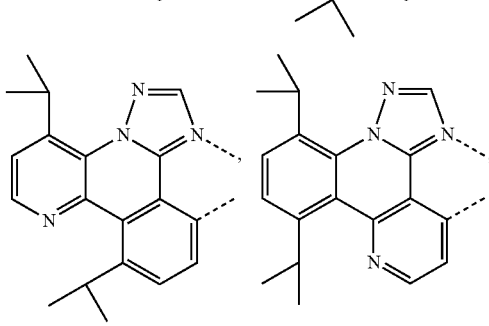

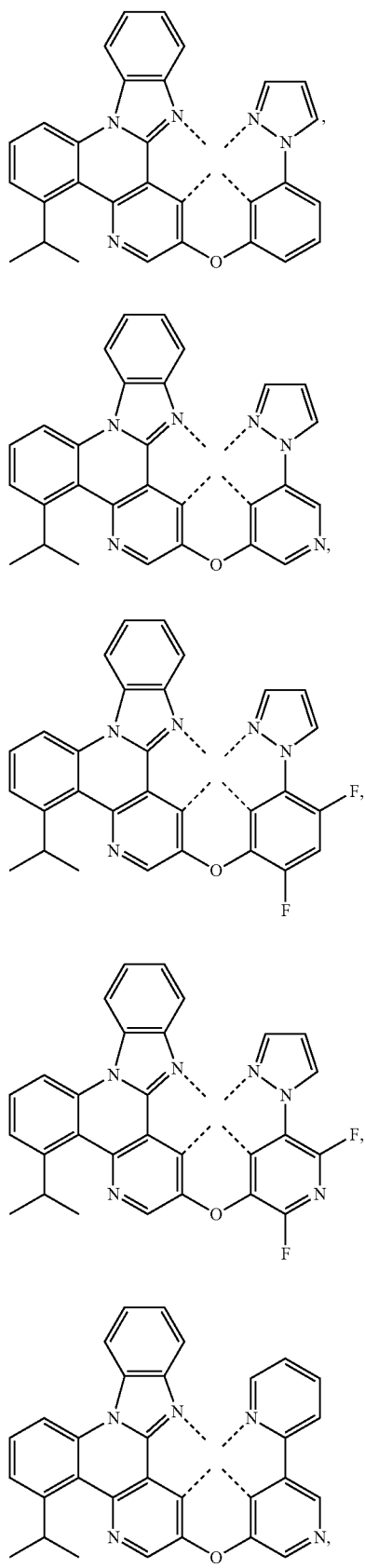
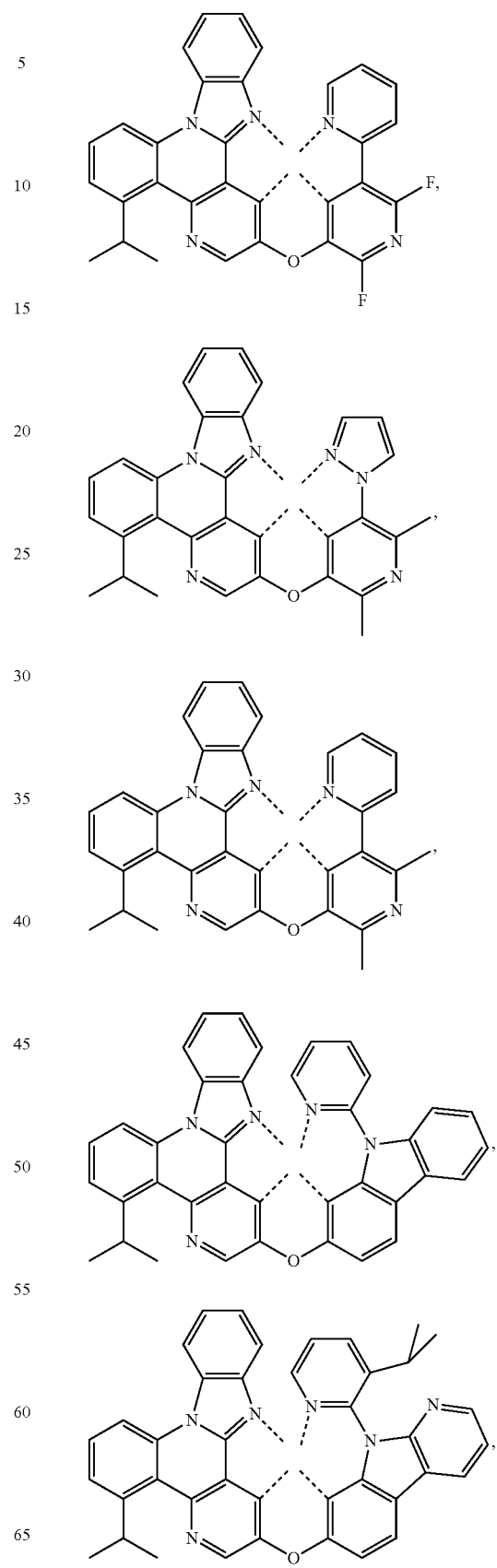

61
-continued
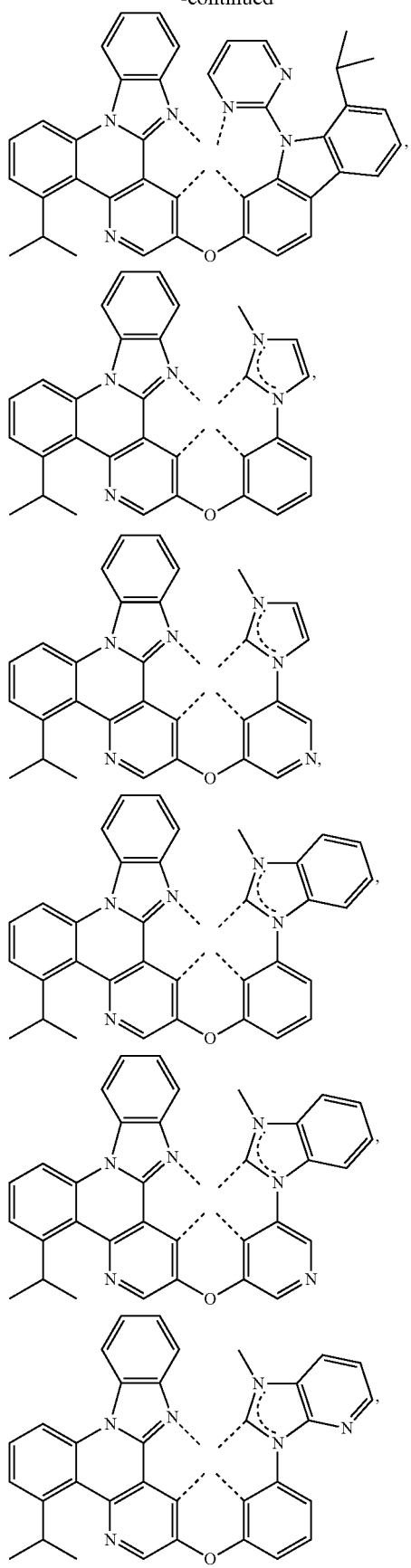
62
-continued
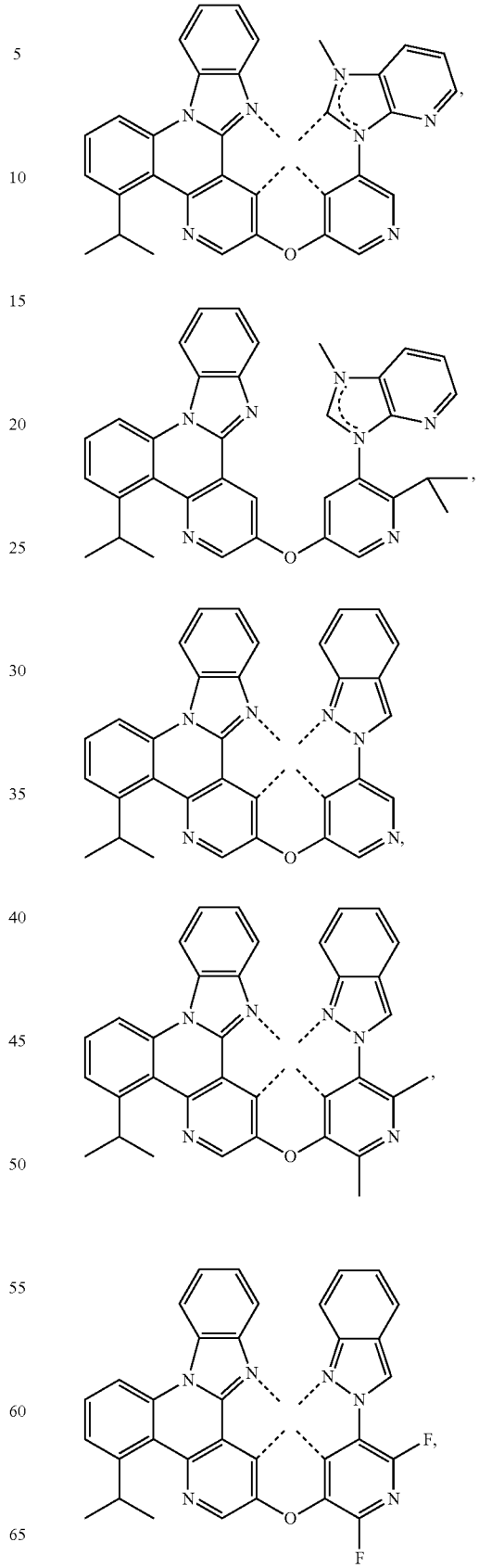

63
-continued
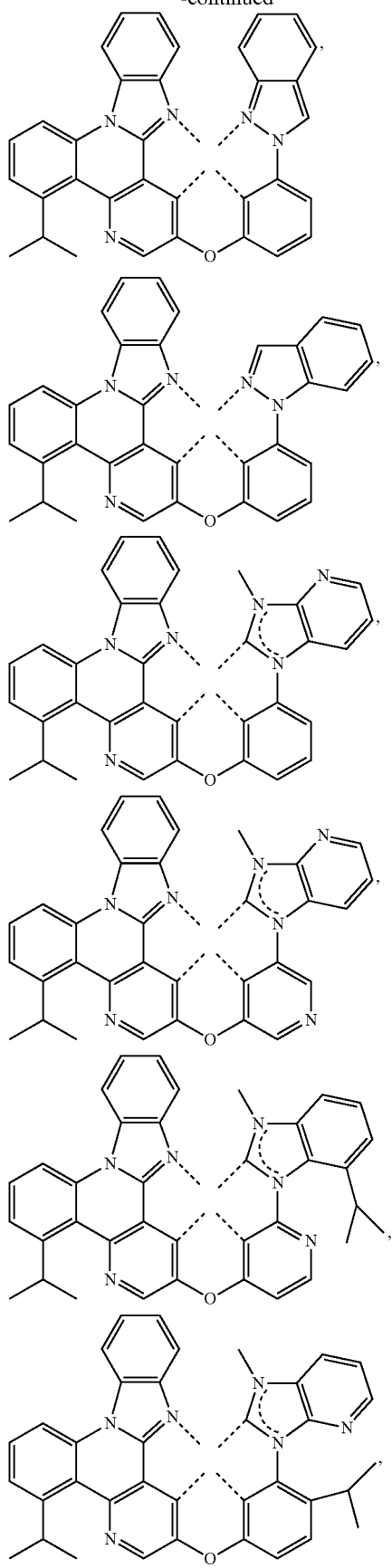
64
-continued
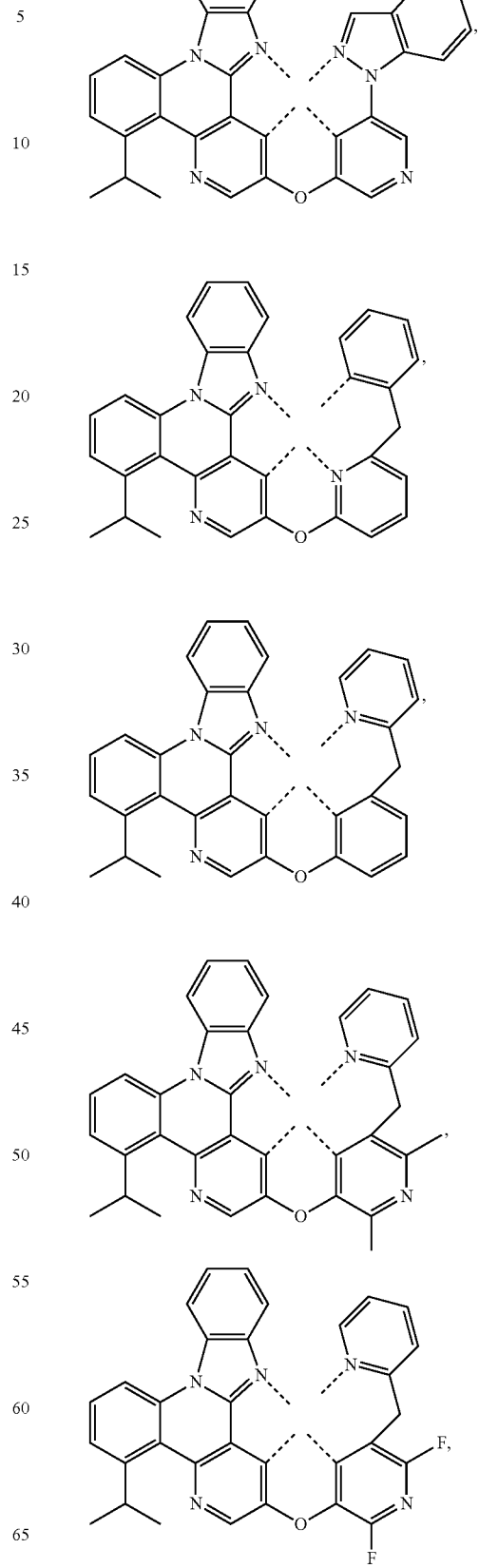

-continued

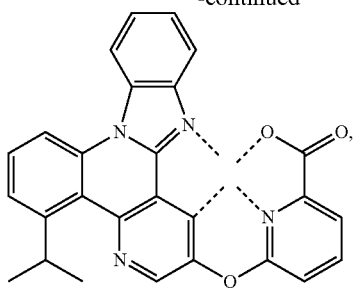

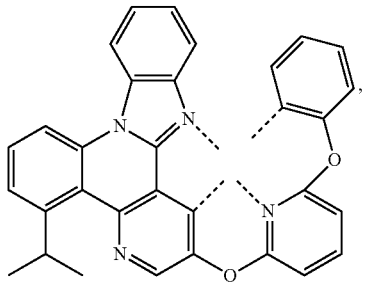

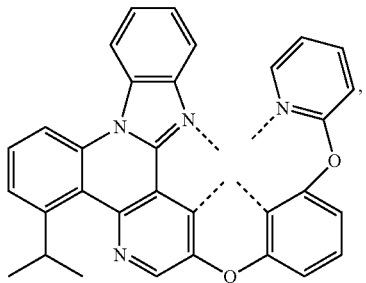

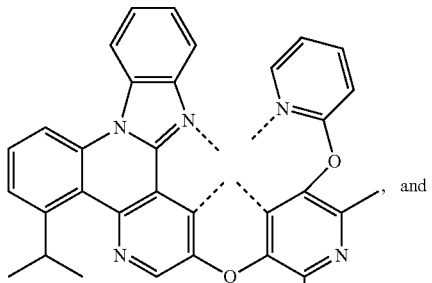, and

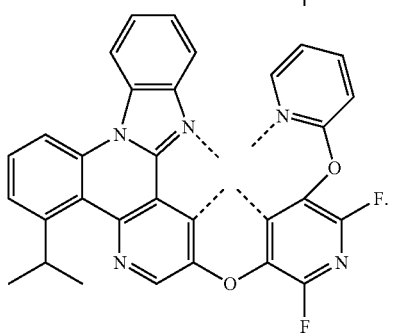

In some embodiments, the compound is homoleptic. A compound may be homoleptic when it comprises two or more ligands L, wherein the two or more ligands L are the same ligands. In other embodiments, the compound is heteroleptic. A compound may be heteroleptic when it comprises two or more ligands L, wherein at least one of the ligands L is a different ligand from the other ligands L. In some embodiments, the compound comprises at least one ligand L and at least one ligand L'. In one embodiment, L' is a different ligand from L. In another embodiment, L' is the same ligand as L. In another embodiment, L is selected from group A. L' is not particularly limited. In one embodiment, L' is a bidentate ligand. Additionally, ligands L' may be optionally substituted, and any adjacent substituents may be optionally fused or joined to form a ring or form a multidentate ligand. In some embodiments, L and L' are connected to form a multidentate ligand, such as a tridentate, tetradentate, pentadentate, or hexadentate ligand. In one embodiment, L and L' are connected to form a tetradentate ligand. L and L' may be connected at one location or place to form a multidentate ligand, or L and L' may be connected at two or more locations or places to form a macrocyclic multidentate ligand. In one embodiment, L and L' are connected at two places to form a macrocyclic tetradentate ligand.

In one embodiment, the compound has a formula of $Ir(L)_n(L')_{3-n}$;

wherein L' is selected from group A; and wherein n is 1, 2, or 3.

In one embodiment, n is 1. In another embodiment, n is 2. In another embodiment, n is 3.

In one embodiment, the compound has a formula of $Pt(L)_m(L')_{2-m}$;

wherein L' is selected from group A; and wherein m is 1, or 2.

In one embodiment, m is 1. In another embodiment, m is 2.

In one embodiment, the compound is selected from the group consisting of:

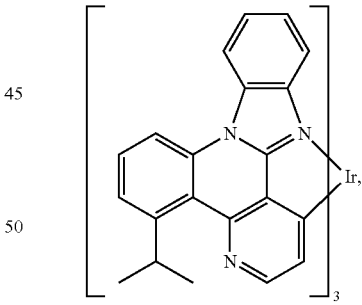

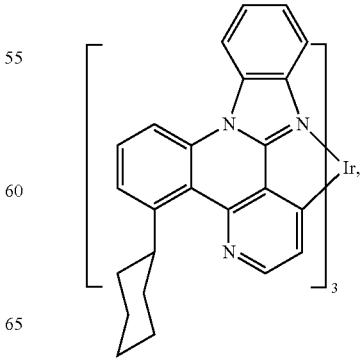

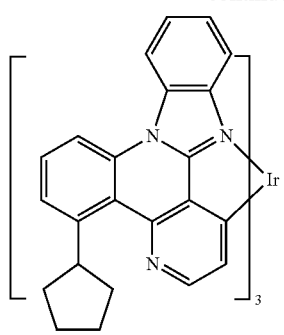
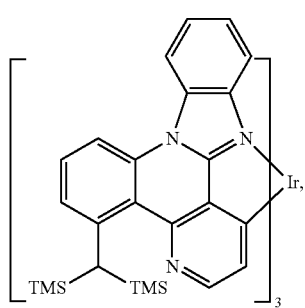
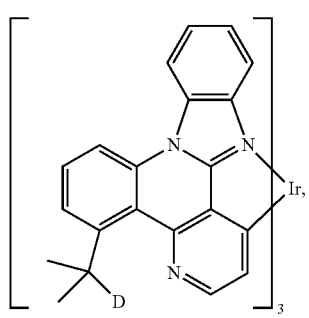
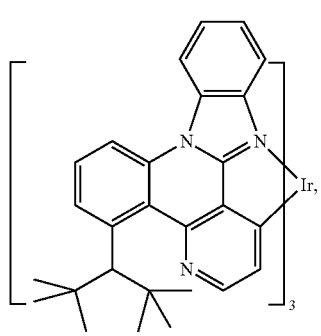
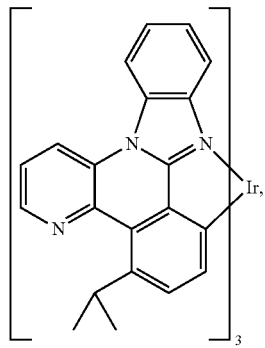
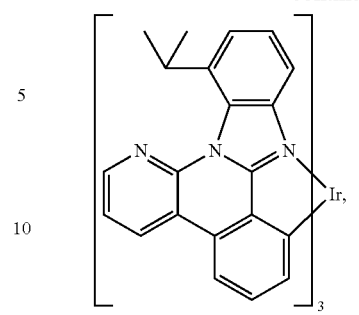
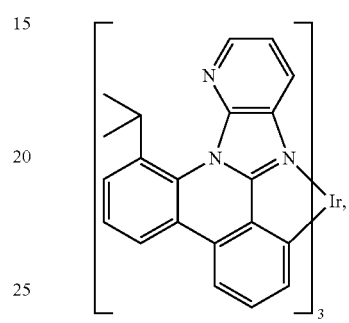
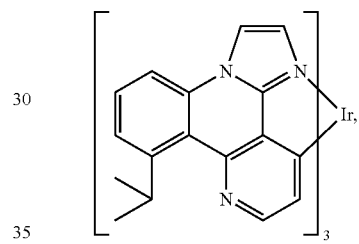
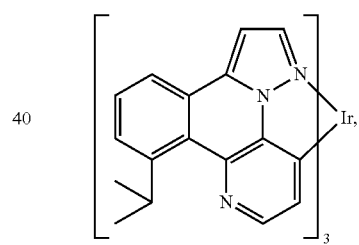
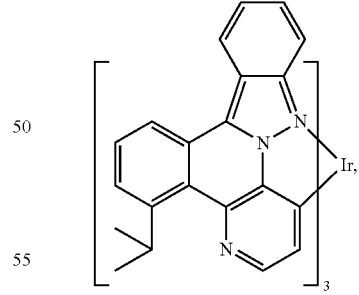
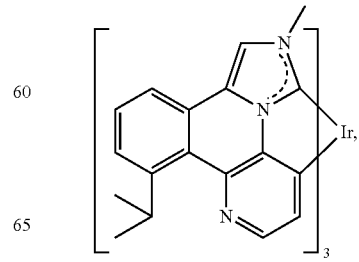

69
-continued
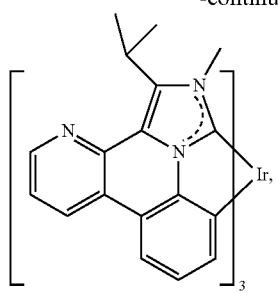
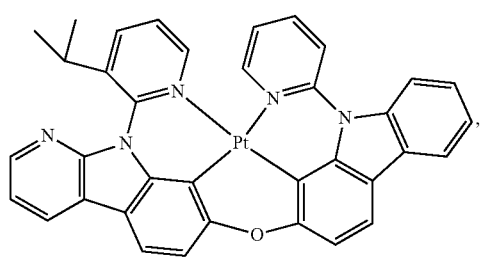
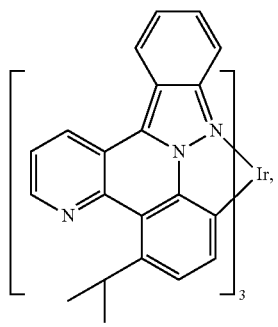
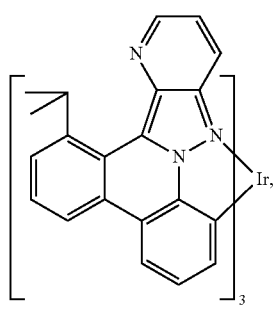
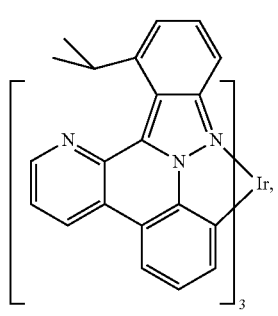
70
-continued
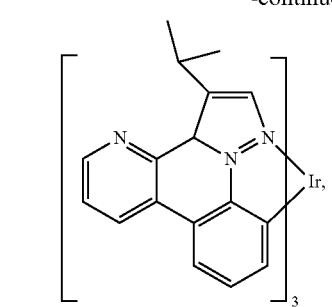
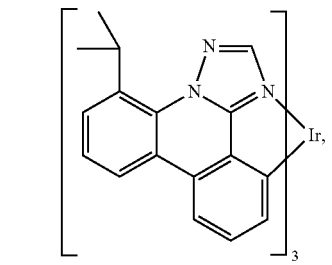
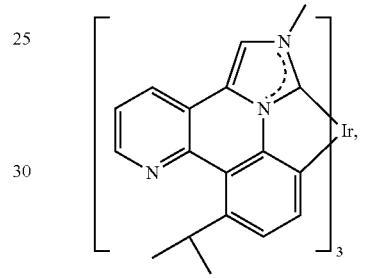
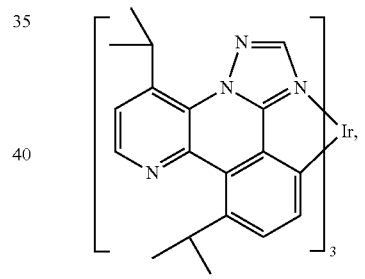
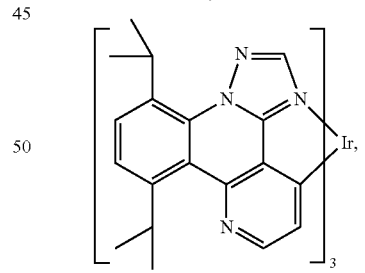
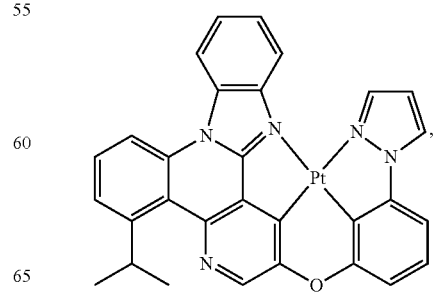

71
-continued
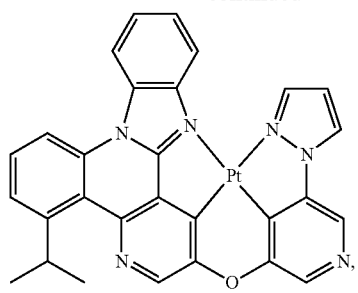
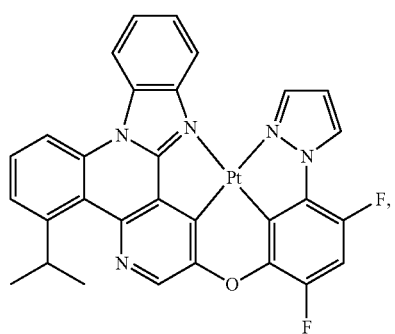
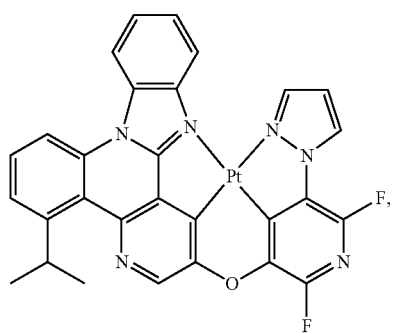
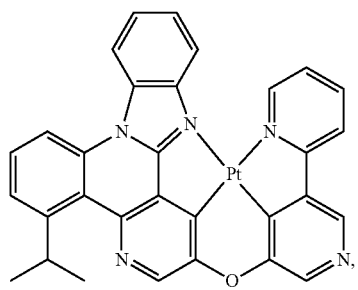
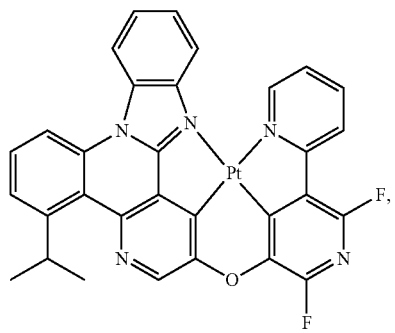
72
-continued
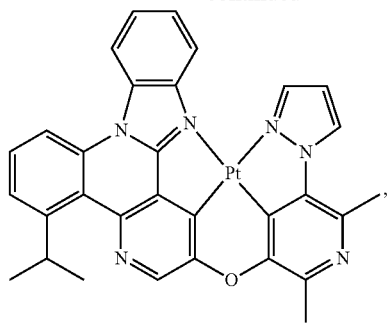
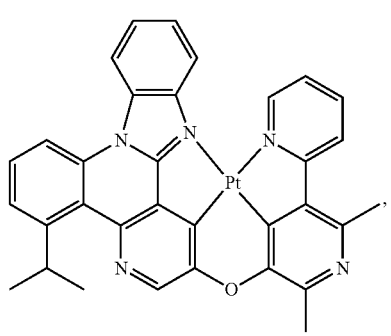
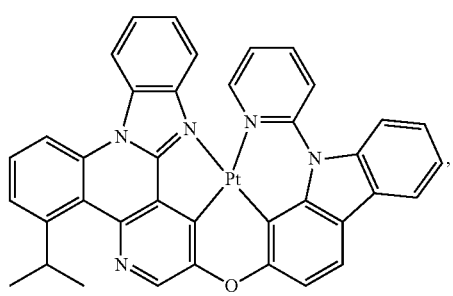
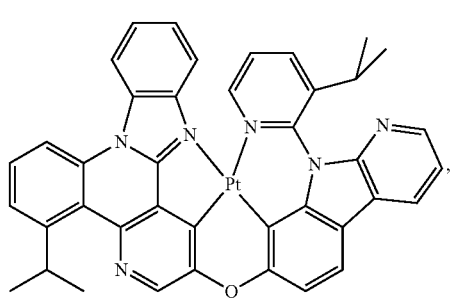
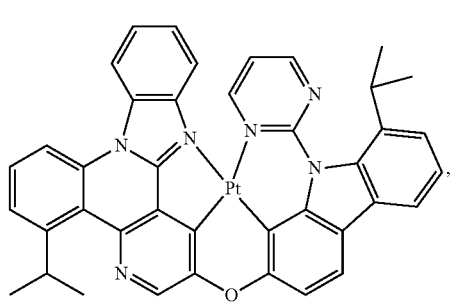

73
-continued
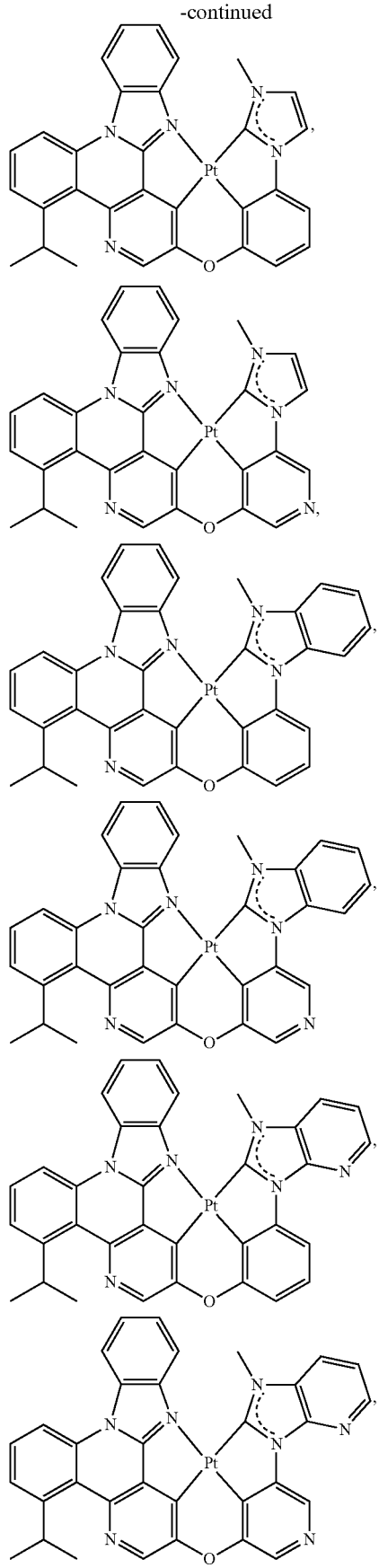
74
-continued
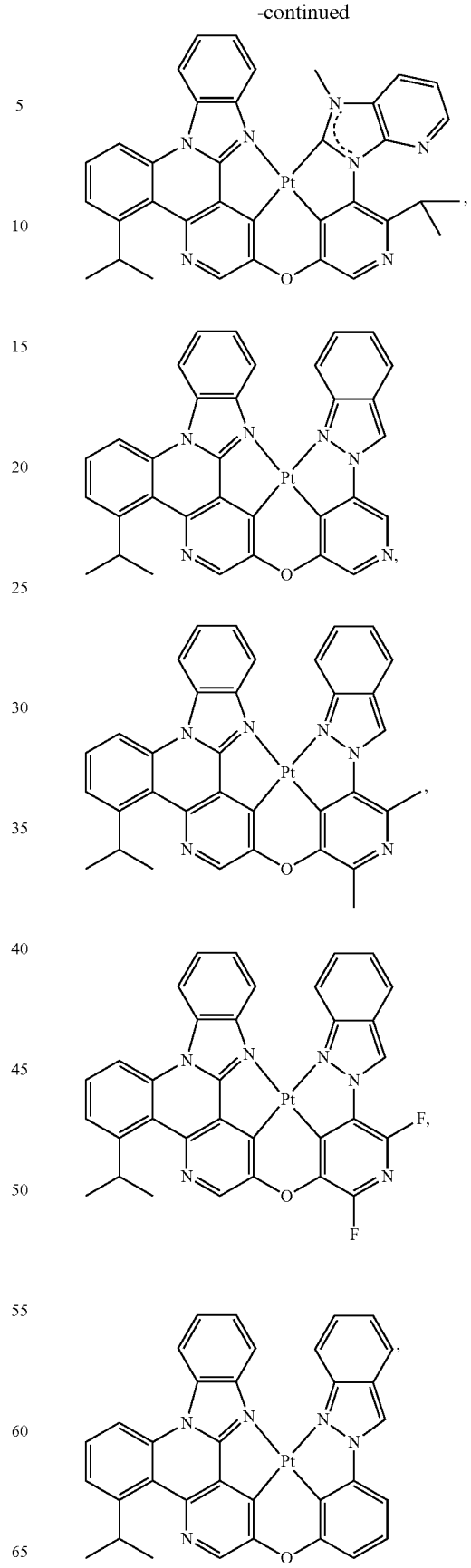

75
-continued
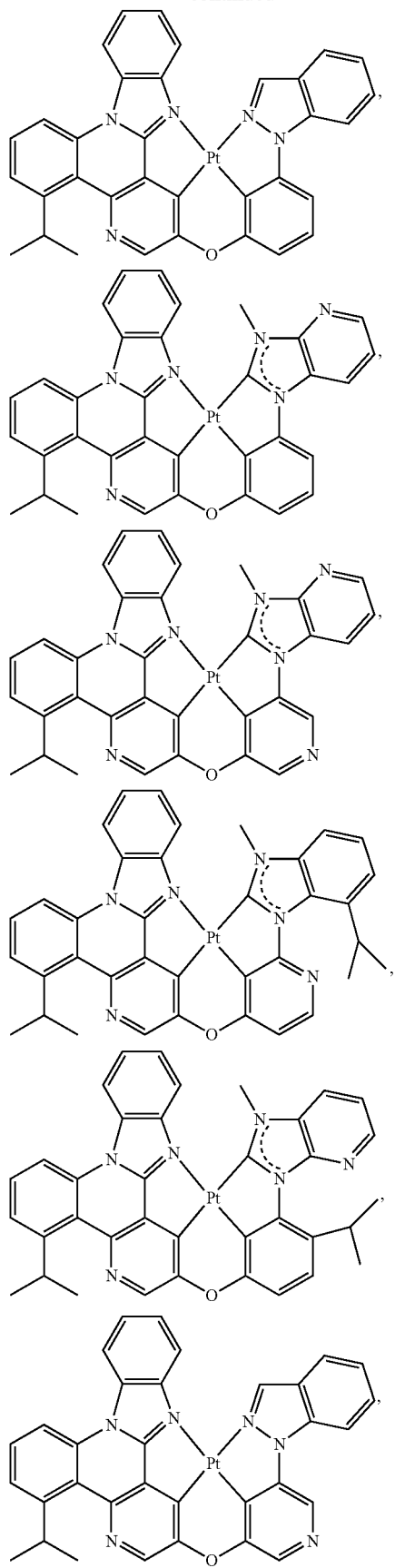
76
-continued
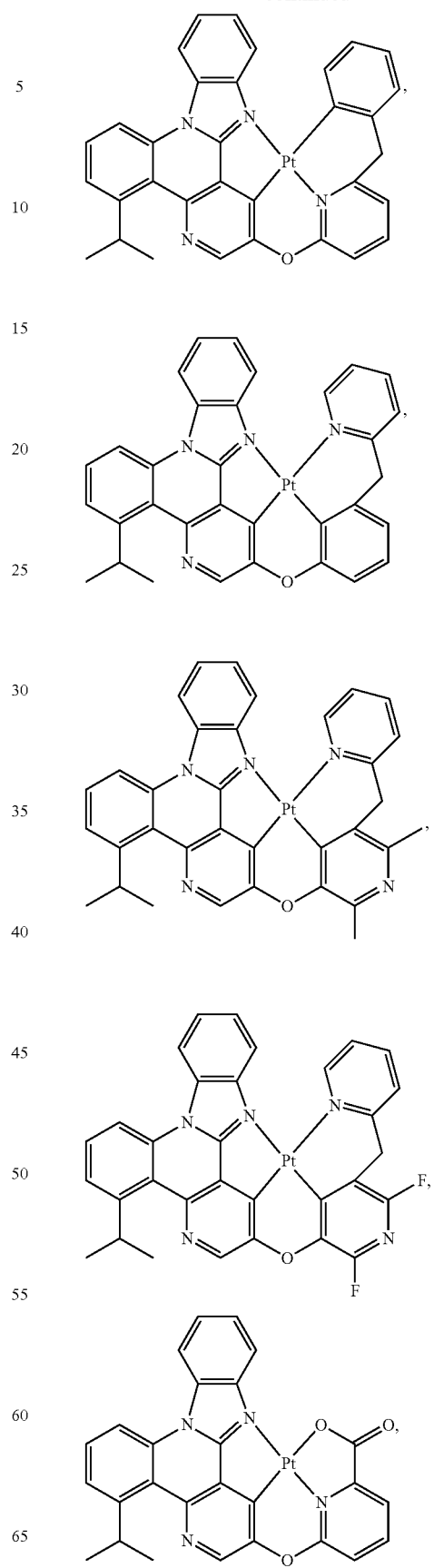

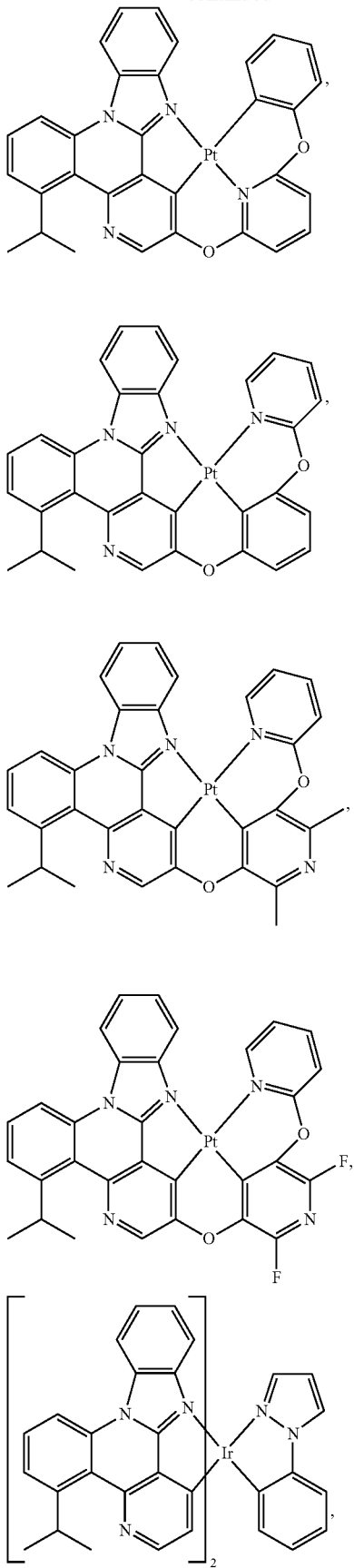

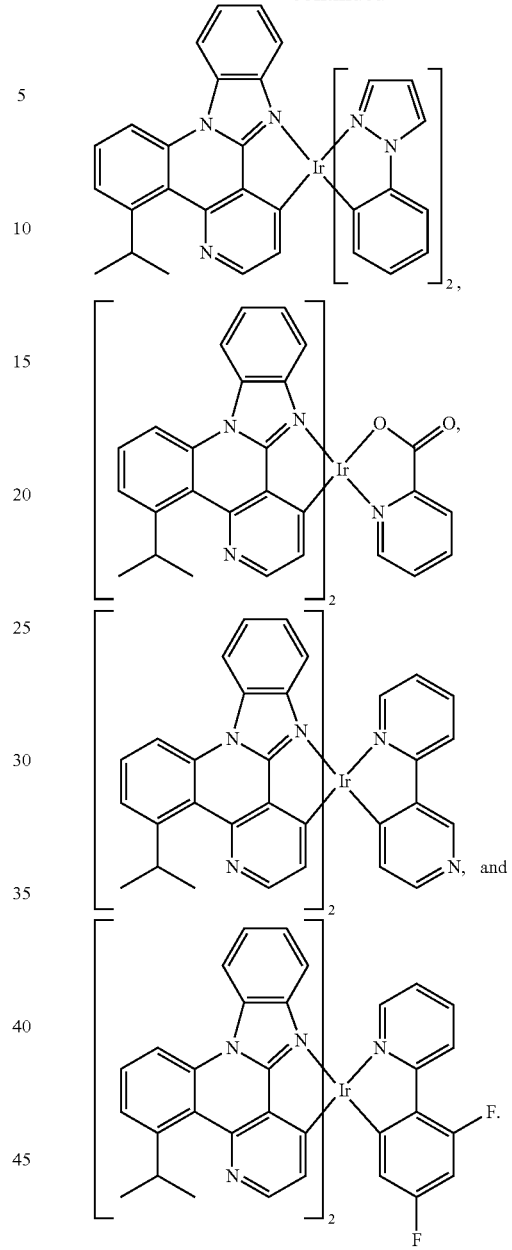

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Devices:

According to another aspect of the present disclosure, a first device is also provided. The first device includes a first organic light emitting device, that includes an anode, a cathode, and an organic layer disposed between the anode and the cathode. The organic layer may include a host and a phosphorescent dopant. The emissive layer can include a compound comprising a ligand L, and its variations as described herein.

The first device can be one or more of a consumer product, an electronic component module, an organic light-emitting device and a lighting panel. The organic layer can be an emissive layer and the compound can be an emissive dopant in some embodiments, while the compound can be a non-emissive dopant in other embodiments. The organic layer can be a charge transporting layer and the compound can be a charge transporting material in the organic layer in some embodiments. The organic layer can be a blocking layer and the compound can be a blocking material in the organic layer in some embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound comprising at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

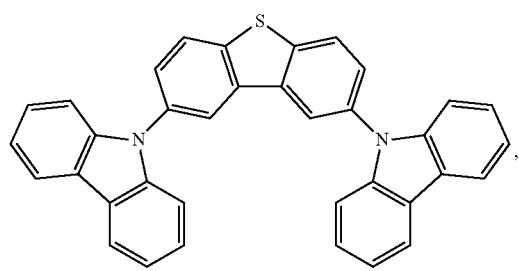

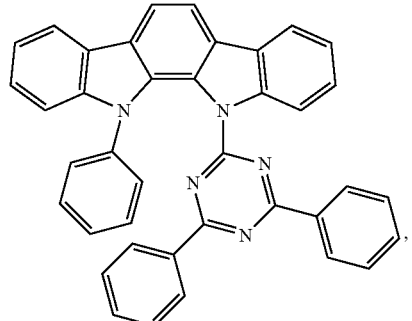

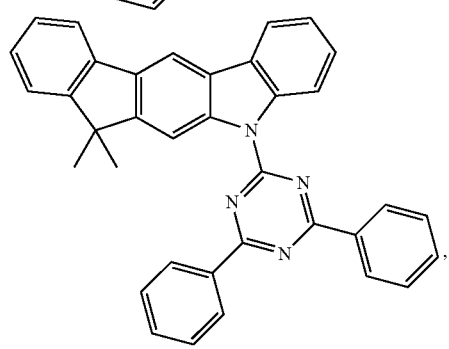

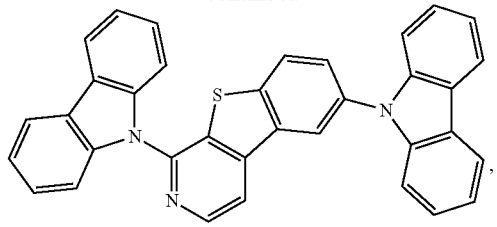

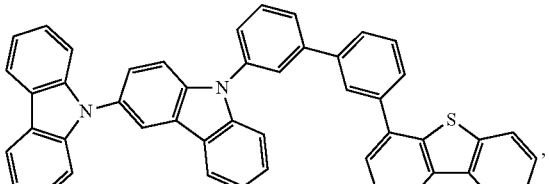

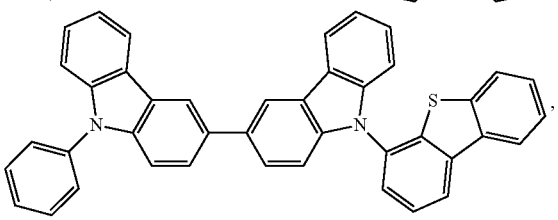

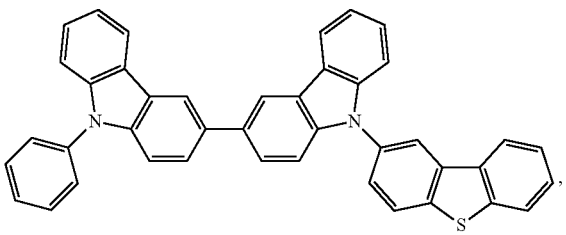

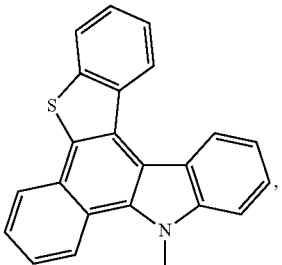

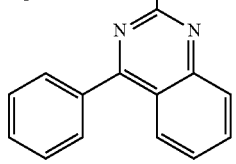

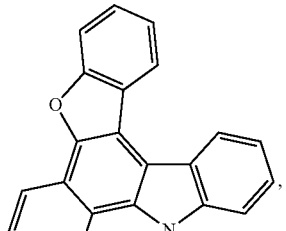

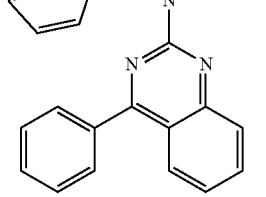

81
-continued
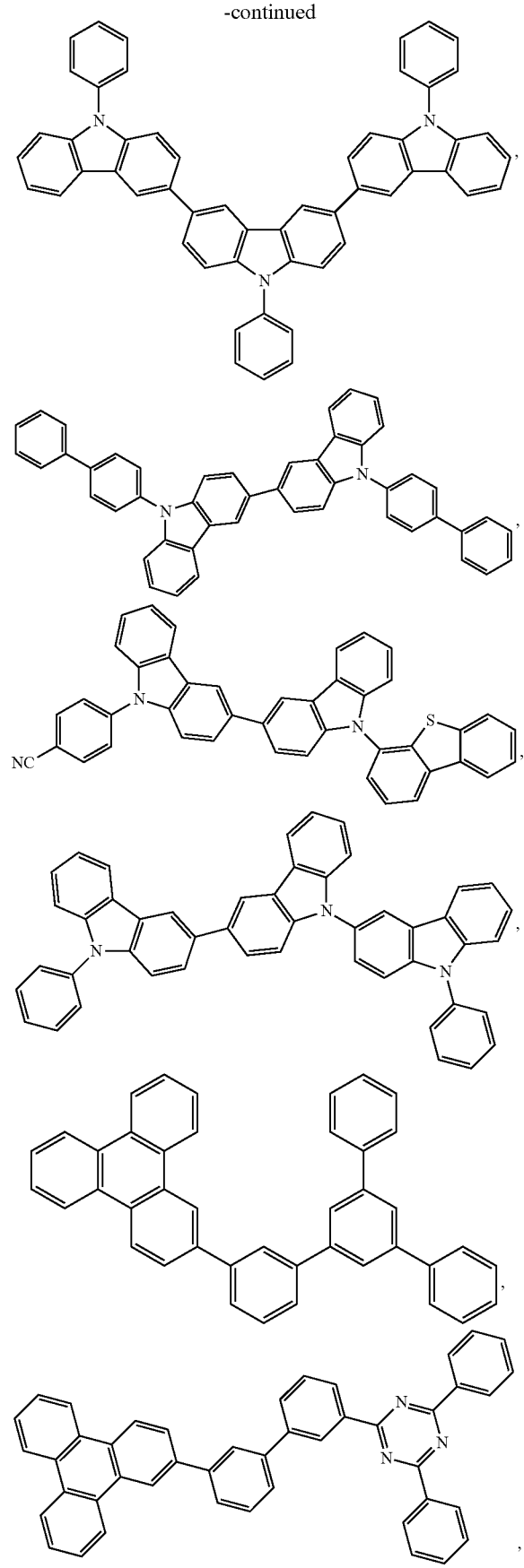
82
-continued
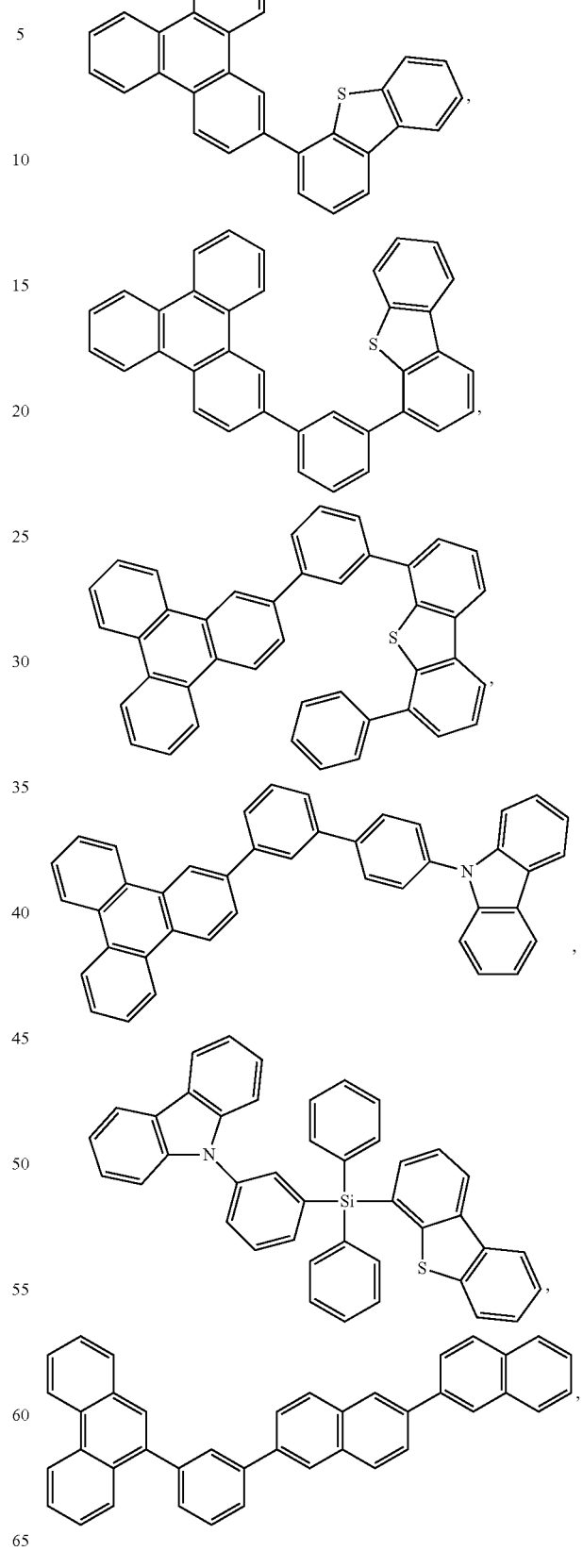
and combinations thereof.

Formulations:

In yet another aspect of the present disclosure, a formulation that comprises a compound comprising a ligand L is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and cross-linkable compounds.

Examples of aromatic amine derivatives used in HIL or HTL include, but are not limited to the following general structures:

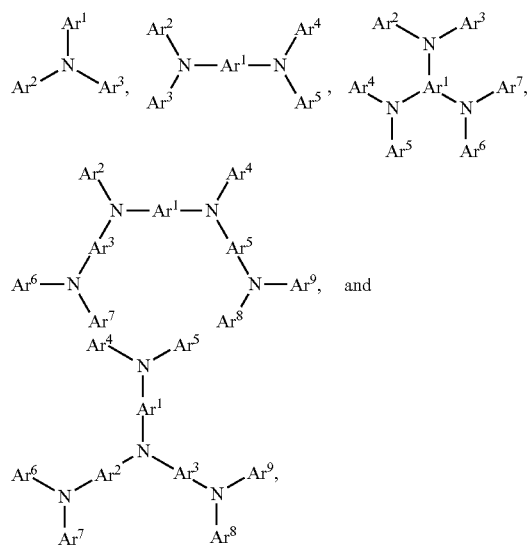

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

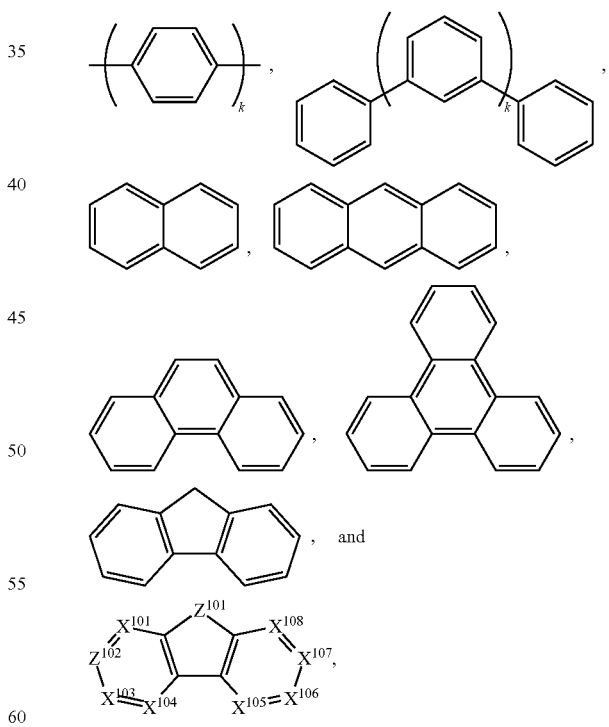

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

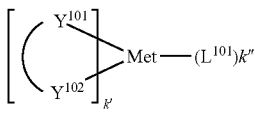

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc+/Fc couple less than about 0.6 V. Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

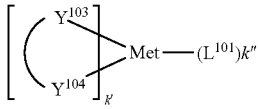

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

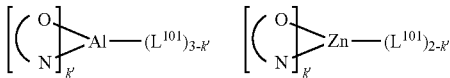

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

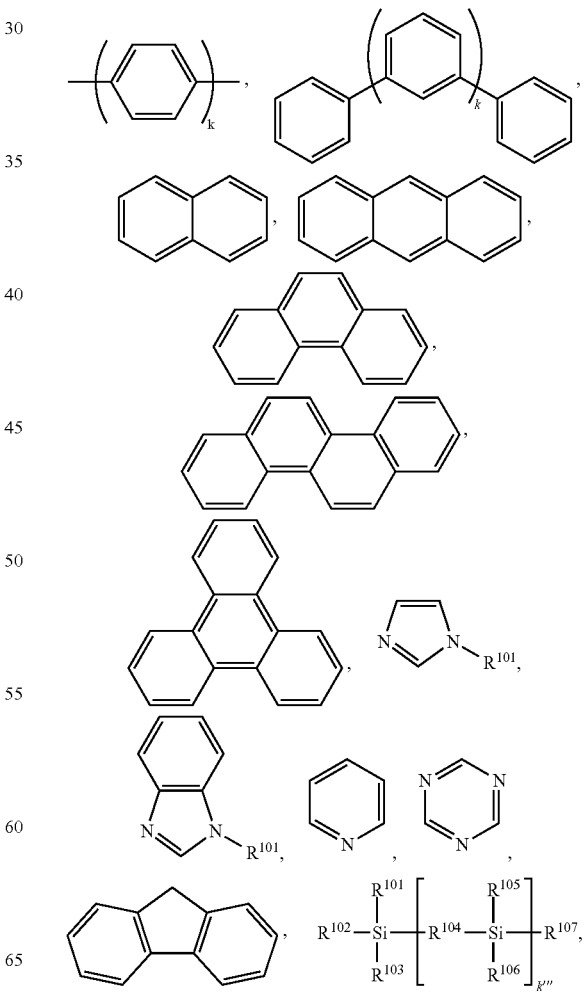

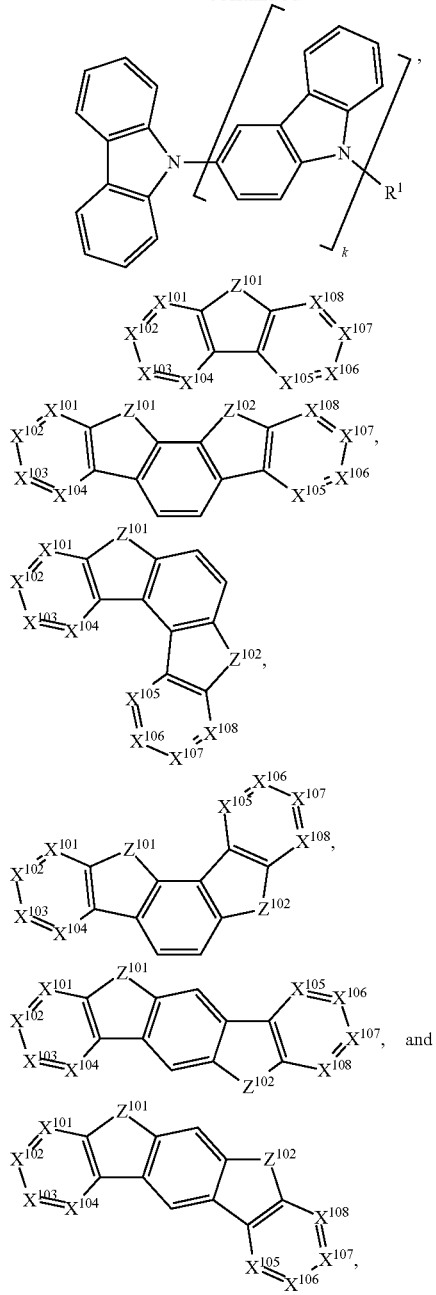

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule or the same functional groups used as the host described above.

In another aspect, the compound used in the HBL contains at least one of the following groups in the molecule:

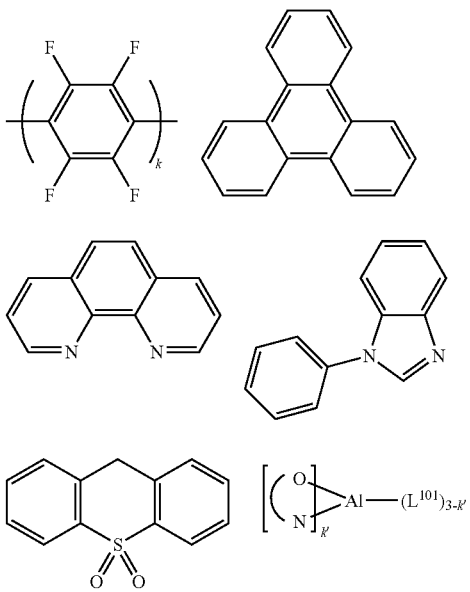

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, the compound used in ETL contains at least one of the following groups in the molecule:

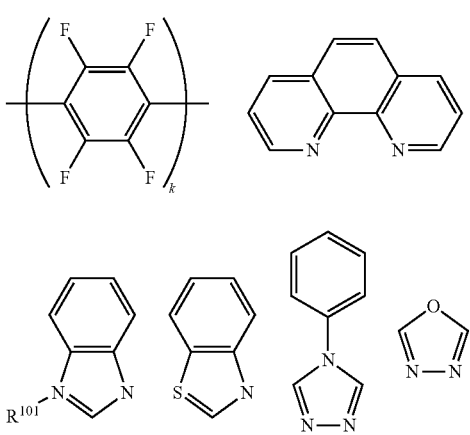

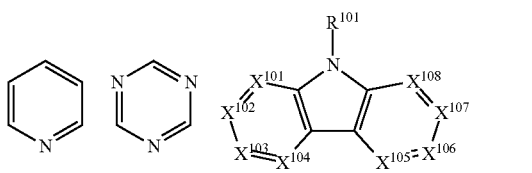

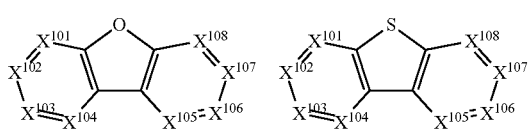

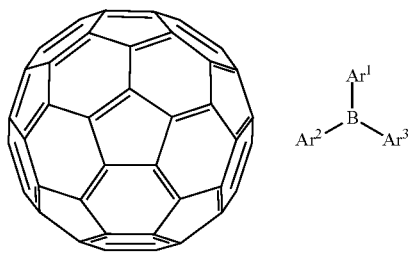

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but is not limited to, the following general formula:

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| | Hole injection materials | |
| Phthalocyanine and porphyrin compounds | | Appl. Phys. Lett. 26, 2160 (1996) |

TABLE A-continued

| MATERIAL | EXAMPLES OF MATERIAL | PUBLICATIONS |
|---|---|---|
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |
| Triarylamine or polythiophene polymers with conductivity dopants | and | EP1725079A1 |

TABLE A-continued
| MATERIAL | EXAMPLES OF MATERIAL | PUBLICATIONS |
|---|---|---|
| | 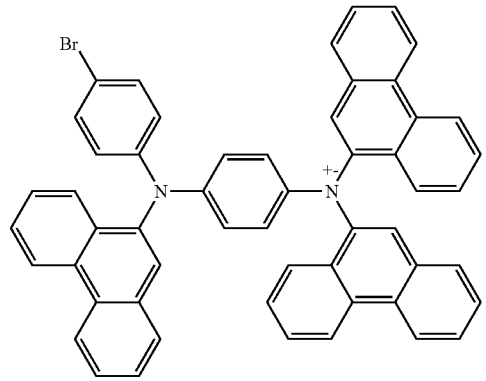 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 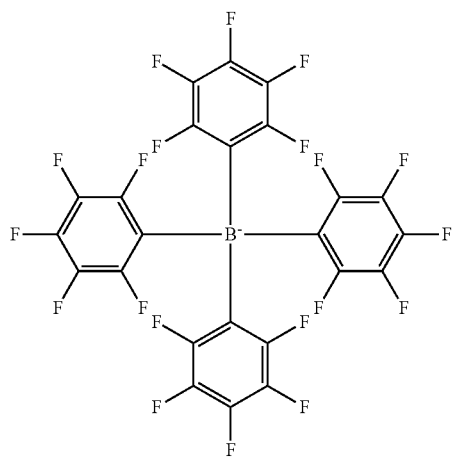 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 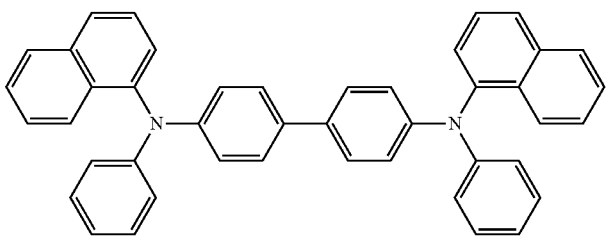 + MoO$_x$ | US20050123751 SID Symposium Digest, 37, 923 (2006) WO2009018009 |
| n-type semiconducting organic complexes | 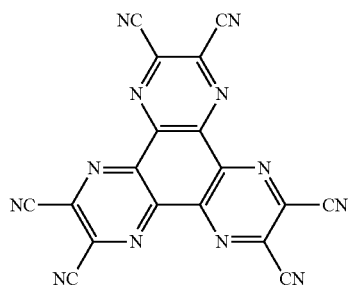 [SMILES: N#Cc1nc2c3nc(C#N)c(C#N)nc3c3nc(C#N)c(C#N)nc3c2nc1C#N] | US20020158242 |

TABLE A-continued
| MATERIAL | EXAMPLES OF MATERIAL | PUBLICATIONS |
|---|---|---|
| Metal organometallic complexes | 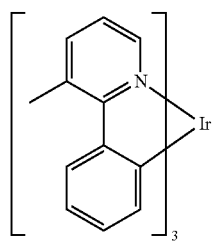 | US20060240279 |
| Crosslinkable compounds | 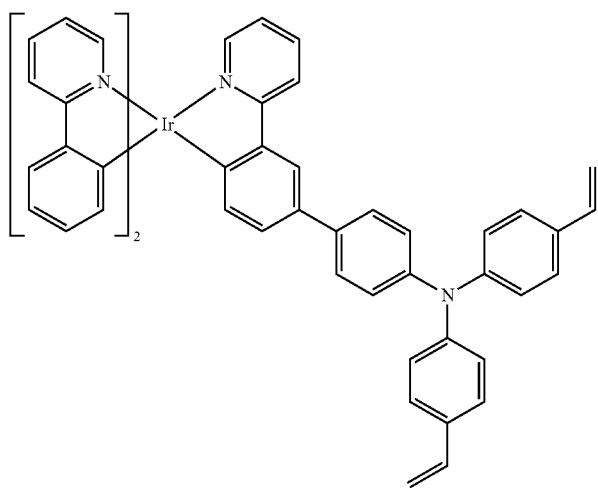 | US20080220265 |
| Polythiophene based polymers and copolymers | 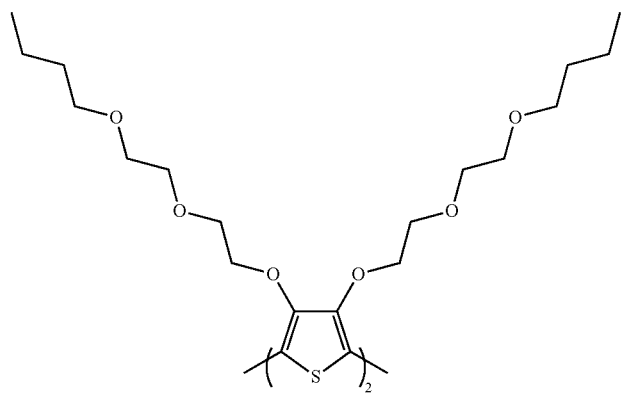 | WO 2011075644<br>EP2350216 |
Hole transporting materials
| | | |
|---|---|---|
| Triarylamines (e.g., TPD, α-NPD) | 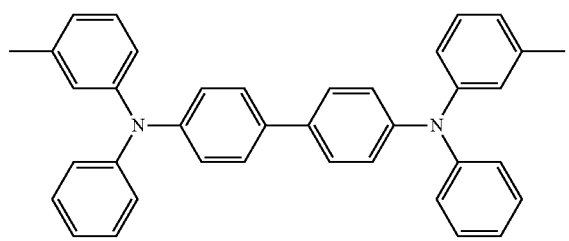 | Appl. Phys. Lett. 51, 913 (1987) |

TABLE A-continued
| MATERIAL | EXAMPLES OF MATERIAL | PUBLICATIONS |
|---|---|---|
| | 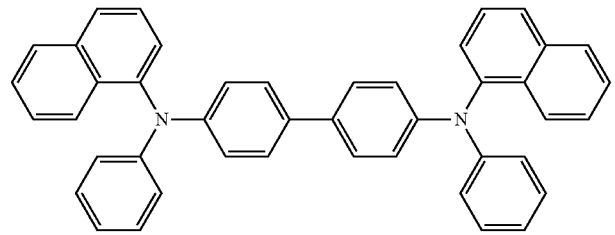 [SMILES: c1ccc(N(c2ccc(-c3ccc(N(c4ccccc4)c4cccc5ccccc45)cc3)cc2)c2cccc3ccccc23)cc1] | US5061569 |
| | 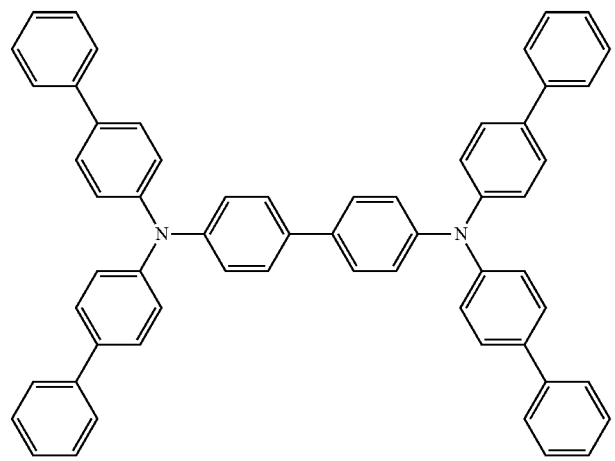 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 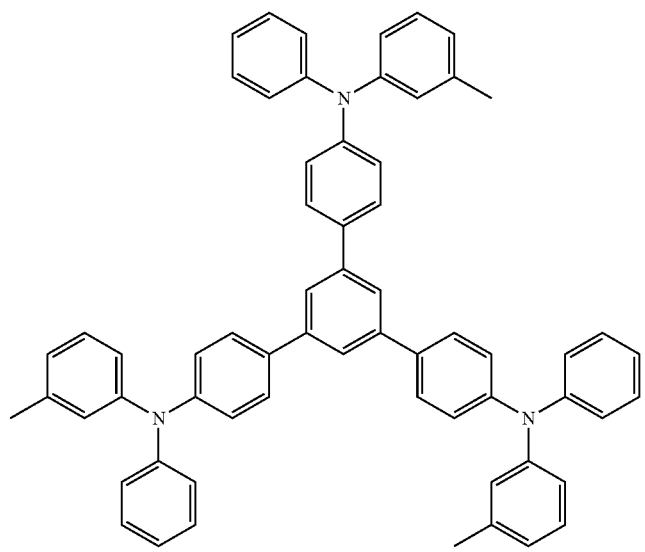 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued
| MATERIAL | EXAMPLES OF MATERIAL | PUBLICATIONS |
|---|---|---|
| | 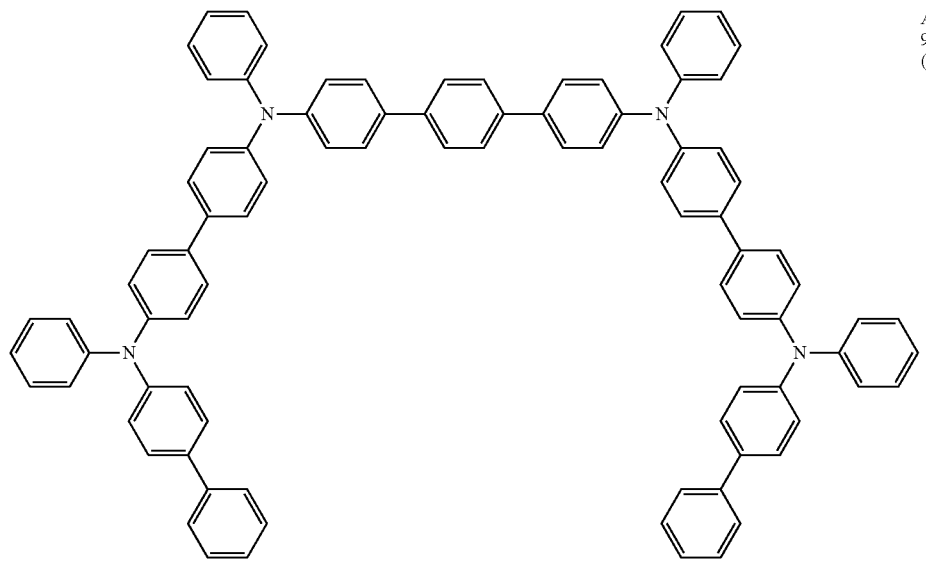 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 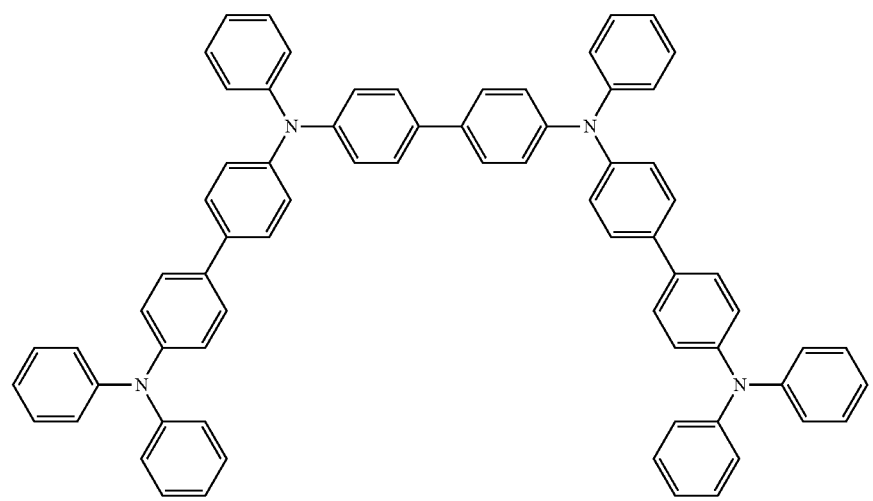 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 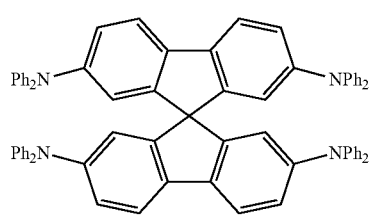 | Synth. Met. 91, 209 (1997) |

TABLE A-continued
| MATERIAL | EXAMPLES OF MATERIAL | PUBLICATIONS |
|---|---|---|
| Arylamine carbazole compounds | 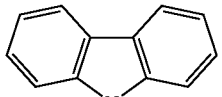 | Adv. Mater. 6, 677 (1994), US20080124572 |
| Triarylamine with (di)benzothiophene/ (di)benzofuran | 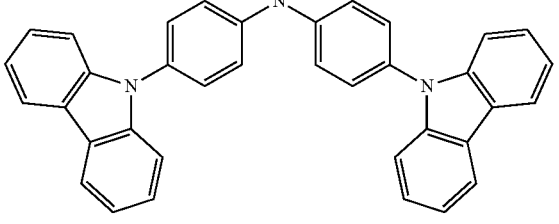 | US20070278938, US20080106190 US20110163302 |
| Indolocarbazoles | 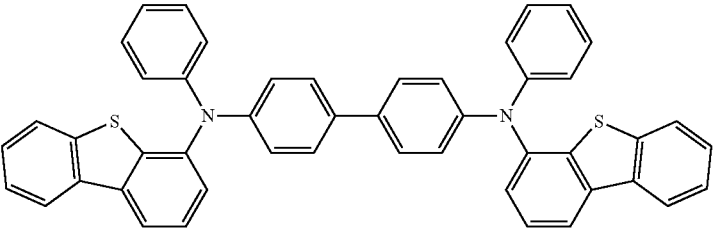 [SMILES: c1ccc(N(c2ccc(-c3ccc(N(c4ccccc4)c4cccc5c4sc4ccccc45)cc3)cc2)c2cccc3c2sc2ccccc23)cc1] | Synth. Met. 111, 421 (2000) |
| Isoindole compounds | 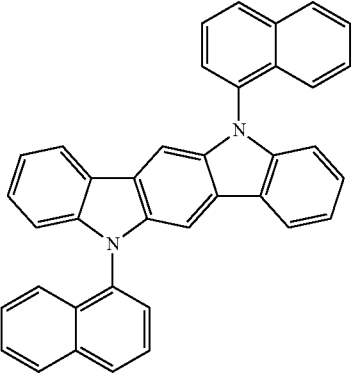 [SMILES: c1ccc2c(-n3c4ccccc4c4cc5c(cc43)c3ccccc3n5-c3cccc4ccccc34)cccc2c1] | Chem. Mater. 15, 3148 (2003) |

| MATERIAL | EXAMPLES OF MATERIAL | PUBLICATIONS |
|---|---|---|
| Metal carbene complexes | 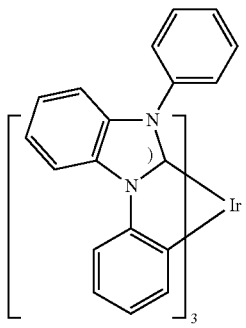 | US20080018221 |
Phosphorescent OLED host materials
| | | |
|---|---|---|
| Red hosts | | |
| Aryl-carbazoles | 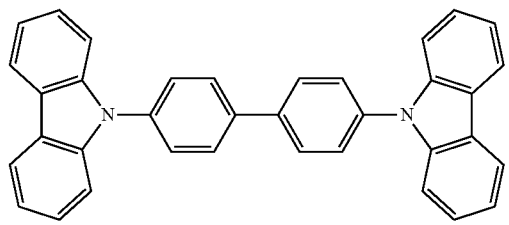 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 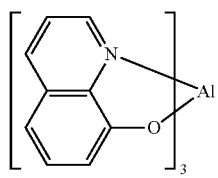 | Nature 395, 151 (1998) |
| | 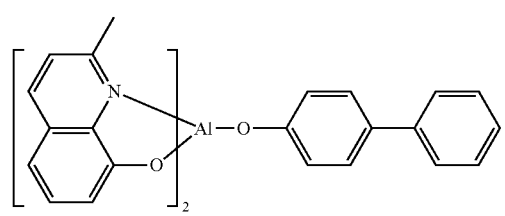 | US20060202194 |
| | 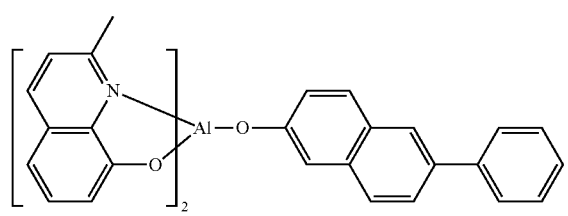 | WO2005014551 |
| | 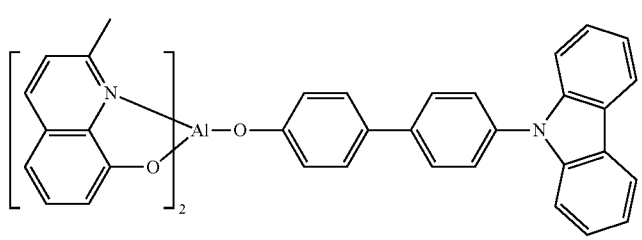 | WO2006072002 |

TABLE A-continued

| MATERIAL | EXAMPLES OF MATERIAL | PUBLICATIONS |
|---|---|---|
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Green hosts | | |
| Arylcarbazoles | | Appl. Phys. Lett. 78, 1622 (2001) |

TABLE A-continued

| MATERIAL | EXAMPLES OF MATERIAL | PUBLICATIONS |
|---|---|---|
| | | US20030175553 |
| | | WO2001039234 |
| Aryltriphenylene compounds | | US20060280965 |
| | | US20060280965 |
| | | WO2009021126 |

TABLE A-continued
| MATERIAL | EXAMPLES OF MATERIAL | PUBLICATIONS |
|---|---|---|
| Polyfused heteroaryl compounds | 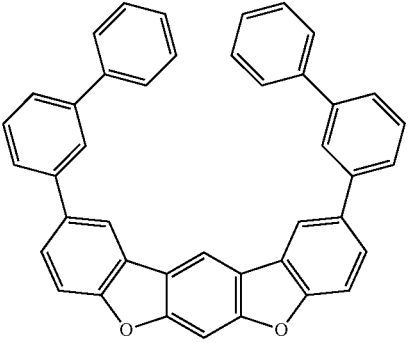 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 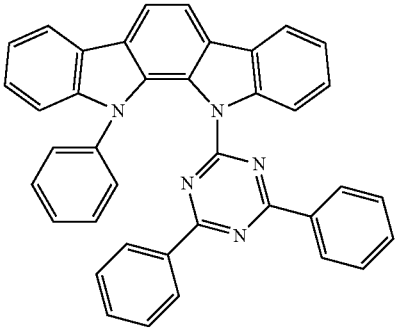 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 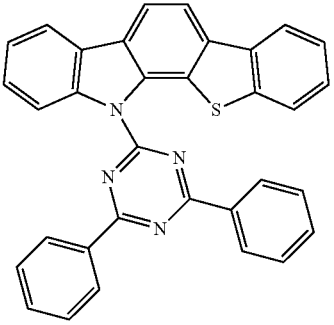 [SMILES: c1ccc(-c2nc(-c3ccccc3)nc(-n3c4ccccc4c4ccc5c6ccccc6sc5c43)n2)cc1] | WO2010107244 |
| Azacarbazole/DBT/DBF | 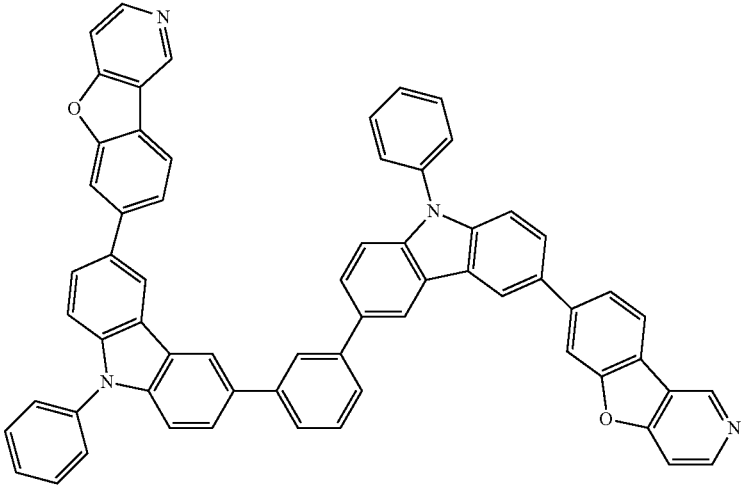 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE A-continued

| MATERIAL | EXAMPLES OF MATERIAL | PUBLICATIONS |
|---|---|---|
| | | US20100187984 |
| Polymers (e.g., PVK) | | Appl. Phys. Lett. 77, 2280 (2000) |
| Spiro-fluorene compounds | | WO2004093207 |
| Metal phenoxy benzooxazole compounds | | WO2005089025 |
| | | WO2006132173 |
| | | JP200511610 |

TABLE A-continued
| MATERIAL | EXAMPLES OF MATERIAL | PUBLICATIONS |
|---|---|---|
| Spiro-fluorene-carbazole compounds | 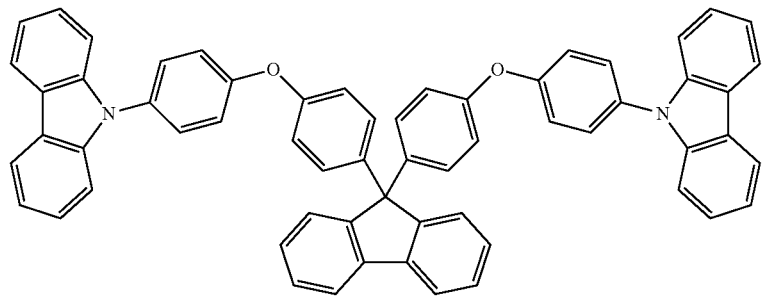 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
|  | 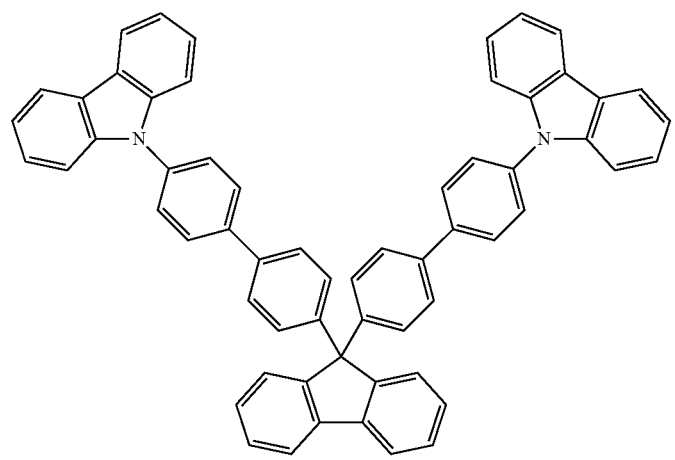 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Idolo-carbazoles | 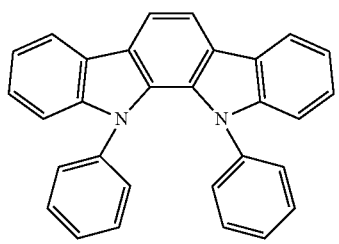 [SMILES: c1ccc(-n2c3ccccc3c3ccc4c5ccccc5n(-c5ccccc5)c4c32)cc1] | WO2007063796 |
|  | 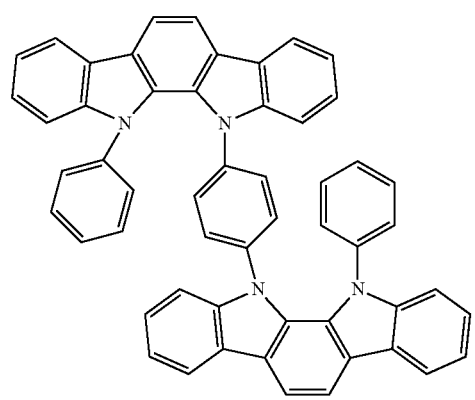 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |

TABLE A-continued
| MATERIAL | EXAMPLES OF MATERIAL | PUBLICATIONS |
|---|---|---|
| 5-member ring electron deficient heterocycles (e.g., triazole, oxadiazole) | 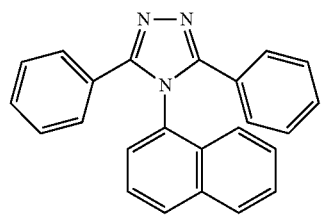 [SMILES: c1ccc(-c2nnc(-c3ccccc3)n2-c2cccc3ccccc23)cc1] | J. Appl. Phys. 90, 5048 (2001) |
|  | 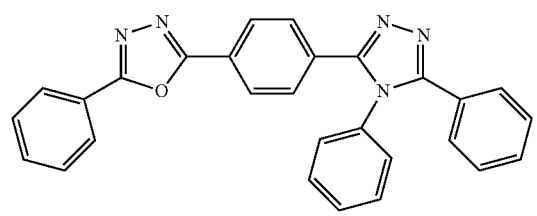 [SMILES: c1ccc(-c2nnc(-c3ccc(-c4nnc(-c5ccccc5)n4-c4ccccc4)cc3)o2)cc1] | WO2004107822 |
| Tetraphenylene complexes | 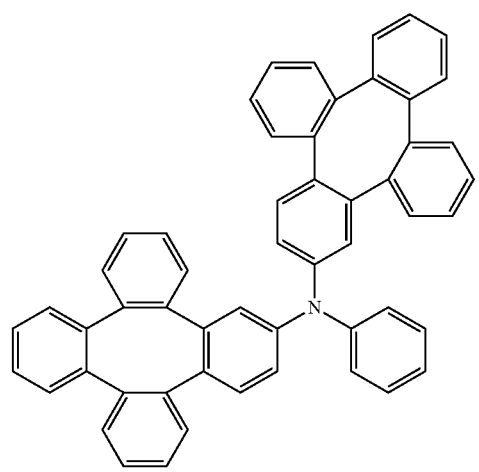 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 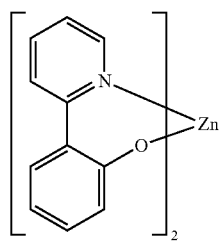 | WO2005030900 |
| Metal coordination complexes (e.g., Zn, Al with N^N ligands) | 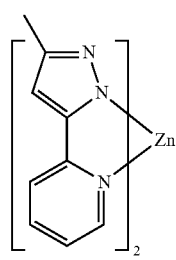 | US20040137268, US20040137267 |

TABLE A-continued
| MATERIAL | EXAMPLES OF MATERIAL | PUBLICATIONS |
|---|---|---|
| Blue hosts | | |
| Arylcarbazoles | 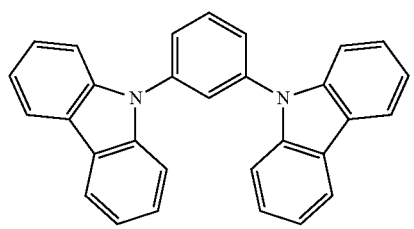 [SMILES: c1cc(-n2c3ccccc3c3ccccc32)cc(-n2c3ccccc3c3ccccc32)c1] | Appl. Phys. Lett, 82, 2422 (2003) |
| | 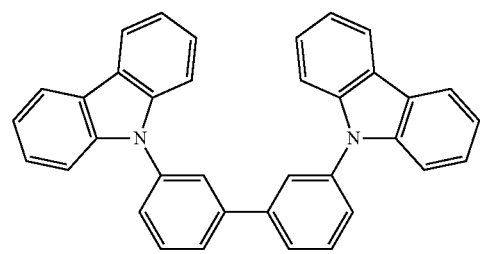 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofurancarbazole compounds | 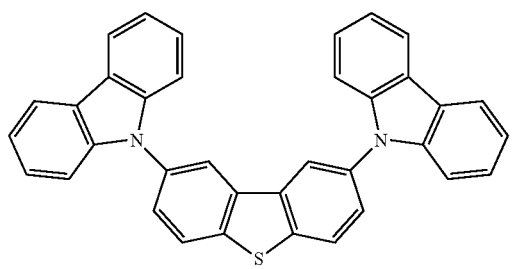 [SMILES: c1ccc2c(c1)c1ccccc1n2-c1ccc2sc3ccc(-n4c5ccccc5c5ccccc54)cc3c2c1] | WO2006114966, US20090167162 |
| | 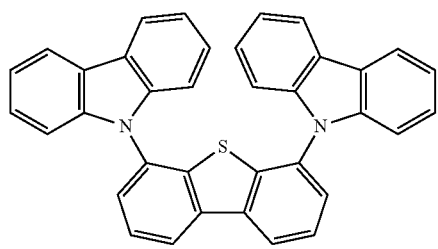 [SMILES: c1cc(-n2c3ccccc3c3ccccc32)c2sc3c(-n4c5ccccc5c5ccccc54)cccc3c2c1] | US20090167162 |
| | 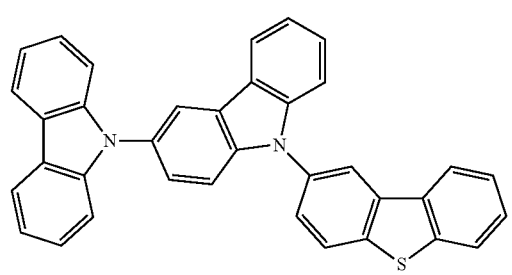 [SMILES: c1ccc2c(c1)sc1ccc(-n3c4ccccc4c4cc(-n5c6ccccc6c6ccccc65)ccc43)cc12] | WO2009086028 |

TABLE A-continued

| MATERIAL | EXAMPLES OF MATERIAL | PUBLICATIONS |
|---|---|---|
| | | US20090030202, US20090017330 |
| | | US20100084966 |
| Silicon aryl compounds | | US20050238919 |
| | | WO2009003898 |
| Silicon/Germanium aryl compounds | | EP2034538A |
| Aryl benzoyl ester | | WO2006100298 |

TABLE A-continued
| MATERIAL | EXAMPLES OF MATERIAL | PUBLICATIONS |
|---|---|---|
| Carbazole linked by non-conjugated groups | 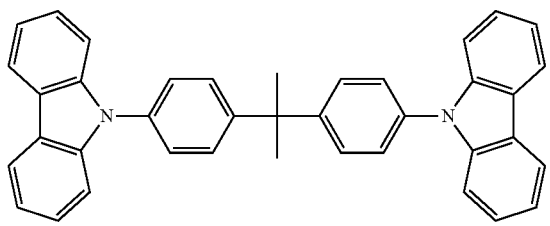 [SMILES: CC(C)(c1ccc(-n2c3ccccc3c3ccccc32)cc1)c1ccc(-n2c3ccccc3c3ccccc32)cc1] | US20040115476 |
| Azacarbazoles | 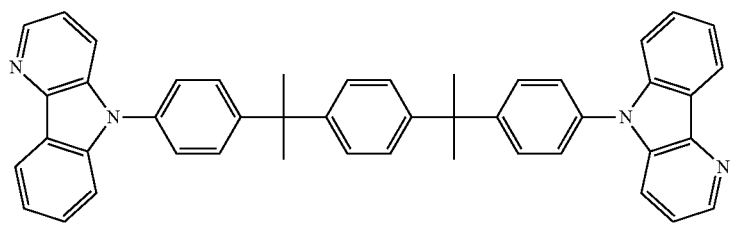 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 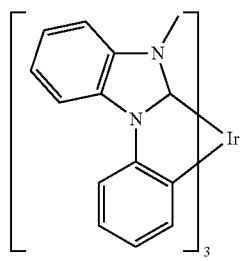 | US7154114 |
Phosphorescent dopants
Red dopants
| Heavy metal porphyrins (e.g., PtOEP) | 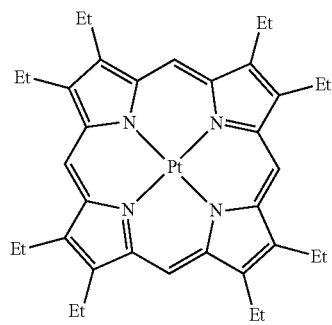 | Nature 395, 151 (1998) |
|---|---|---|
| Iridium (III) organometallic complexes | 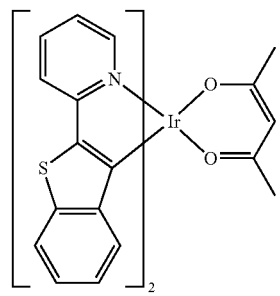 | Appl. Phys. Lett. 78, 1622 (2001) |

TABLE A-continued
| MATERIAL | EXAMPLES OF MATERIAL | PUBLICATIONS |
|---|---|---|
| | 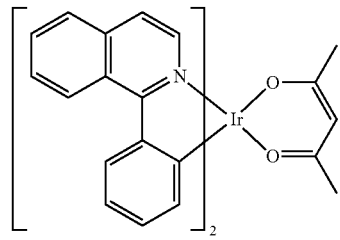 | US20030072964 |
| | 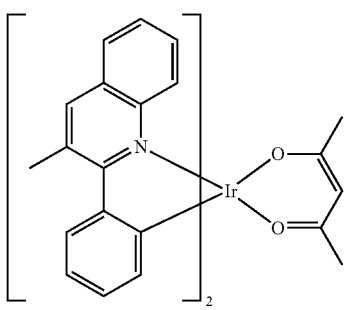 | US20030072964 |
| | 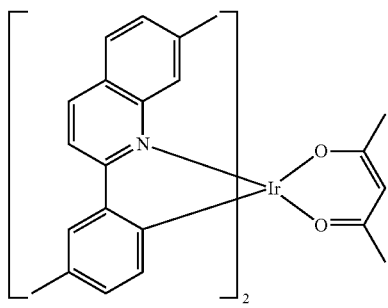 | US20060202194 |
| | 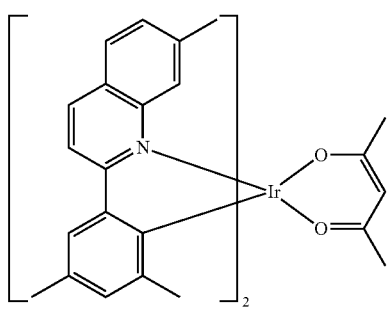 | US20060202194 |
| | 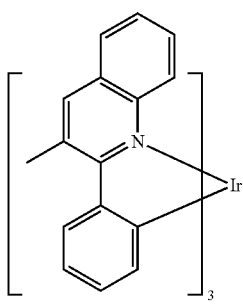 | US20070087321 |

TABLE A-continued
| MATERIAL | EXAMPLES OF MATERIAL | PUBLICATIONS |
|---|---|---|
| | 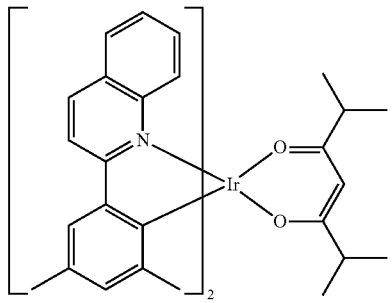 | US20080261076<br>US20100090591 |
| | 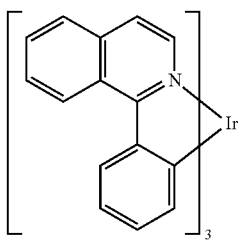 | US20070087321 |
| | 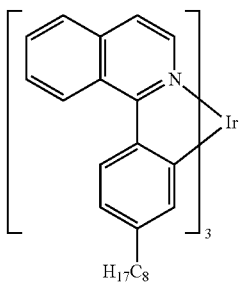 | Adv. Mater.<br>19, 739<br>(2007) |
| | 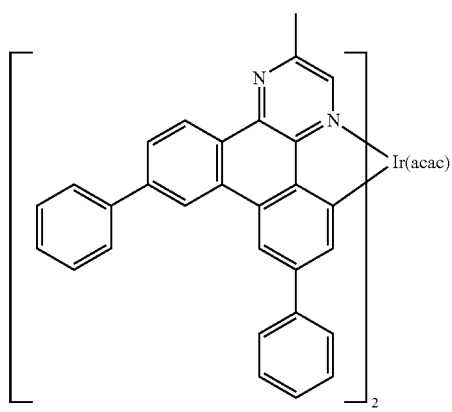 | WO2009100991 |
| | 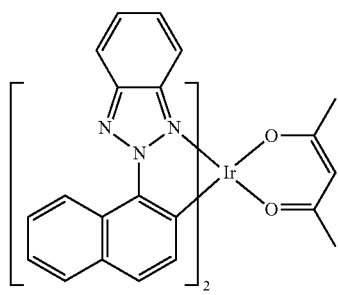 | WO2008101842 |

TABLE A-continued
| MATERIAL | EXAMPLES OF MATERIAL | PUBLICATIONS |
|---|---|---|
| | 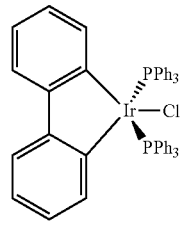 | US7232618 |
| Platinum (II) organometallic complexes | 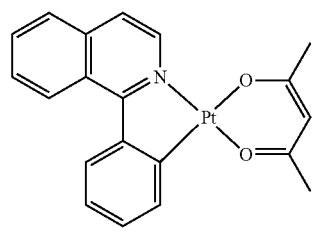 | WO2003040257 |
| | 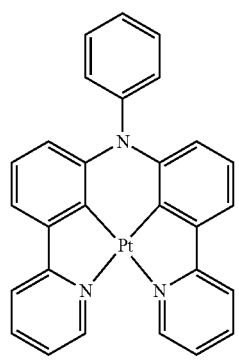 | US20070103060 |
| Osmium (III) complexes | 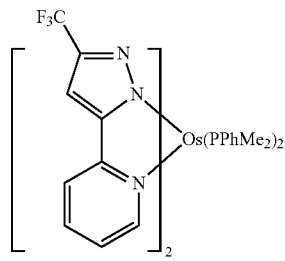 | Chem. Mater. 17, 3532 (2005) |
| Ruthenium (II) complexes | 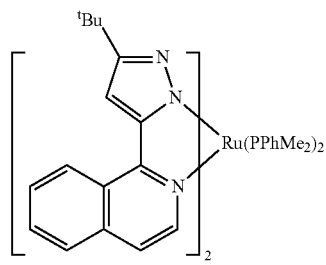 | Adv. Mater. 17, 1059 (2005) |
| Rhenium (I), (II), and (III) complexes | 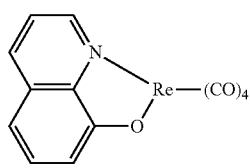 | US20050244673 |

TABLE A-continued
| MATERIAL | EXAMPLES OF MATERIAL | PUBLICATIONS |
|---|---|---|
| Green dopants | | |
| Iridium(III) organometallic complexes | 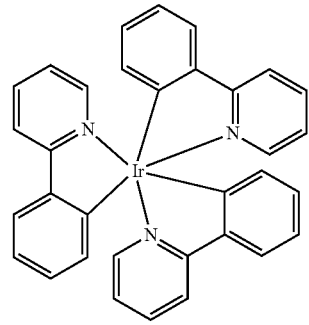<br>and its derivatives | Inorg. Chem. 40, 1704 (2001) |
| | 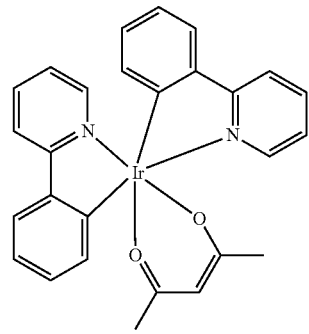 | US20020034656 |
| | 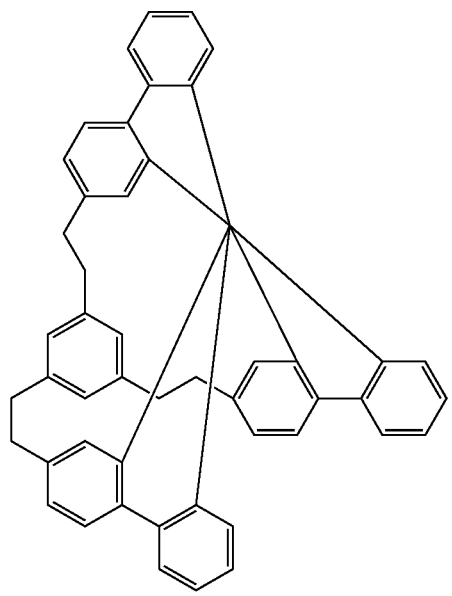 | US7332232 |

TABLE A-continued
| MATERIAL | EXAMPLES OF MATERIAL | PUBLICATIONS |
|---|---|---|
| | 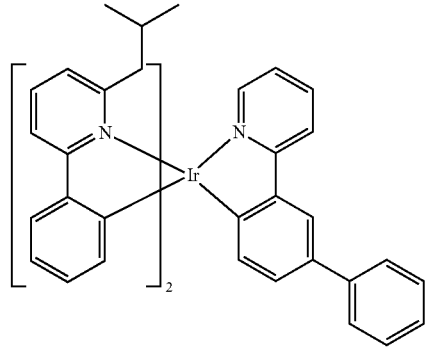 | US20090108737 |
| | 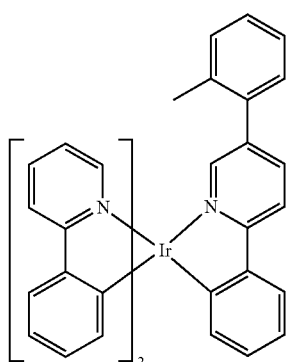 | WO2010028151 |
| | 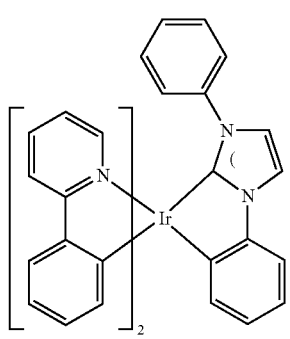 | EP1841834B |
| | 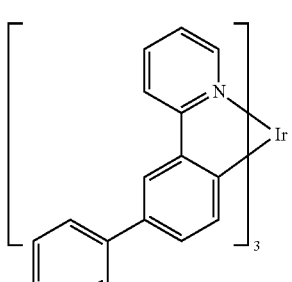 | US20060127696 |

TABLE A-continued
| MATERIAL | EXAMPLES OF MATERIAL | PUBLICATIONS |
|---|---|---|
| | 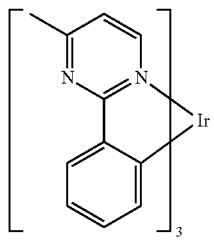 | US20090039776 |
| | 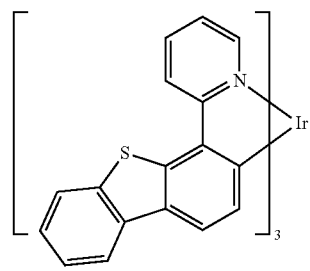 | US6921915 |
| | 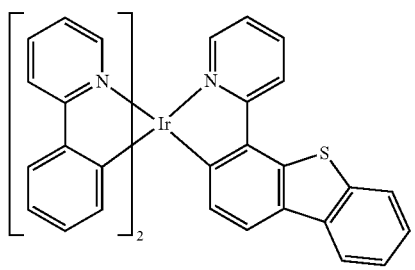 | US20100244004 |
| | 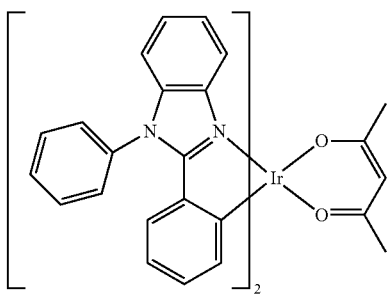 | US6687266 |
| | 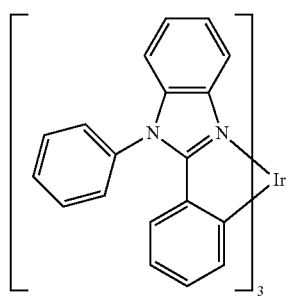 | Chem. Mater. 16, 2480 (2004) |

TABLE A-continued
| MATERIAL | EXAMPLES OF MATERIAL | PUBLICATIONS |
|---|---|---|
| | 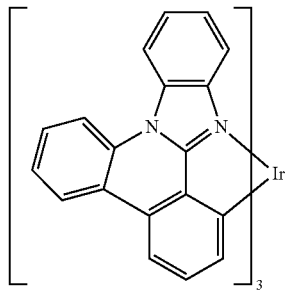 | US20070190359 |
| | 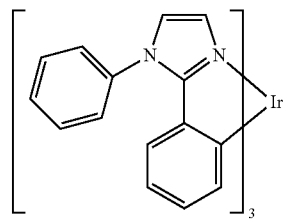 | US 20060008670 JP2007123392 |
| | 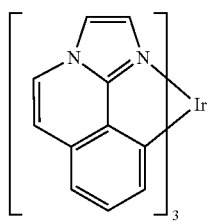 | WO2010086089, WO2011044988 |
| | 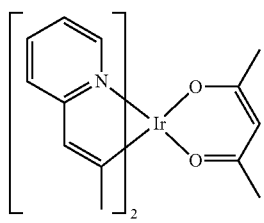 | Adv. Mater, 16, 2003 (2004) |
| | 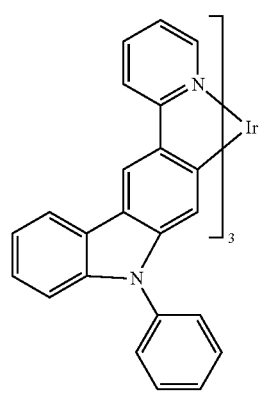 | Angew. Chem. Int. Ed. 2006, 45, 7800 |

| MATE-RIAL | EXAMPLES OF MATERIAL | PUBLICATIONS |
|---|---|---|
| | 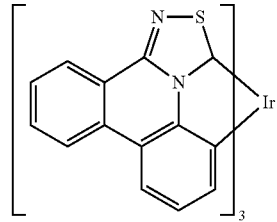 | WO2009050290 |
| | 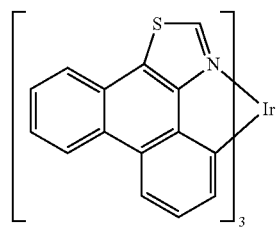 | US20090165846 |
| | 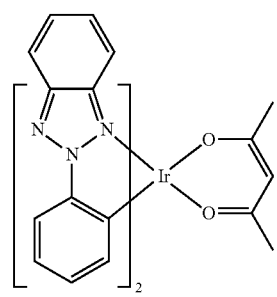 | US20080015355 |
| | 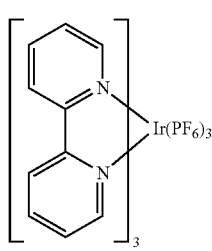 | US20010015432 |
| | 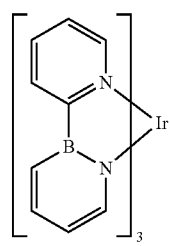 | US20100295032 |

TABLE A-continued
| MATERIAL | EXAMPLES OF MATERIAL | PUBLICATIONS |
|---|---|---|
| Monomer for polymeric metal organometallic compounds | 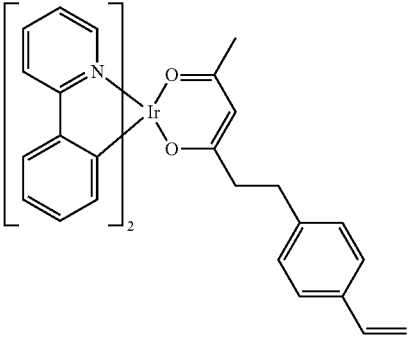 | US7250226, US7396598 |
| Pt(II) organometallic complexes, including polydentated ligands | 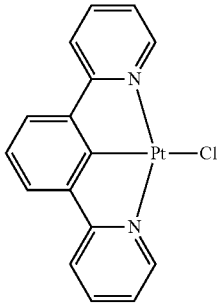 | Appl. Phys. Lett. 86, 153505 (2005) |
| | 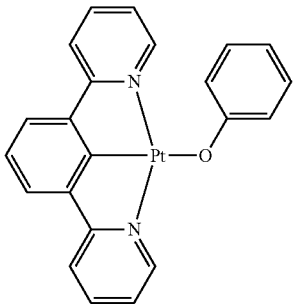 | Appl. Phys. Lett. 86, 153505 (2005) |
| | 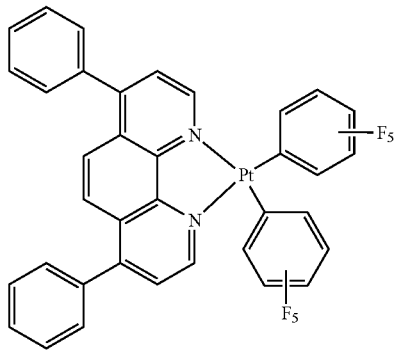 | Chem. Lett. 34, 592 (2005) |
| | 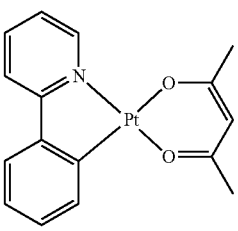 | WO2002015645 |

| MATE-RIAL | EXAMPLES OF MATERIAL | PUBLICATIONS |
|---|---|---|
| | 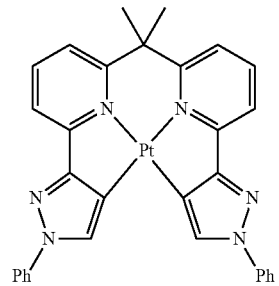 | US20060263635 |
| | 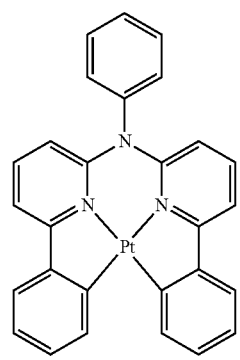 | US20060182992<br>US20070103060 |
| Cu complexes | 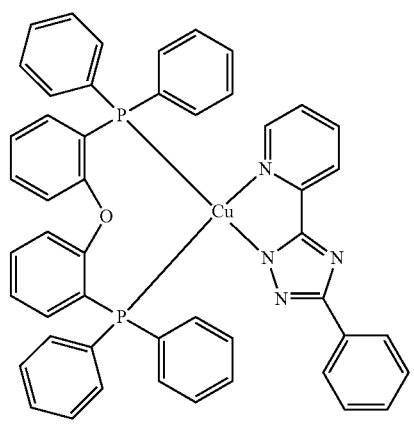 | WO2009000673 |
| | 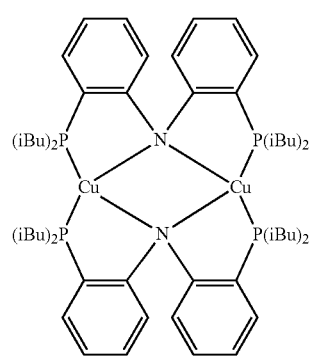 | US20070111026 |

TABLE A-continued
| MATERIAL | EXAMPLES OF MATERIAL | PUBLICATIONS |
|---|---|---|
| Gold complexes | 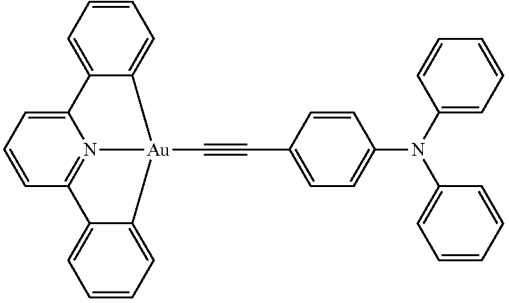 | Chem. Commun. 2906 (2005) |
| Rhenium (III) complexes | 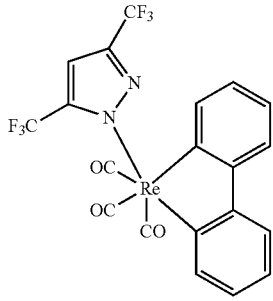 | Inorg. Chem. 42, 1248 (2003) |
| Osmium (II) complexes | 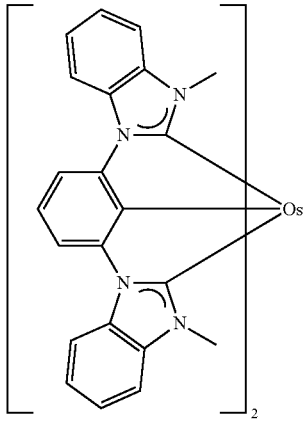 | US7279704 |
| Deuterated organometallic complexes | 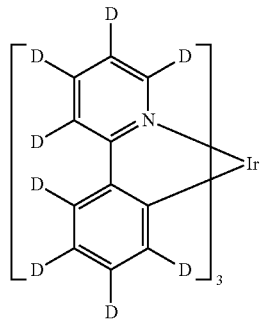 | US20030138657 |

TABLE A-continued
| MATERIAL | EXAMPLES OF MATERIAL | PUBLICATIONS |
|---|---|---|
| Organometallic complexes with two or more metal centers | 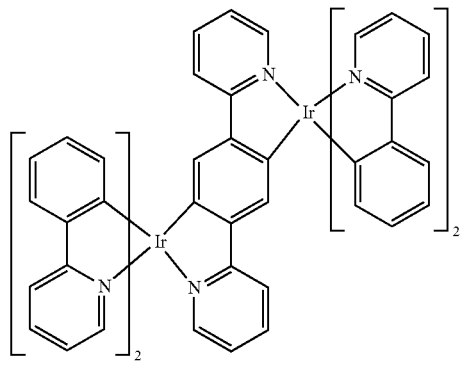 | US2003015802 |
| | 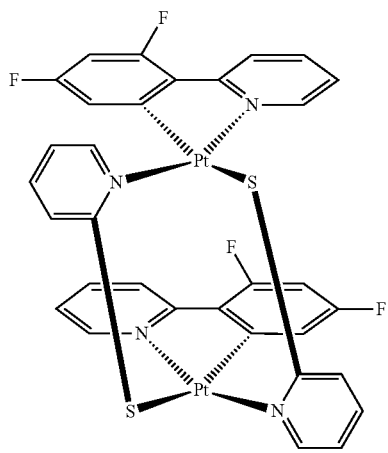 | US7090928 |
| Blue dopants | | |
| Iridium(III) organometallic complexes | 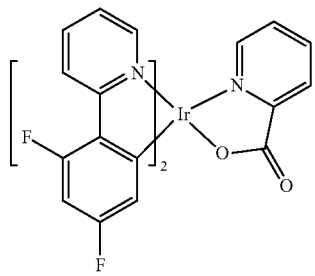 | WO2002002714 |
| | 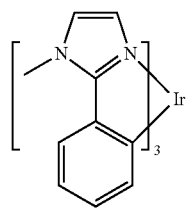 | WO2006009024 |
| | 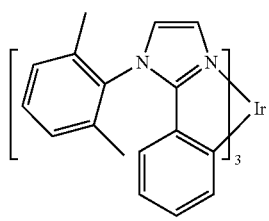 | US20060251923<br>US20110057559<br>US20110204333 |

TABLE A-continued

| MATERIAL | EXAMPLES OF MATERIAL | PUBLICATIONS |
|---|---|---|
| | | US7393599, WO2006056418, US20050260441, WO2005019373 |
| | | US7534505 |
| | | WO2011051404 |
| | | US7445855 |
| | | US20070190359, US20080297033 US20100148663 |

| MATERIAL | EXAMPLES OF MATERIAL | PUBLICATIONS |
|---|---|---|
| | 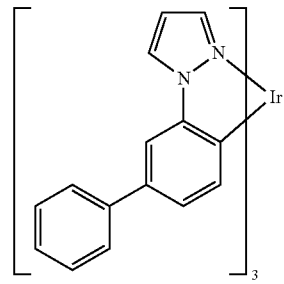 | US7338722 |
| | 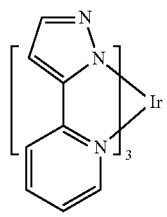 | US20020134984 |
| | 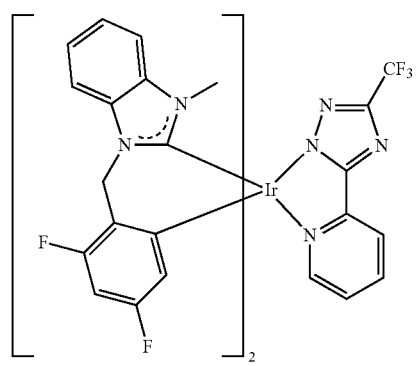 | Angew. Chem. Int. Ed. 47, 4542 (2008) |
| | 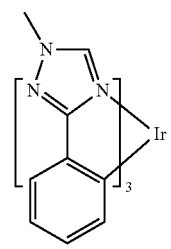 | Chem. Mater. 18, 5119 (2006) |
| | 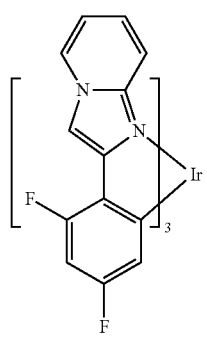 | Inorg. Chem. 46, 4308 (2007) |

| MATERIAL | EXAMPLES OF MATERIAL | PUBLICATIONS |
|---|---|---|
| | 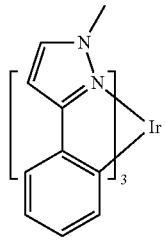 | WO2005123873 |
| | 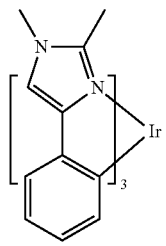 | WO2005123873 |
| | 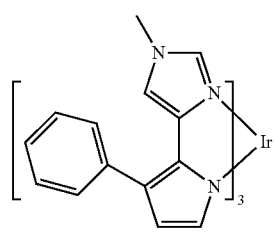 | WO2007004380 |
| | 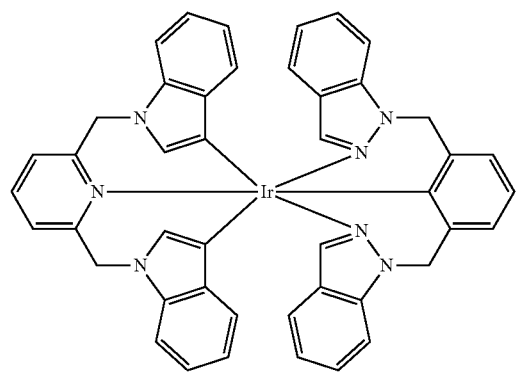 | WO2006082742 |
| Osmium (II) complexes | 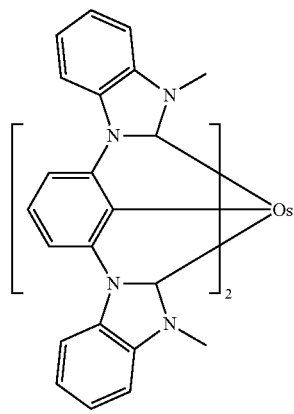 | US7279704 |

TABLE A-continued
| MATERIAL | EXAMPLES OF MATERIAL | PUBLICATIONS |
|---|---|---|
| | 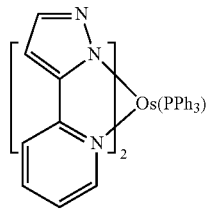 | Organometallics 23, 3745 (2004) |
| Gold complexes | 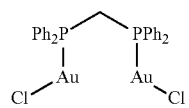 | Appl. Phys. Lett. 74, 1361 (1999) |
| Platinum (II) complexes | 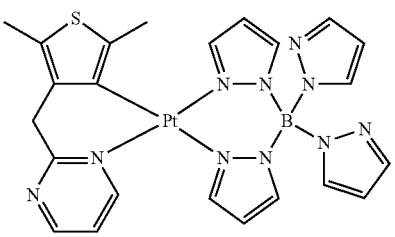 | WO2006098120, WO2006103874 |
| Pt tetradentate complexes with at least one metal-carbene bond | 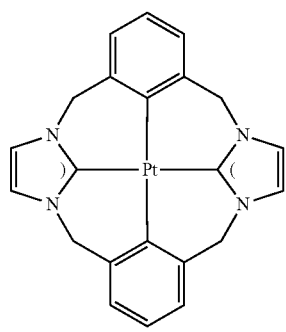 | US7655323 |
Exciton/hole blocking layer materials
| | | |
|---|---|---|
| Bathocuprine compounds (e.g., BCP, BPhen) | 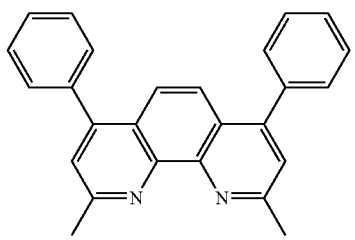 [SMILES: Cc1cc(-c2ccccc2)c2ccc3c(-c4ccccc4)cc(C)nc3c2n1] | Appl. Phys. Lett. 75, 4 (1999) |
| | 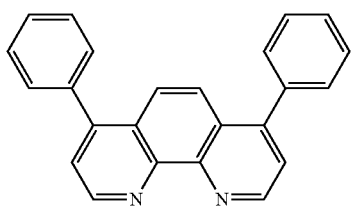 [SMILES: c1ccc(-c2ccnc3c2ccc2c(-c4ccccc4)ccnc23)cc1] | Appl. Phys. Lett. 79, 449 (1999) |

TABLE A-continued
| MATERIAL | EXAMPLES OF MATERIAL | PUBLICATIONS |
|---|---|---|
| Metal 8-hydroxyquinolates (e.g., BAlq) | 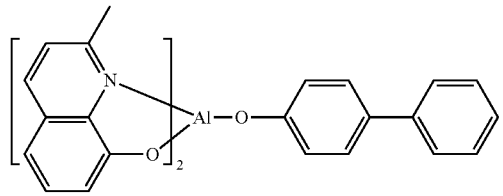 | Appl. Phys. Lett. 81, 162 (2002) |
| 5-member ring electron deficient heterocycles such as triazole, oxadiazole, imidazole, benzoimidazole | 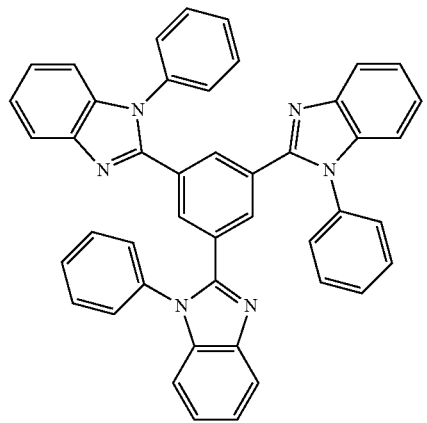 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 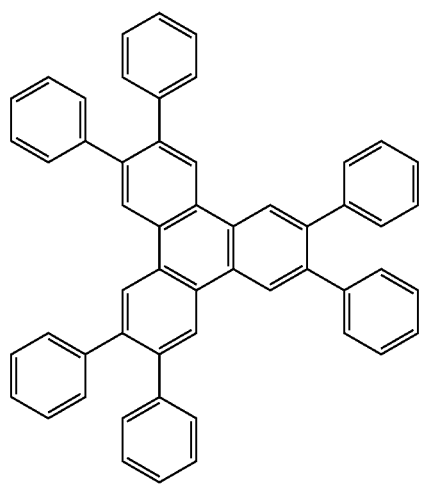 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE A-continued
| MATERIAL | EXAMPLES OF MATERIAL | PUBLICATIONS |
|---|---|---|
| Fluorinated aromatic compounds | 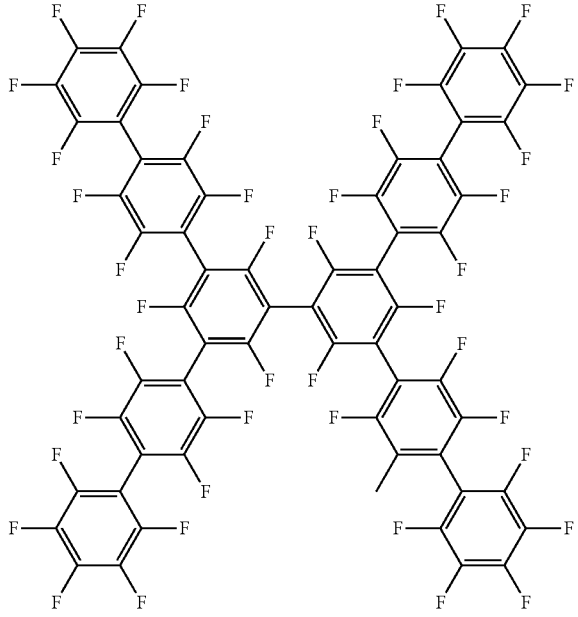 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 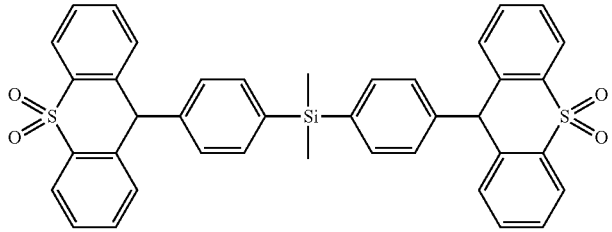 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 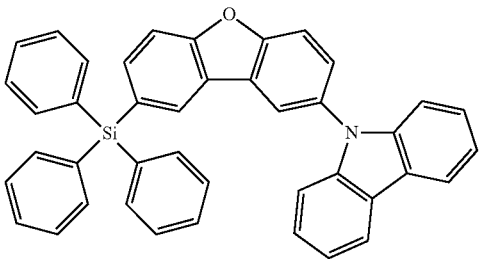 [SMILES: c1ccc([Si](c2ccccc2)(c2ccccc2)c2ccc3oc4ccc(-n5c6ccccc6c6ccccc65)cc4c3c2)cc1] | WO2010079051 |
| Azacarbazoles | 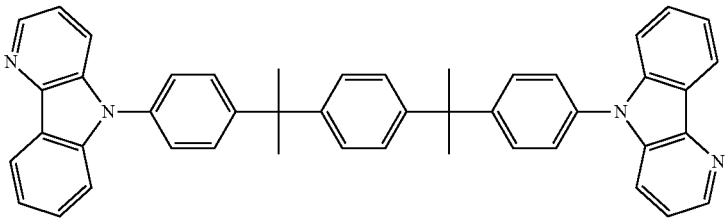 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE A-continued
| MATERIAL | EXAMPLES OF MATERIAL | PUBLICATIONS |
| --- | --- | --- |
| | Electron transporting materials | |
| Anthracene-benzoimidazole compounds | 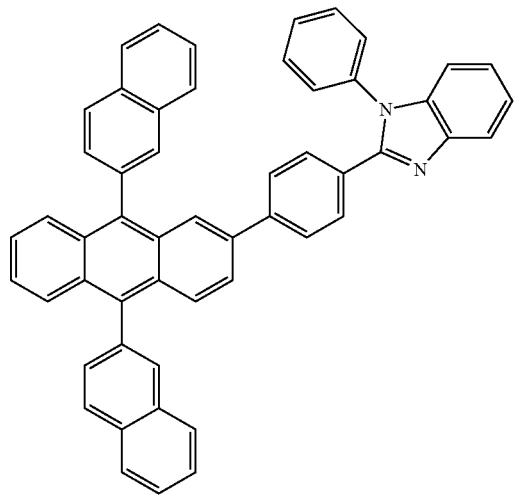 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 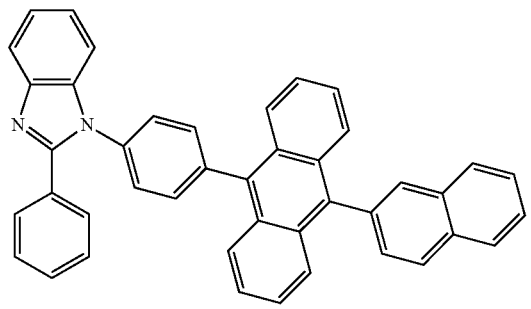 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 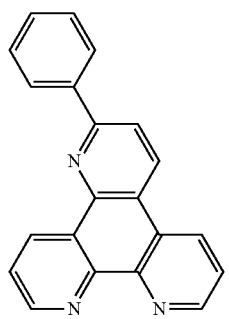 [SMILES: c1ccc(-c2ccc3c4cccnc4c4ncccc4c3n2)cc1] | US20090115316 |
| Anthracene-benzothiazole compounds | 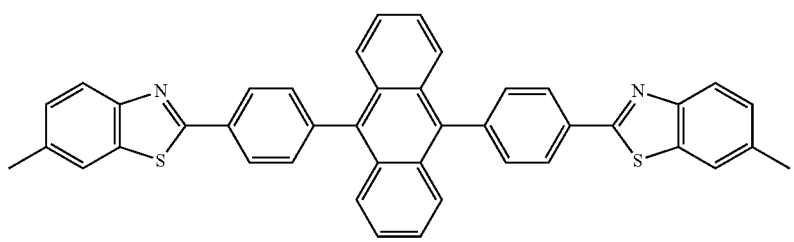 | Appl. Phys. Lett. 89, 063504 (2006) |

TABLE A-continued

| MATERIAL | EXAMPLES OF MATERIAL | PUBLICATIONS |
|---|---|---|
| Metal 8-hydroxyquinolates (e.g., Alq$_3$, Zrq$_4$) | 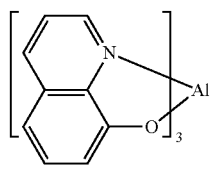 | Appl. Phys. Lett. 51, 913 (1987) US7230107 |
| Metal hydroxybenzoquinolates | 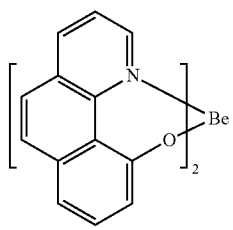 | Chem. Lett. 5, 905 (1993) |
| Bathocuprine compounds such as BCP, BCPhen, etc | 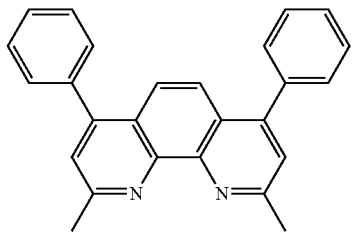 [SMILES: Cc1cc(-c2ccccc2)c2ccc3c(-c4ccccc4)cc(C)nc3c2n1] | Appl. Phys. Lett. 91, 263503 (2007) |
| | 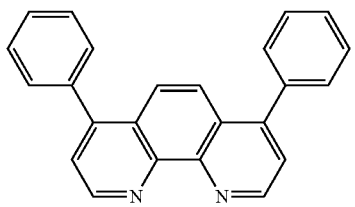 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 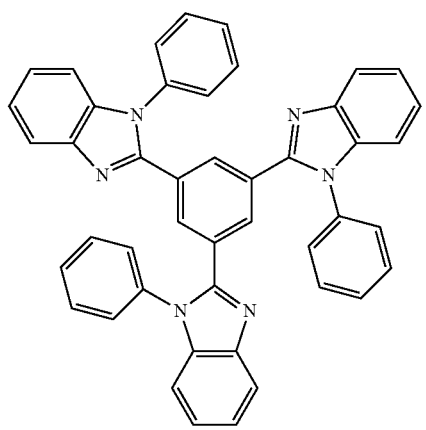 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 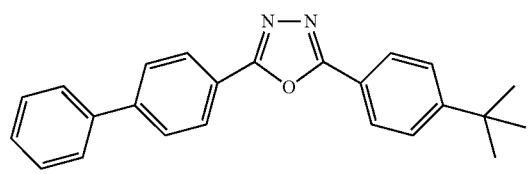 [SMILES: CC(C)(C)c1ccc(-c2nnc(-c3ccc(-c4ccccc4)cc3)o2)cc1] | Appl. Phys. Lett. 55, 1489 (1989) |

TABLE A-continued
| MATERIAL | EXAMPLES OF MATERIAL | PUBLICATIONS |
|---|---|---|
| | 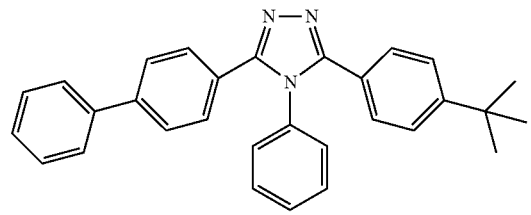 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 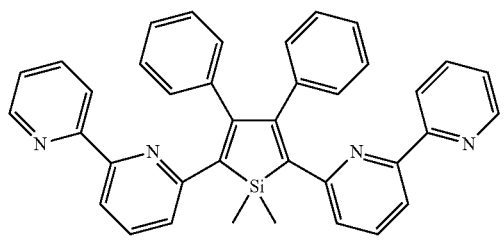 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 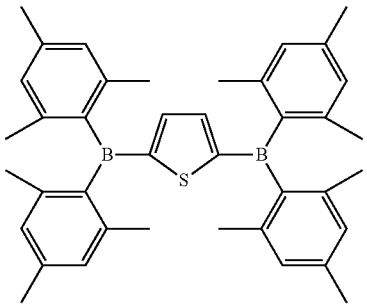 | J. Am. Chem. Soc. 120, 9714 (1998) |
| Fluorinated aromatic compounds | 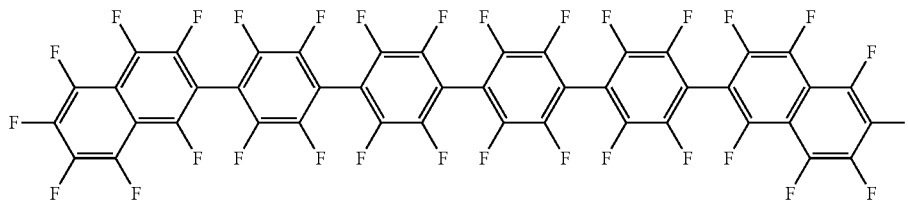 | J. Am. Chem. Soc. 122, 1832 (2000) |
| Fullerene (e.g., C60) | 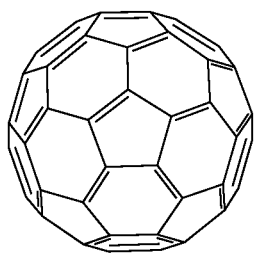 [SMILES: c1cc2c3ccc4c5ccc6c7ccc8c9ccc%10c1c1c2c2c3c4c3c5c6c4c7c8c5c9c%10c1c1c2c3c4c51] | US20090101870 |

TABLE A-continued
| MATERIAL | EXAMPLES OF MATERIAL | PUBLICATIONS |
|---|---|---|
| Triazine complexes | 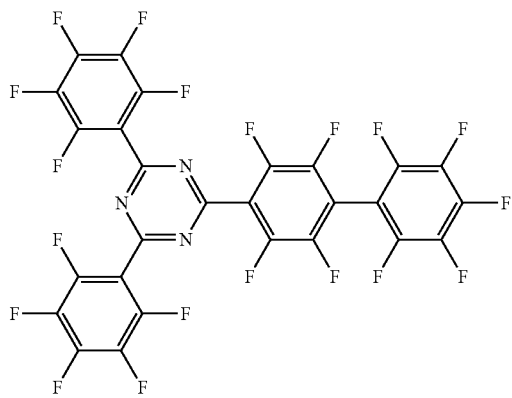 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 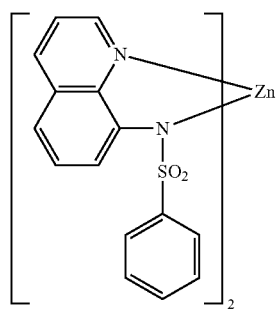 | US6528187 |
EXPERIMENTAL
Non-limiting examples of compounds of the invention that contain intramolecular hydrogen bonding include:
Compound 7
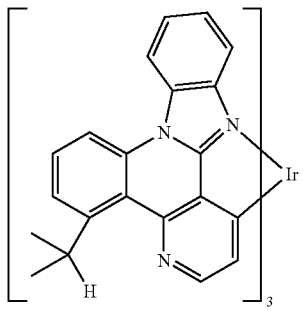
Compound 8
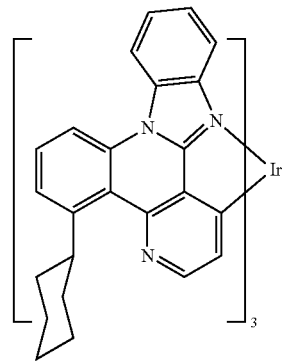

-continued

Compound 9

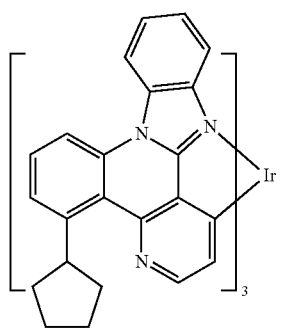

Compound 10

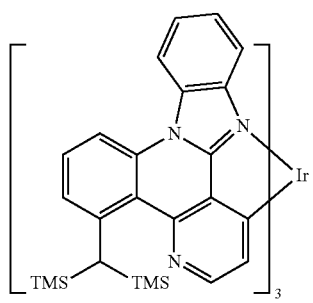

Compound 11

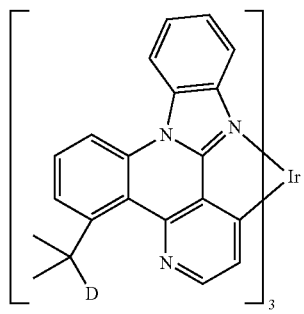

Compound 12

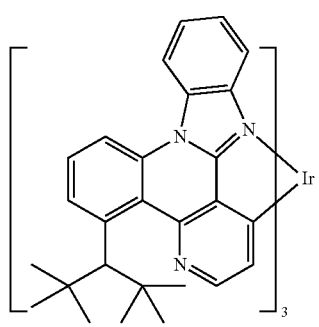

These complexes have been designed to place a proton in close proximity to the lone pair of the nitrogen in order to form a static intramolecular hydrogen bond. A spectrophotometric signature of this interaction may also be observed in the unusual triplet emission blue-shift in room temperature solution compared to 77K.

Figure 5:
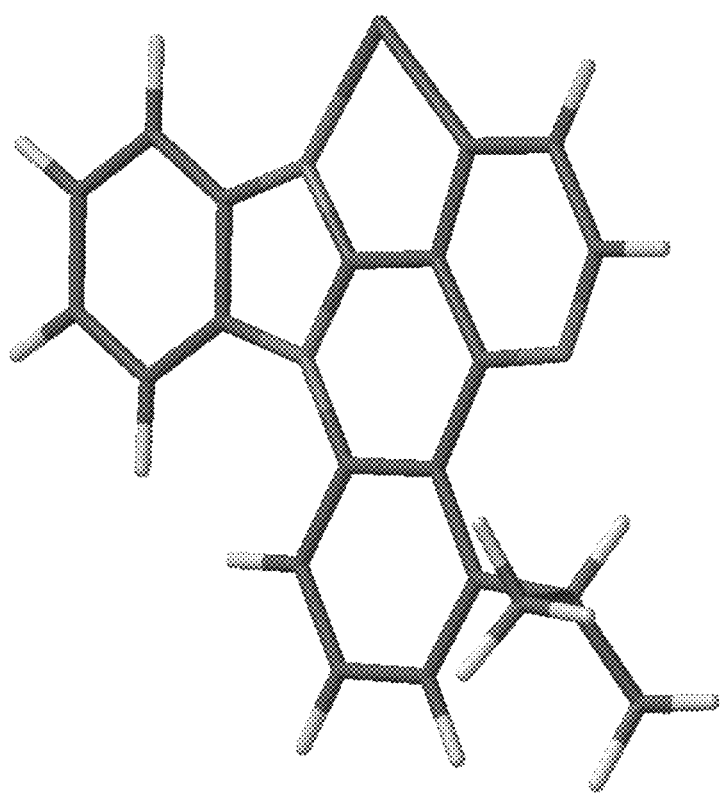
FIG. 5 shows an image of the minimized geometry of Compound 7. Two ligands have been removed for clarity.
Figure 6:
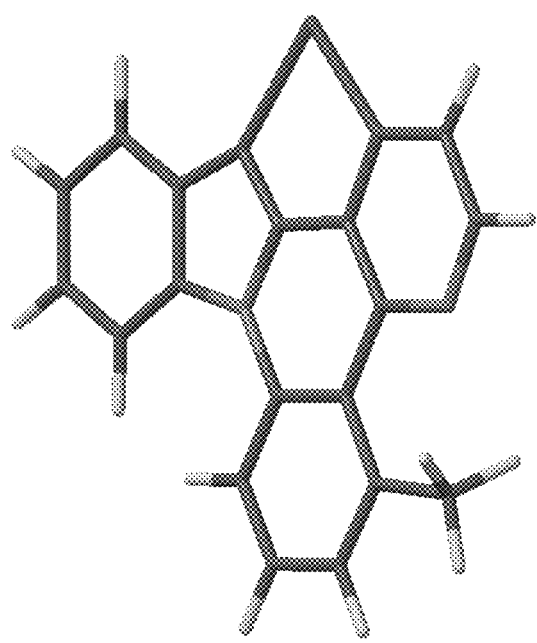
FIG. 6 shows an image of the minimized geometry of Compound 13. Two ligands have been removed for clarity.

Addressing the computational evidence for an intramolecular hydrogen bonding event, the minimized geometry for Compound 7 is shown in FIG. 5. Two ligands have been removed for clarity. It can be seen that H* is slightly above the plane of the lone pair of the nitrogen with a C—C—C—H dihedral angle of 31.6° and a H*—N distance of 2.15 Å. Although not wishing to be bound by any particular theory, it is hypothesized that the proximity of the proton to the uncoordinated nitrogen is caused by steric repulsion between the methyl substituents on the isopropyl group and the ring system on the APBI. This hypothesis is supported by comparison against the methyl-substituted Compound 13 (FIG. 6), in which no direct N—H* interaction is observed and the protons on the methyl group point as far from the nitrogen lone pair as physically possible.

Compound 13

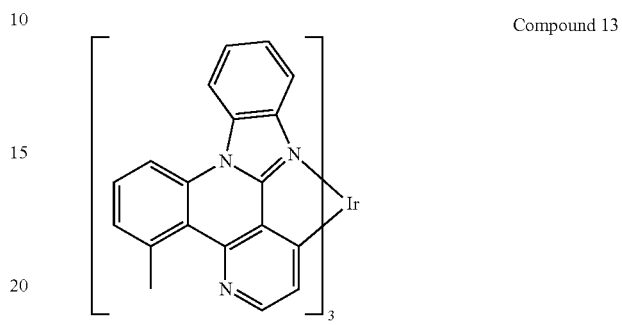

In this case the C—C—C—H dihedral is 61.8°, and the N—H* bond distance is 2.52 Å. Minimized geometries for Compound 8 and Compound 9 show a similar N—H* interaction to Compound 7. The C—C—C—H dihedral angle and N—H* bond distance for Compound 8 are 34.7° and 2.16 Å, respectively. The C—C—C—H dihedral angle of interest is highlighted below:

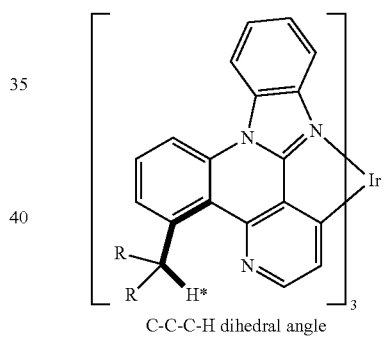

C-C-C-H dihedral angle

Figure 7:
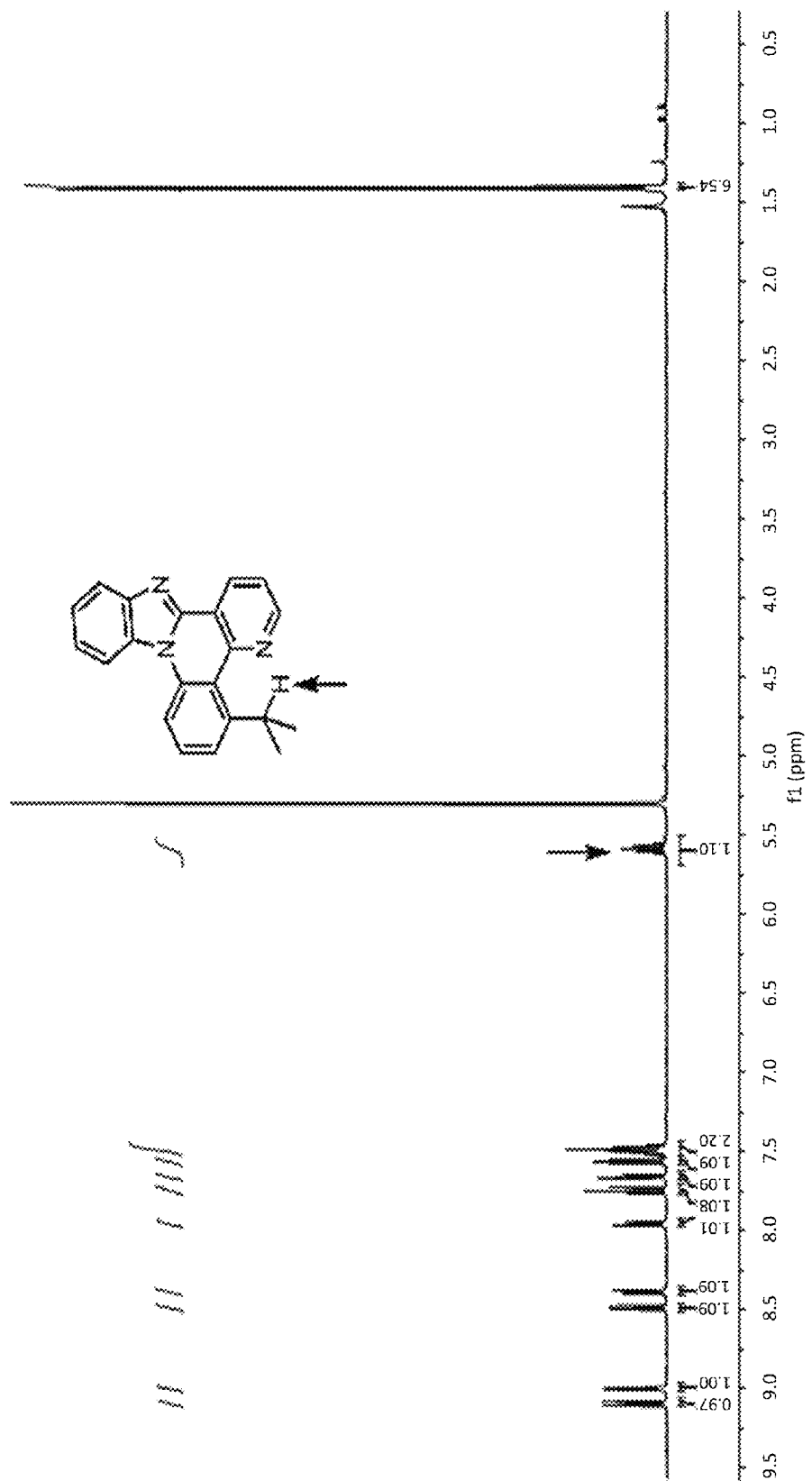
FIG. 7 shows an $^1$H NMR spectrum of the ligand of Compound 7 in $CD_2Cl_2$ solvent.
Figure 8:
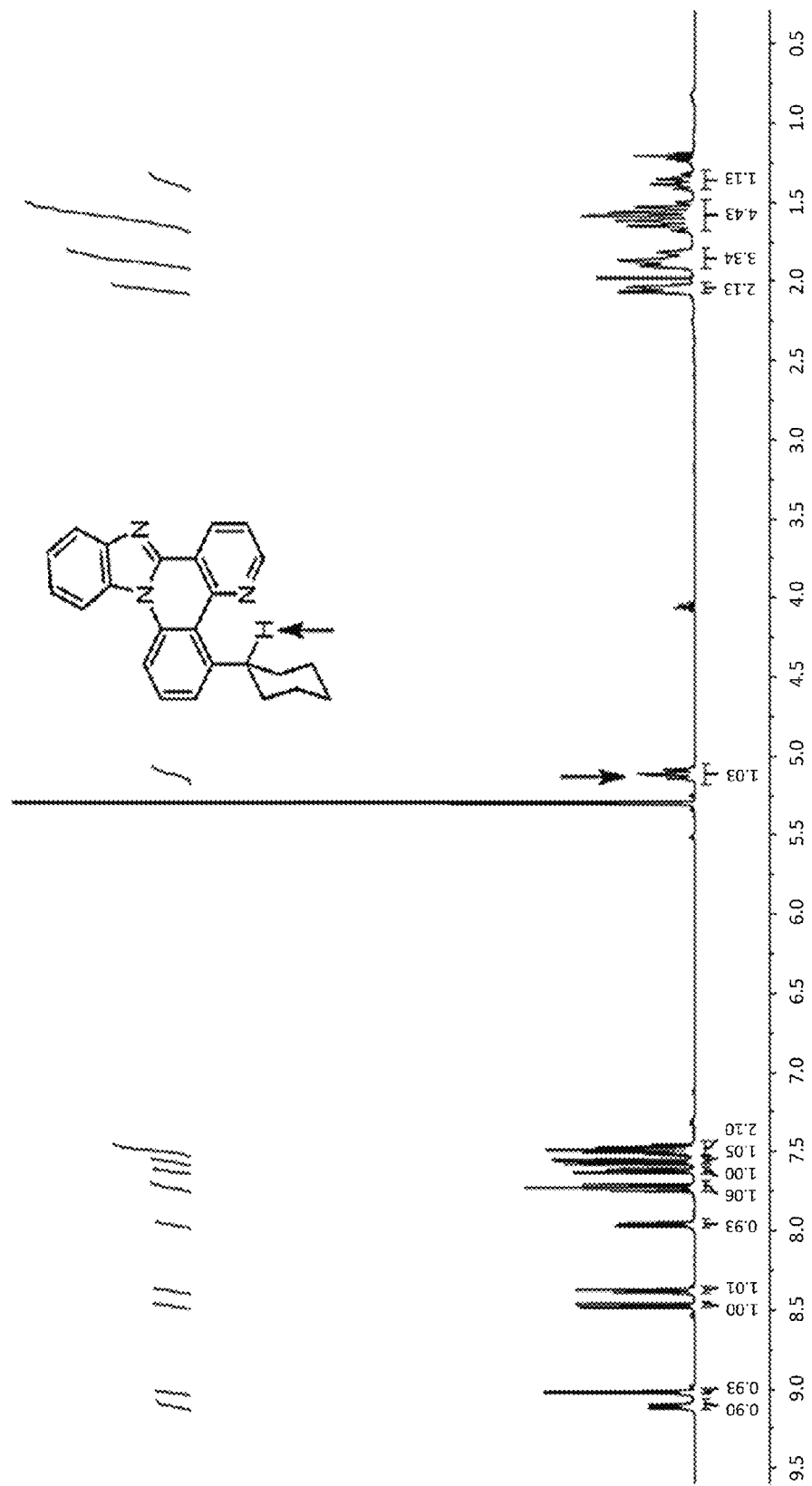
FIG. 8 shows an $^1$H NMR spectrum of the ligand of Compound 8 in $CD_2Cl_2$ solvent.
Figure 9:
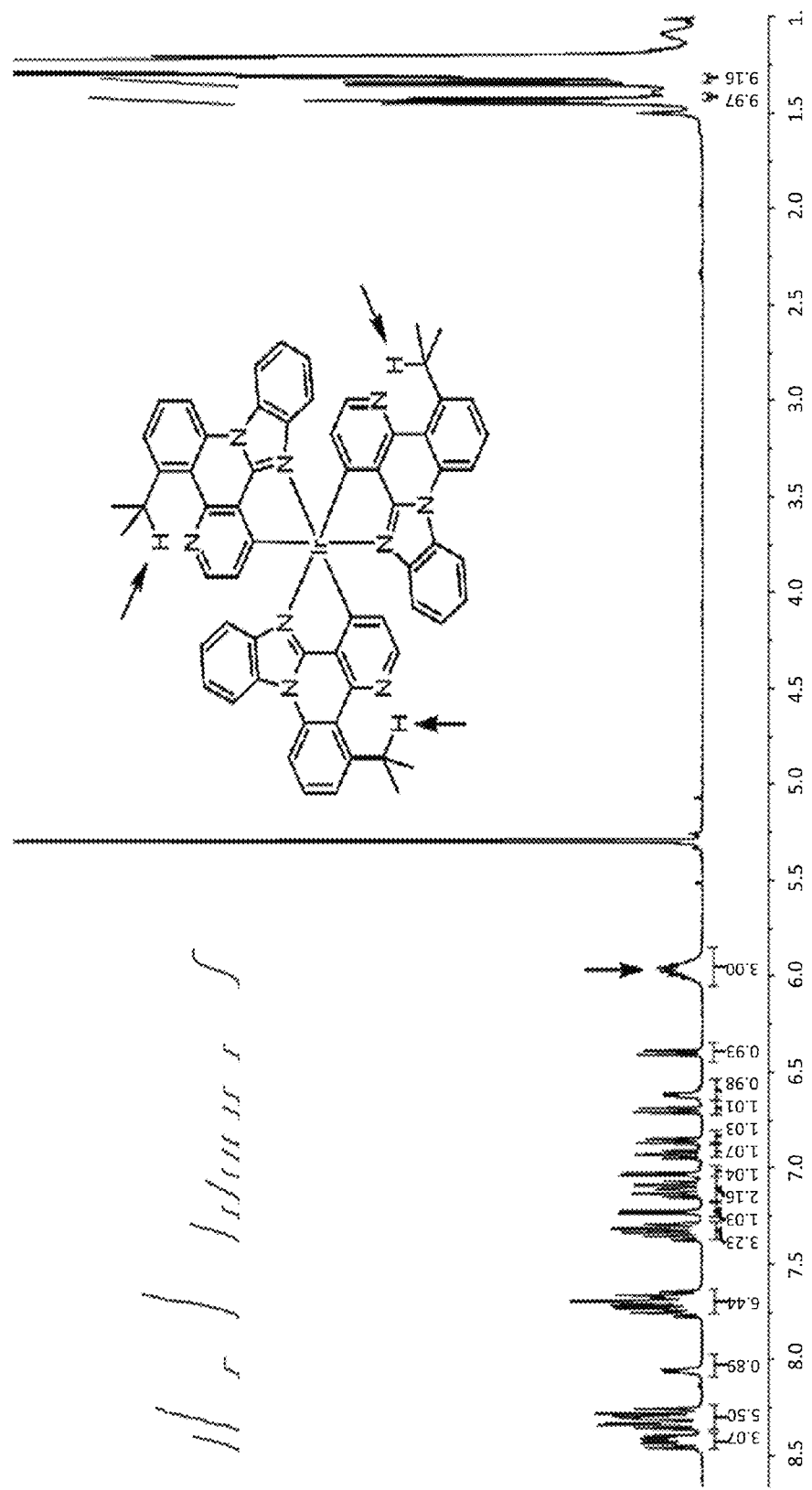
FIG. 9 shows an $^1$H NMR spectrum of Compound 7 in $CD_2Cl_2$ solvent.
Figure 10:
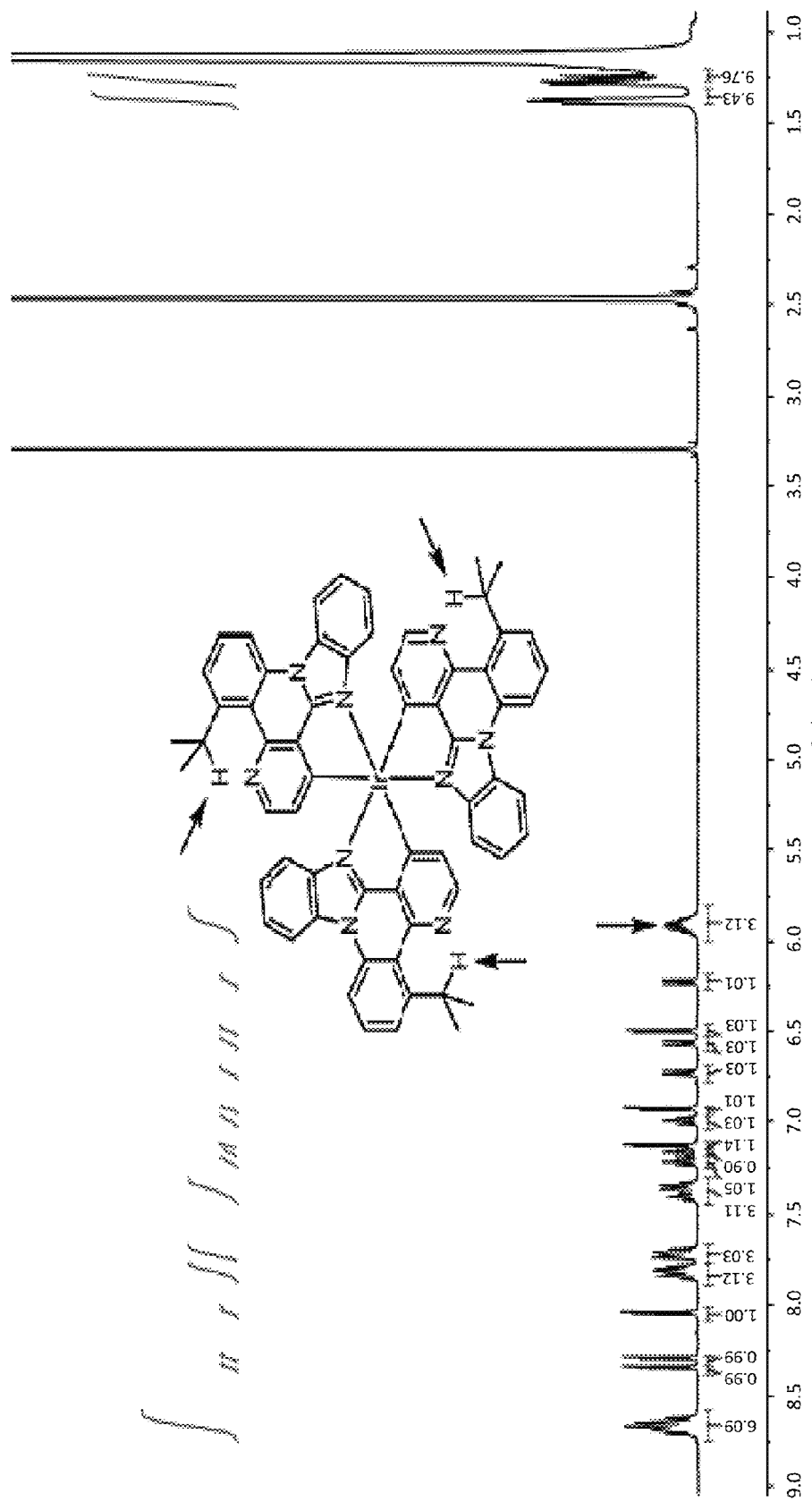
FIG. 10 shows an $^1$H NMR spectrum of Compound 7 in DMSO-$d_6$ solvent.

The experimental evidence for a static intramolecular hydrogen bond to the lone pair of the uncoordinated nitrogen is observable in the $^1$H NMR for both the free ligand and iridium complex. For reference, the methyl protons for the ligand of Compound 13 are measured at 3.26 ppm in CD$_2$Cl$_2$. In comparison, the H* protons in the ligands of Compounds 7 and 8 are shifted significantly downfield to 5.6 ppm and 5.2 ppm, respectively, as shown in FIG. 7 and FIG. 8. A similar downfield shift is observed after cyclometalation to iridium(III), as demonstrated in the $^1$H NMR spectra for Complex 7 in CD$_2$Cl$_2$ and DMSO-d$_6$ (FIGS. 9 and 10, respectively), with chemical shifts of 5.9 ppm irrespective of solvent polarity. This downfield shift is a result of the well-understood phenomenon of hydrogen-bonding-induced proton de-shielding, indicative of an intramolecular hydrogen-bonding interaction.

The $^1$H NMR chemical shifts of H* were also calculated for the ligands and their corresponding compounds of Compound 7, Compound 8 and Compound 13, together with Comparative Examples 1 to 8. Calculations were carried out using the B3LYP/6-31g* functional and basis set on the Gaussian software package. The calculated values match very closely to the experimental values. Further evidence of intramolecular H-bonding is found by comparing the calculated chemical shift of H* to Comparative Examples 1-8, where intramolecular H-bonding is not available. In all of these cases, NMR chemical shifts of H* in C—H*--N analogs are all significantly shifted downfield compared to their C—H*--C analogs, with differences ranging from 1.4 to 2.1 ppm, or from 37% to 50% based on C—H*--C analogs (Table 1).

TABLE 1

Experimental and calculated chemical shifts of H*

| Compound Structures | Experimental chemical shift of H* (ppm) Difference (ppm), and percentage change of C—H*----N vs. C—H*----C having similar structure | Calculated chemical shift of H* (ppm) Difference (ppm), and percentage change of C—H*----N vs. C—H*----C having similar structure |
|---|---|---|
| Ligand of Compound 7 | 5.59 | 5.5 1.5, 37.5% (vs Comparative Example 1) |
| Comparative Example 1 | | 4.0 |
| Ligand of Compound 8 | 5.11 1.43, 38.9% (vs Comparative Example 4) | 5.2 1.5, 40.5% (vs Comparative Example 2) 1.5, 40.5% (vs Comparative Example 4) |

TABLE 1-continued

Experimental and calculated chemical shifts of H*

| Compound Structures | Experimental chemical shift of H* (ppm) Difference (ppm), and percentage change of C—H*- - - -N vs. C—H*- - - -C having similar structure | Calculated chemical shift of H* (ppm) Difference (ppm), and percentage change of C—H*- - - -N vs. C—H*- - - -C having similar structure |
|---|---|---|
| Comparative Example 2 | | 3.7 |
| Comparative Example 4 | 3.68 | 3.7 |
| Ligand of Compound 13 | 3.24 | 3.1<br>0.2, 6.9% (vs Comparative Example 3) |
| Comparative Example 3 | | 2.9 |

TABLE 1-continued

Experimental and calculated chemical shifts of H*

| Compound Structures | Experimental chemical shift of H* (ppm) Difference (ppm), and percentage change of C—H*----N vs. C—H*----C having similar structure | Calculated chemical shift of H* (ppm) Difference (ppm), and percentage change of C—H*----N vs. C—H*----C having similar structure |
|---|---|---|
| 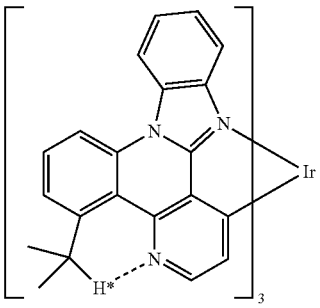<br>Compound 7 | 5.96 (for mer$^a$) | 6.3<br>2.1, 50% (vs Comparative Example 6) |
| 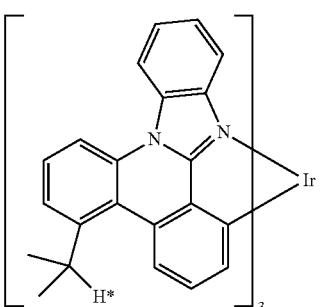<br>Comparative Example 6 | | 4.2 |
| 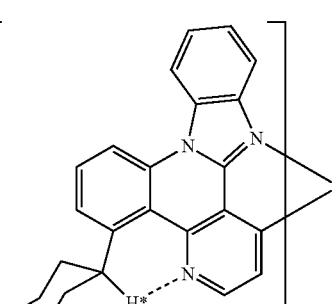<br>Compound 8 | 5.45<br>1.56, 40.1% (vs Comparative Example 5) | 6.0<br>2.0, 50% (vs Comparative Example 7)<br>2.0, 50% (vs Comparative Example 5) |
| 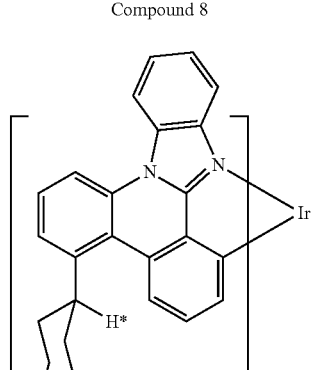<br>Comparative Example 7 | | 4.0 |

TABLE 1-continued

Experimental and calculated chemical shifts of H*

| Compound Structures | Experimental chemical shift of H* (ppm) Difference (ppm), and percentage change of C—H*- - - -N vs. C—H*- - - -C having similar structure | Calculated chemical shift of H* (ppm) Difference (ppm), and percentage change of C—H*- - - -N vs. C—H*- - - -C having similar structure |
|---|---|---|
| Comparative Example 5 | 3.89 | 4.0 |
| Compound 13 | 3.35 | 3.6<br>0.5, 16% (vs Comparative Example 8) |
| Comparative Example 8 | | 3.1 |

[a] all data shown in the table for Ir complexes are based on fac isomer, except for this one.

Figure 11:
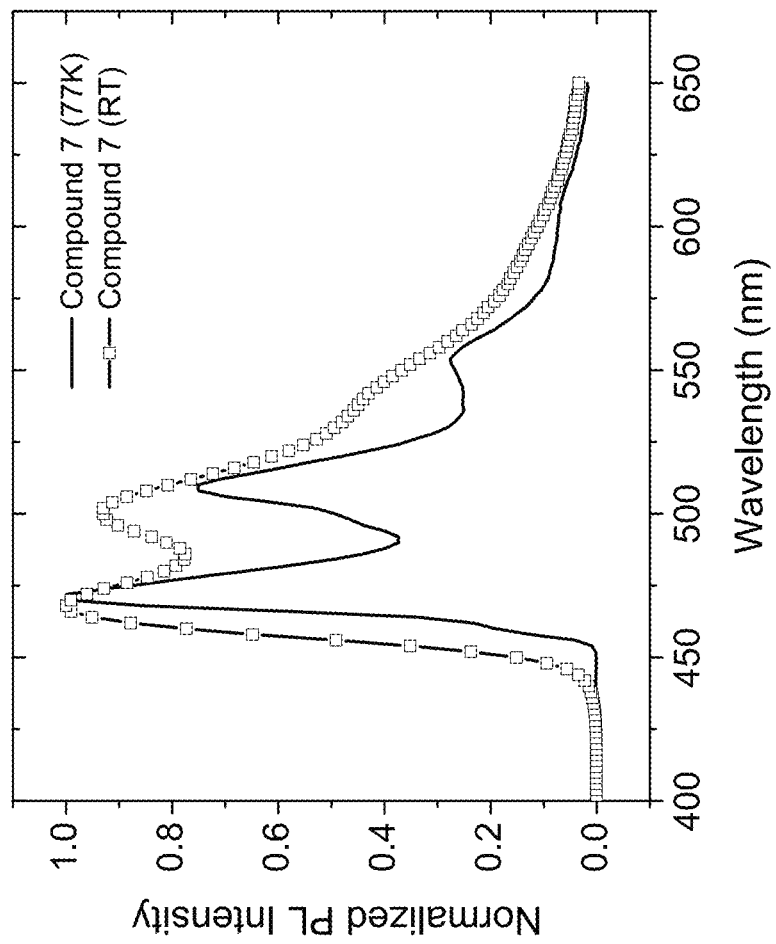
FIG. 11 shows a room temperature and 77 K emission spectrum of Compound 7 in 2-MeTHF.
Figure 12:
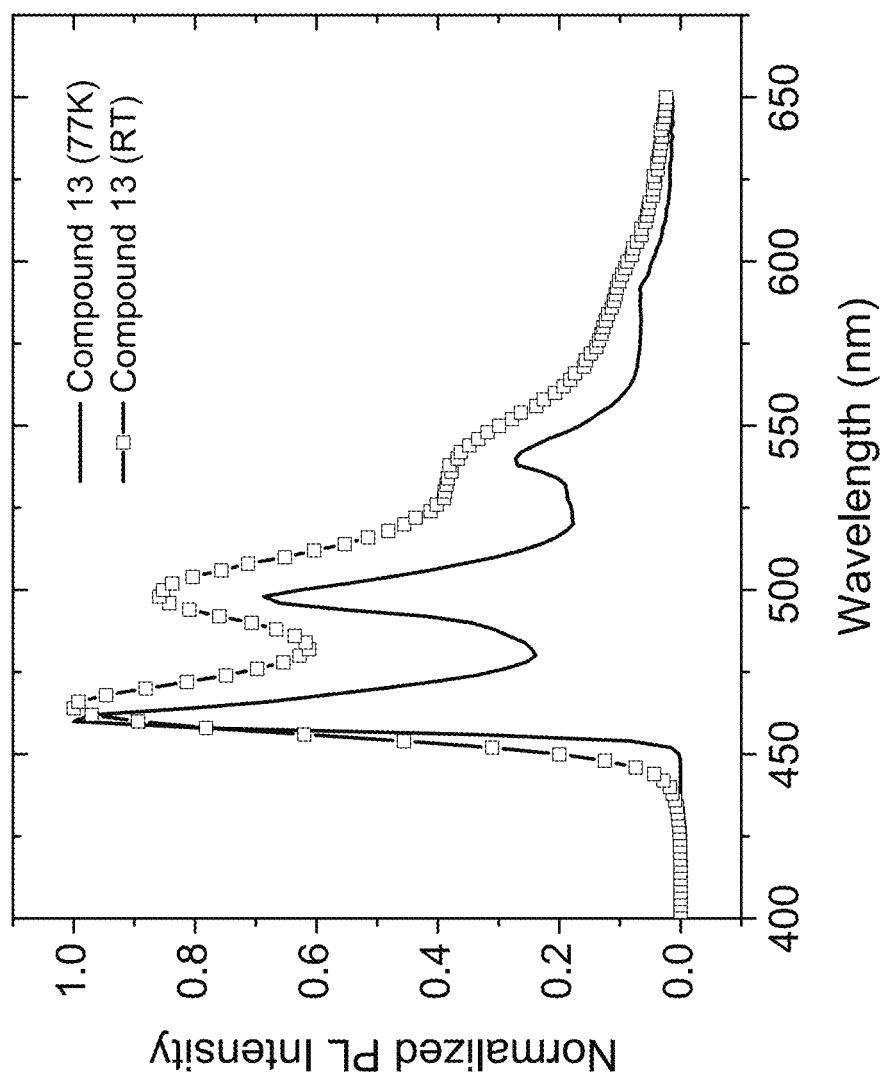
FIG. 12 shows a room temperature and 77 K emission spectrum of Compound 13 in 2-MeTHF.

Additional evidence of an H bonding interaction can be found in a feature of the emission spectra of Compound 7. FIG. 11 shows the emission spectra of Compound 7 in 2-methyl tetrahydrofuran (2-MeTHF) solvent at room temperature and 77 K. The room temperature emission was found to be significantly blue-shifted relative to 77 K, unlike any other Ir(APBI)$_3$ complex yet measured. Although not wishing to be bound by any particular theory, it is hypothesized that this blue shift may be due to an inductive withdrawing effect, which reduces electron density on the covalently attached ring, thereby blue shifting the emission spectra. Although not wishing to be bound by any particular theory, the fact that this effect is more significant at room temperature is suggestive of a vibrational interaction between the H and N atoms which is frozen out at 77 K. For comparison purposes, the spectrum for Compound 13 is shown in FIG. 12. This compound shows a blue shift as the molecule is rigidified at 77K, typical of most phosphorescent complexes.

Synthesis of Exemplary Ligands and Complexes:
Synthesis of Compound 7:

Synthesis of 10-chlorobenzo[h][1,6]naphthyridin-5-amine

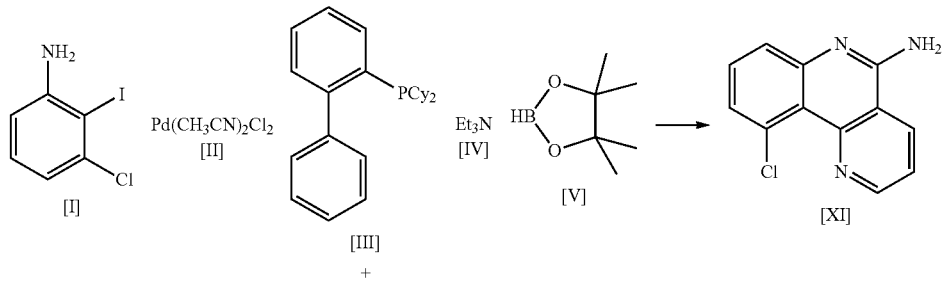

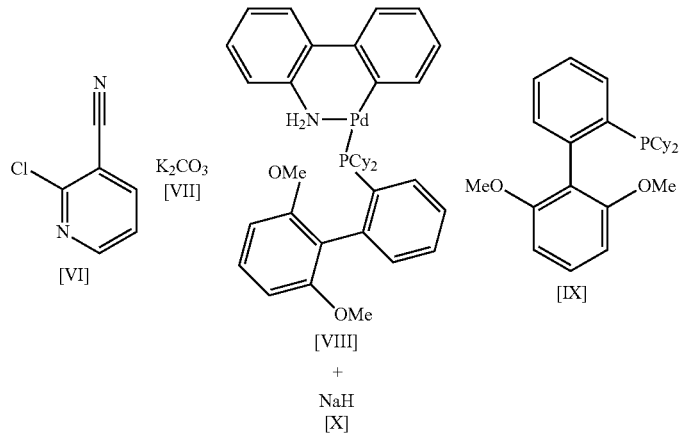

A mixture of 3-chloro-2-iodoaniline (9.60 g, 37.9 mmol), CyJohnPhos (0.506 g, 1.443 mmol), and Pd(CH$_3$CN)$_2$Cl$_2$ (0.187 g, 0.722 mmol) was dissolved in dioxane (80 ml). Triethylamine (15.09 ml, 108 mmol) and 4,4,5,5-tetramethyl-1,3,2-dioxaborolane (11.00 ml, 76 mmol) were added to the solution in sequence via syringe. The reaction was refluxed for 4 h. The reaction was cooled to R.T. and a solid mixture of 2-chloronicotinonitrile (5 g, 36.1 mmol), S-Phos Pd G2 (0.520 g, 0.722 mmol), S-Phos (0.296 g, 0.722 mmol), and potassium carbonate (9.97 g, 72.2 mmol) was added to the reaction mixture directly followed by the addition of dioxane (20 ml) and water (20 ml) and the reaction was heated to 85° C. overnight. Dioxane was removed and the crude product was extracted with dichloromethane (DCM). The organic part was evaporated to provide an oily product. The product was dissolved in THF (80 mL), and sodium hydride (2.165 g, 54.1 mmol) was directly added at 0° C. and stirred for 25 min. The reaction was quenched with brine (~150 mL). After THF was evaporated, hexanes and diethyl ether (~1:2, roughly 30 mL in total) were added to the suspension, which was then stirred for about 3 min. The solids were collected by filtration and washed with diethyl ether to afford crude 10-chlorobenzo[h][1,6]naphthyridin-5-amine, which was directly used in the next step without further purification (60% yield).

Synthesis of 5-chlorobenzo[h]benzo[4,5]imidazo[2,1-f][1,6]naphthyridine

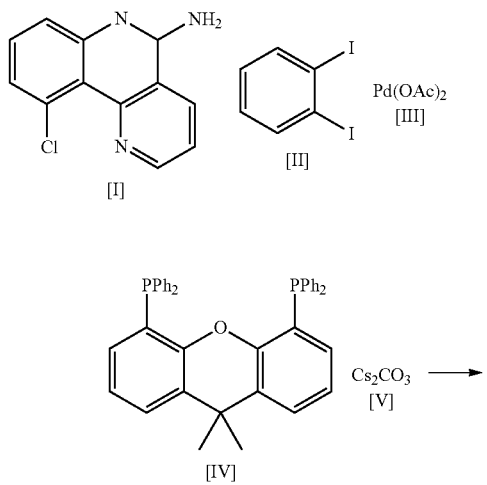

-continued

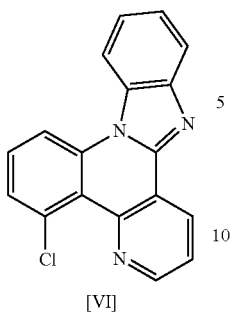

[VI]

A mixture of 10-chlorobenzo[h][1,6]naphthyridin-5-amine (3.11 g, 13.54 mmol), diacetoxypalladium (0.152 g, 0.677 mmol), Xantphos (0.392 g, 0.677 mmol), and cesium carbonate (17.65 g, 54.2 mmol) was vacuumed and back-filled with nitrogen several times, and 1,2-diiodobenzene (1.947 ml, 14.90 mmol) and toluene (70 ml) were added to the solution. The reaction was refluxed for 3 h. The product was purified by column chromatography on silica (DCM/MeOH=20/1). The product was washed with diethyl ether (52% yield).

Synthesis of 5-(prop-1-en-2-yl)benzo[h]benzo[4,5]imidazo[2,1-f][1,6]naphthyridine

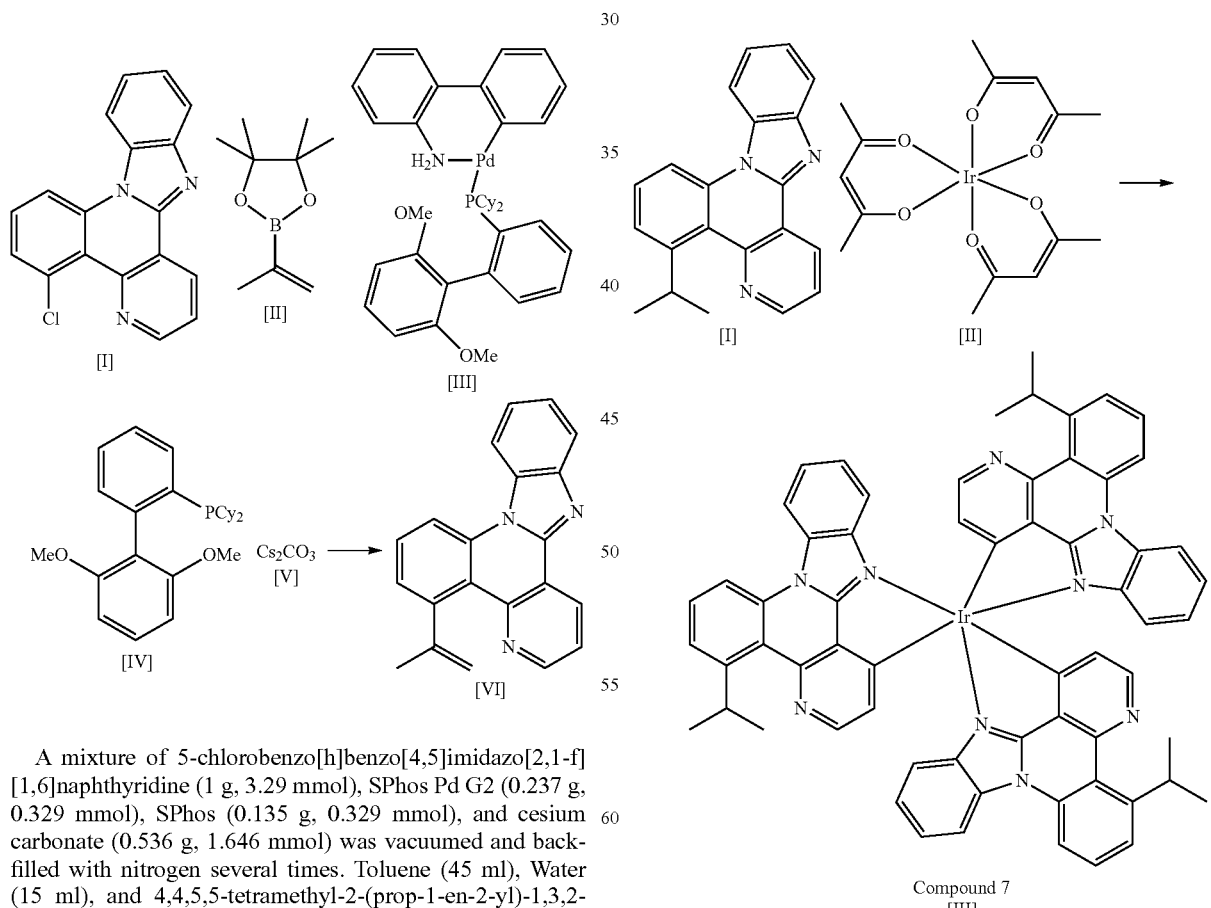

A mixture of 5-chlorobenzo[h]benzo[4,5]imidazo[2,1-f][1,6]naphthyridine (1 g, 3.29 mmol), SPhos Pd G2 (0.237 g, 0.329 mmol), SPhos (0.135 g, 0.329 mmol), and cesium carbonate (0.536 g, 1.646 mmol) was vacuumed and back-filled with nitrogen several times. Toluene (45 ml), Water (15 ml), and 4,4,5,5-tetramethyl-2-(prop-1-en-2-yl)-1,3,2-dioxaborolane (1.257 ml, 6.58 mmol) were added and heated at reflux overnight. The reaction mixture was coated on celite and chromatographed on silica (DCM/EtOAc/heptanes=6/1/2) (50% yield).

Synthesis of 5-isopropylbenzo[h]benzo[4,5]imidazo[2,1-f][1,6]naphthyridine

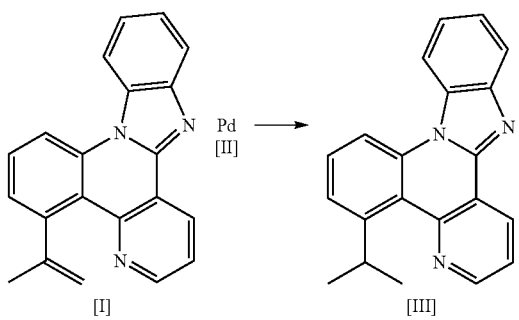

5-(prop-1-en-2-yl)benzo[h]benzo[4,5]imidazo[2,1-f][1,6]naphthyridine (1.05 g, 3.39 mmol) was dissolved in ethyl acetate (60 ml) and, and ethanol (50 ml) and palladium (0.361 g, 0.339 mmol) were added. The reaction mixture was vacuumed and back-filled with a hydrogen balloon three times and stirred at R.T. overnight. The reaction was filtered through Celite and the solvent was evaporated. The solid was washed with diethyl ether and hexane (~1:2) to afford pure product (99% yield).

Synthesis of Compound 7:

Compound 7
[III]

5-isopropylbenzo[h]benzo[4,5]imidazo[2,1-f][1,6]naphthyridine (900 mg, 2.89 mmol), Ir(acac)₃ (283 mg, 0.578 mmol), and pentadecane (2 mL) were combined in a Schlenk tube and the tube was vacuumed and back-filled with $N_2$ three times. The tube was heated to 290° C. for 2 days. The crude product was purified by column chromatography on alumina (100 g, deactivated with 10% $H_2O$, DCM/Hep=3/2). The product was further purified on silica gel column (DCM) to yield Compound 7 (15.4%).

Synthesis of Compound 8:

Synthesis of 5-(cyclohex-1-en-1-yl)benzo[h]benzo[4,5]imidazo[2,1-f][1,6]naphthyridine Synthesis of Ligand of Compound 8:

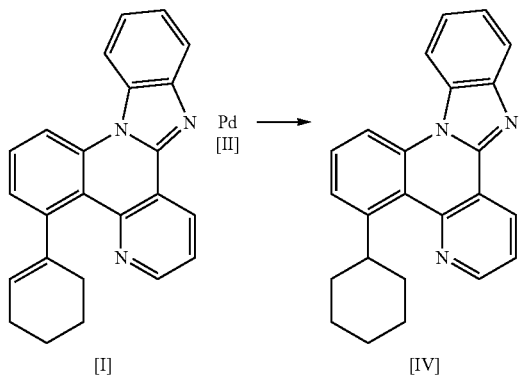

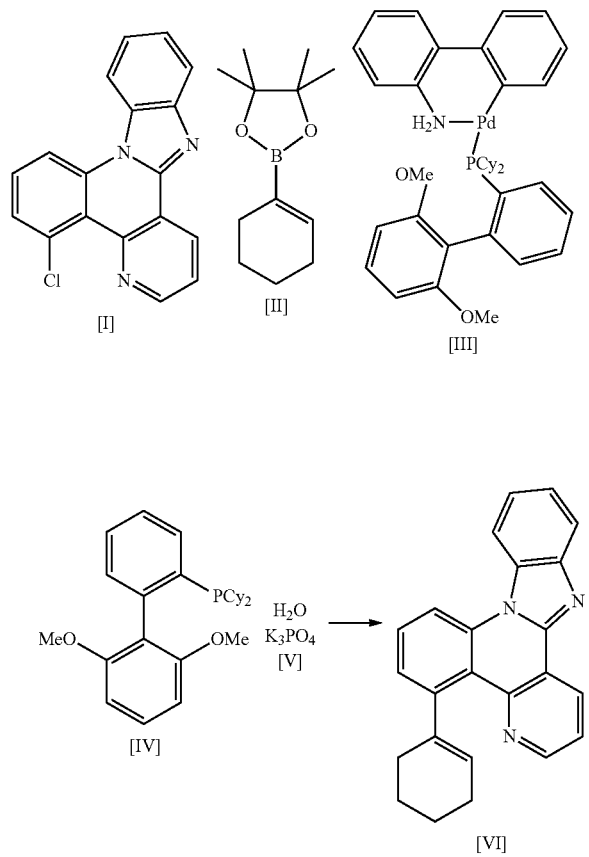

A mixture of 5-chlorobenzo[h]benzo[4,5]imidazo[2,1-f][1,6]naphthyridine (2.13 g, 7.01 mmol), SPhos Pd G2 (0.505 g, 0.701 mmol), SPhos (0.288 g, 0.701 mmol), and potassium phosphate monohydrate (4.84 g, 21.04 mmol) was vacuumed and back-filled with nitrogen several times. Toluene (75 ml), Water (25 ml), and 2-(cyclohex-1-en-1-yl)-4,4,5,5-tetramethyl-1,3,2-dioxaborolane (2.292 ml, 10.52 mmol) were added and heated at reflux overnight. The reaction was extracted with DCM and brine and purified by column chromatography on silica (EA/Hep=1/3) (75% yield).

Dissolved 5-(cyclohex-1-en-1-yl)benzo[h]benzo[4,5]imidazo[2,1-f][1,6]naphthyridine (1.59 g, 4.55 mmol) in Ethyl acetate (90 ml) and added Ethanol (70 ml) and palladium (0.484 g, 0.455 mmol). The reaction mixture was vacuumed and back-filled with a hydrogen balloon three times and stirred at R.T. for 3 days. The reaction was filtered through Celite and evaporated. The product was purified by column chromatography on silica with pure EA (54% yield).

Synthesis of Compound 8:

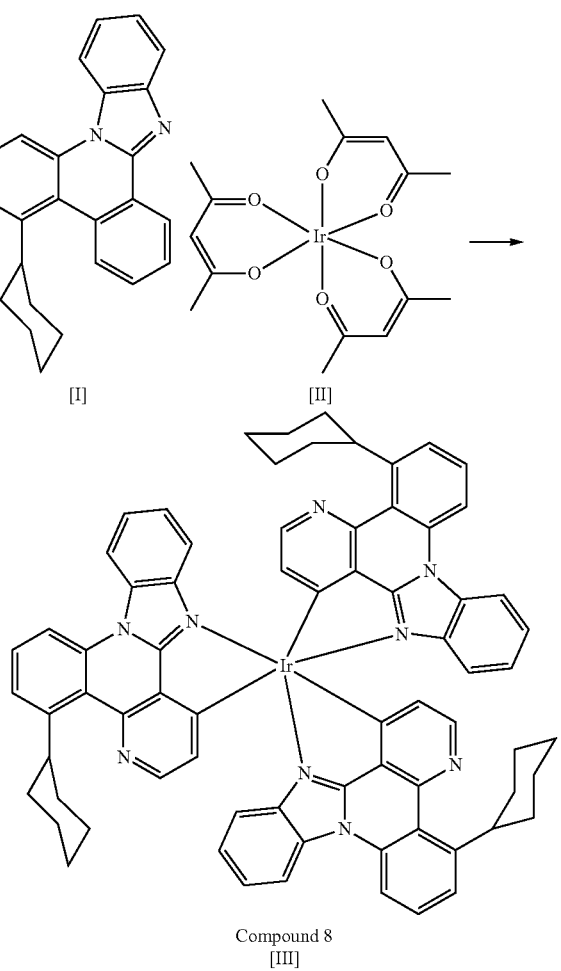

Compound 8
[III]

A mixture of 5-cyclohexylbenzo[h]benzo[4,5]imidazo[2,1-f][1,6]naphthyridine (1 g, 2.85 mmol), Ir(acac)₃ (279 mg, 0.569 mmol), and pentadecane (4 mL) were added to an acid digestion bomb in a glove box and heated at 285° C. in a sand bath overnight. The product was purified by column chromatography on silica column (DCM). The product was triturated in MeOH and diethyl ether and filtered (26% yield).

Synthesis of Comparative Example 5

Synthesis of 1-chlorophenanthridin-6-amine

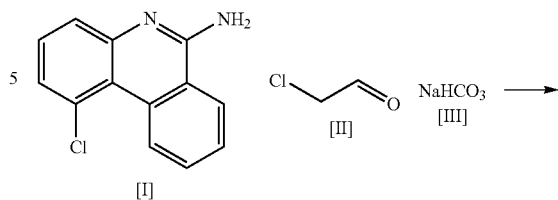

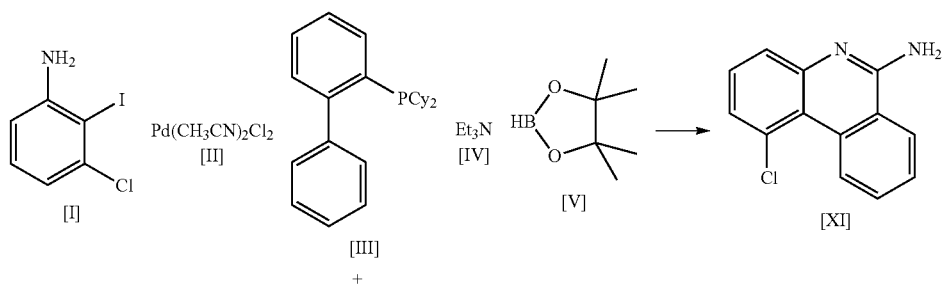

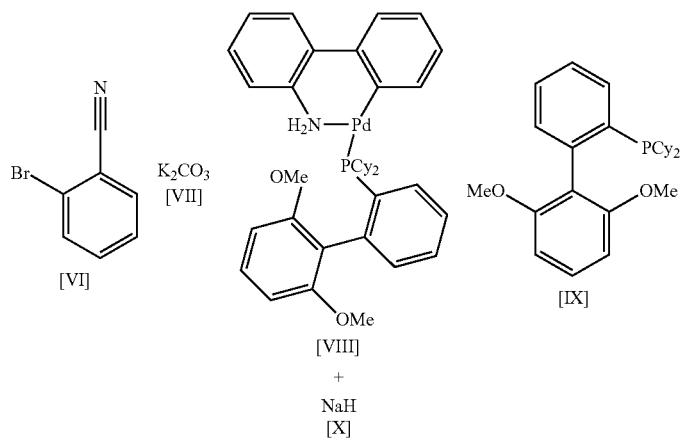

A mixture of 3-chloro-2-iodoaniline (8.77 g, 34.6 mmol), CyJohnPhos (0.462 g, 1.319 mmol), and Pd(CH₃CN)₂Cl₂ (0.171 g, 0.659 mmol) was dissolved in dioxane (80 ml). Triethylamine (13.78 ml, 99 mmol) and 4,4,5,5-tetramethyl-1,3,2-dioxaborolane (10.04 ml, 69.2 mmol) were added to the solution in sequence via syringe. The reaction was refluxed for 4 h. The reaction was cooled to R.T. and a solid mixture of 2-bromobenzonitrile (6 g, 33 mmol), S-Phos Pd G2 (0.475 g, 0.659 mmol), S-Phos (0.271 g, 0.659 mmol), and potassium carbonate (9.11 g, 65.9 mmol) was added to the reaction mixture directly followed by the addition of dioxane (20 ml) and water (20 ml) and the reaction was heated to 85° C. overnight. Dioxane was removed and the crude product was extracted with dichloromethane (DCM). The organic part was evaporated to provide an oily product. The product was dissolved in THF (80 mL), and sodium hydride (1.978 g, 49.4 mmol) was directly added at 0° C. and stirred for 20 min. The reaction was quenched with brine (~150 mL). The THF was evaporated and the crude product was extracted with DCM and brine. Solid was collected by trituration in diethyl ether and hexane (52% yield).

-continued

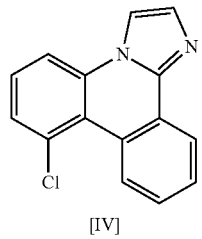

1-chlorophenanthridin-6-amine (3.93 g, 17.19 mmol), 2-chloroacetaldehyde (4.68 mL, 34.4 mmol), and sodium bicarbonate (2.89 g, 34.4 mmol) were combined and refluxed for 2 h. The reaction mixture was extracted with 10% MeOH in DCM and brine. The crude product was purified by column chromatography on silica (DCM/MeOH=9/1). The product was washed with diethyl ether and hexane to afford 8-chloroimidazo[1,2-f]phenanthridine (78%).

Synthesis of Ligand of Comparative Example 5

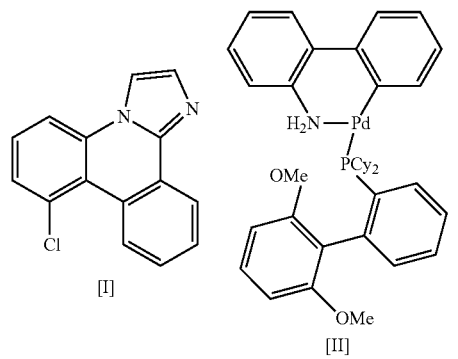

[I]

[II]

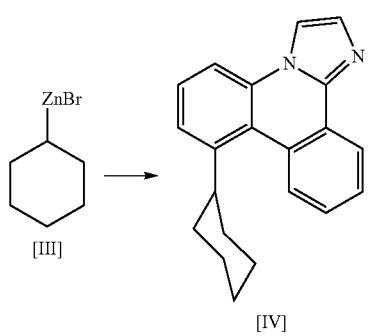

[III] → [IV]

A mixture of 8-chloroimidazo[1,2-f]phenanthridine (900 mg, 3.56 mmol) and SPhos Pd G2 (128 mg, 0.178 mmol) was vacuumed and back-filled with nitrogen several times. THF (40 ml) and cyclohexylzinc(II) bromide (14.25 ml, 7.12 mmol) were added via an addition funnel and stirred at R.T. overnight. The reaction was quenched with water and extracted with DCM. Crude product was chromatographed on silica (EA) to afford 8-cyclohexylimidazo[1,2-f]phenanthridine (80% yield).

Synthesis of Comparative Example 5

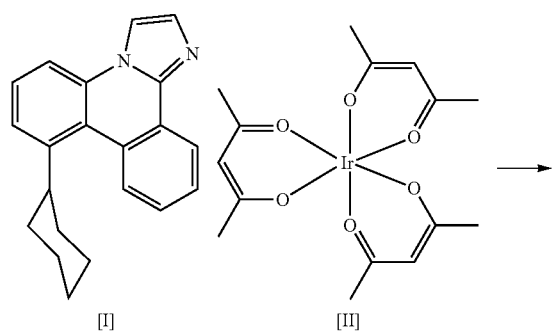

[I]  [II]

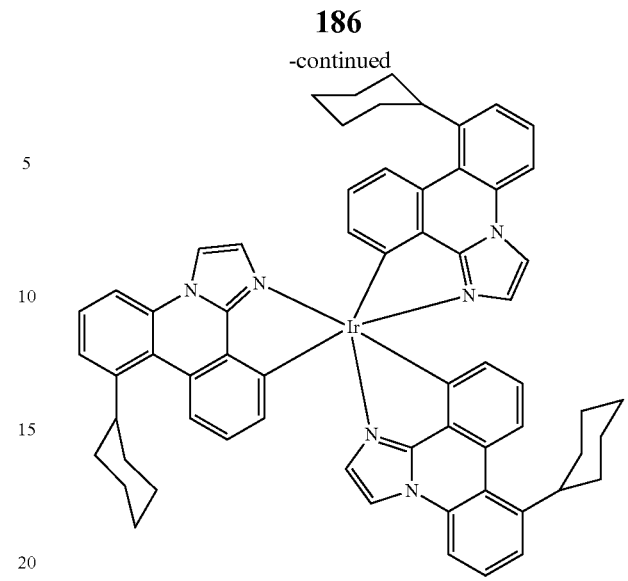

Comparative Example 5
[III]

8-cyclohexylimidazo[1,2-f]phenanthridine (180 mg, 5.99 mmol), Ir(acac)$_3$ (58.7 mg, 120 mmol), and tridecane (0.8 mL) were combined in an acid digestion bomb in glove box and heated at 245° C. in a sand bath overnight. The product was purified by column chromatography on silica column (DCM) (60% yield).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A compound comprising a ligand L selected from the group A consisting of:

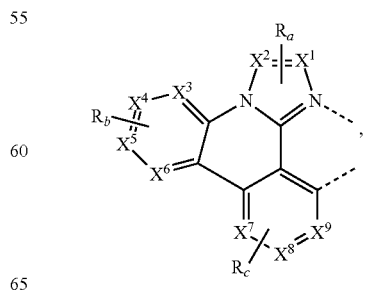

wherein $X^7$ is $Z^2$; and

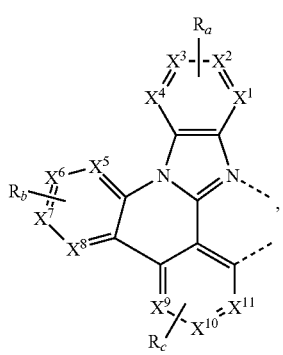

wherein X⁹ is Z²;

wherein each $X^1$, $X^3$, $X^4$, and $X^5$ are carbon, and $X^2$, and $X^6$ to $X^{11}$ are independently selected from carbon or nitrogen;

wherein each $R_a$, $R_b$, and $R_c$ may represent from mono substitution to the possible maximum number of substitution, or no substitution;

wherein each $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein when $R_a$, $R_b$, and $R_c$ represent at least di substitution, each of the two adjacent $R_a$, two adjacent $R_b$, and two adjacent $R_c$ are optionally fused or joined to form a ring;

wherein the ligand L is coordinated to a metal M selected from the group consisting of Ir, Rh, Re, Ru, Os, Pt, Au, and Cu;

wherein the ligand L is optionally linked to provide a tridentate, or tetradentate-ligand;

wherein the compound comprises at least one intramolecular hydrogen bonding interaction as shown

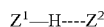

wherein $Z^1$ is carbon of alkyl, and $Z^2$ is nitrogen
and
the proton NMR chemical shift of H is shifted downfield by at least 1.3 ppm compared to the compound when $Z^2$ is carbon.

2. The compound of claim 1, wherein the compound has an emission with the first peak wavelength at the high energy end smaller at room temperature than that at 77K.

3. The compound of claim 1, wherein M is Ir or Pt.

4. The compound of claim 1, wherein the compound has a formula of $Ir(L)_n(L')_{3-n}$;
wherein L' is selected from group A; and
wherein n is 1, 2, or 3.

5. The compound of claim 1, wherein the compound has a formula of $Pt(L)_m(L')_{2-m}$;
wherein L' is selected from group A; and
wherein m is 1 or 2.

6. The compound of claim 1, wherein the ligand L is selected from the group consisting of:

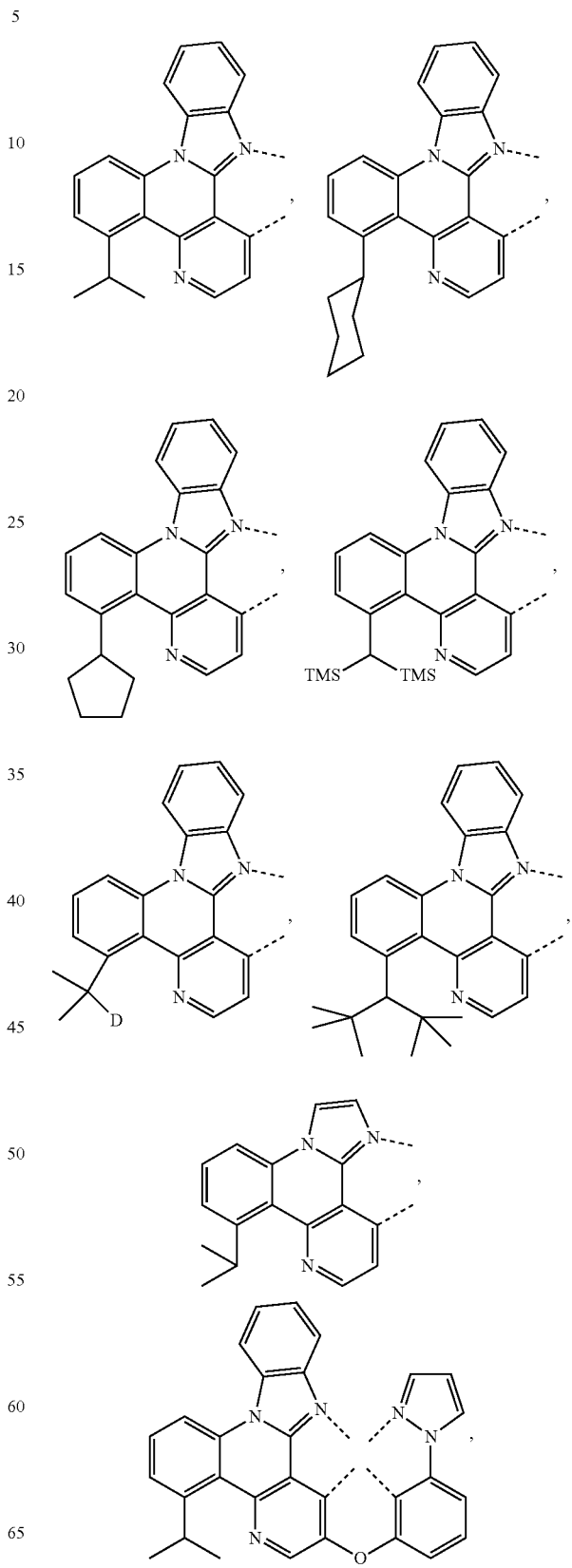

189
-continued
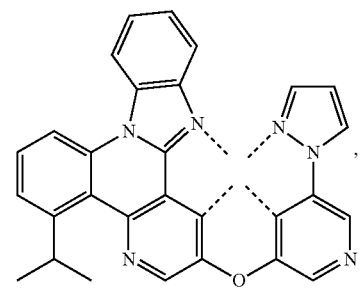
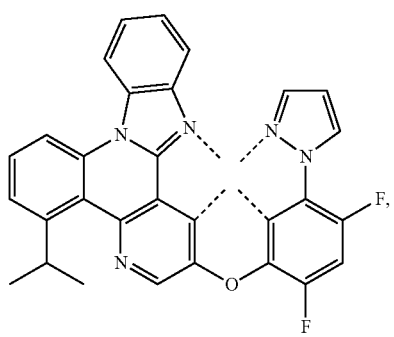
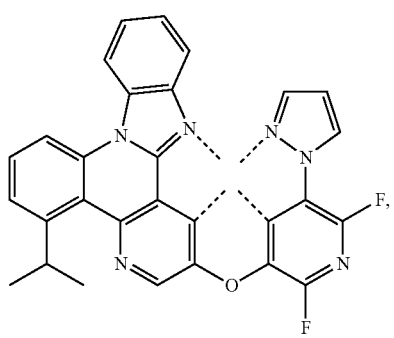
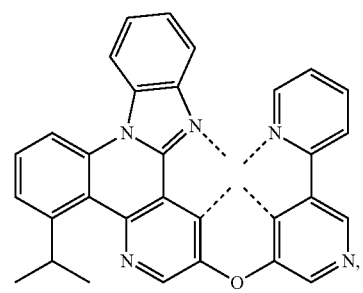
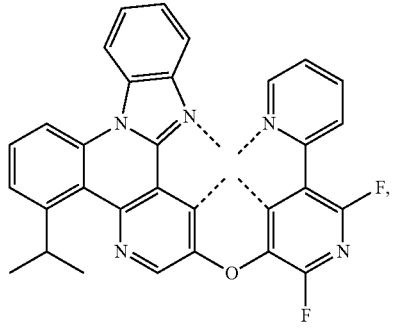
190
-continued
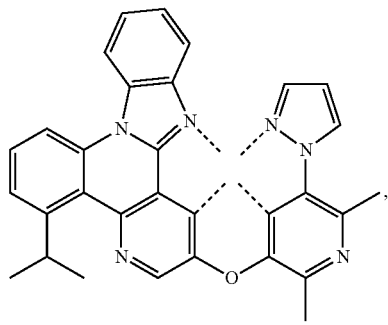
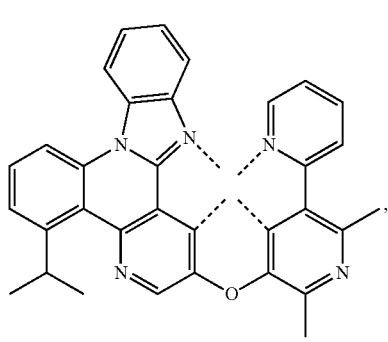
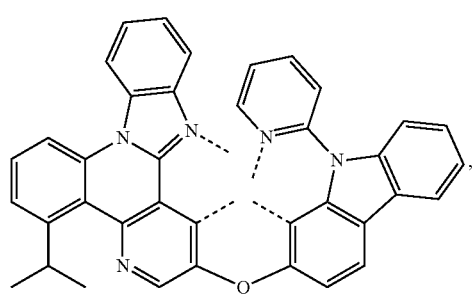
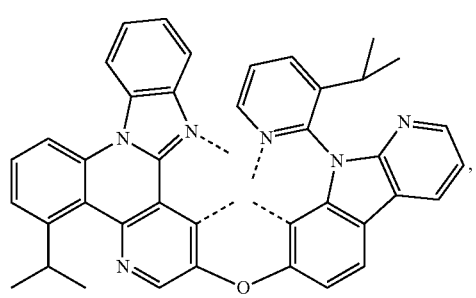
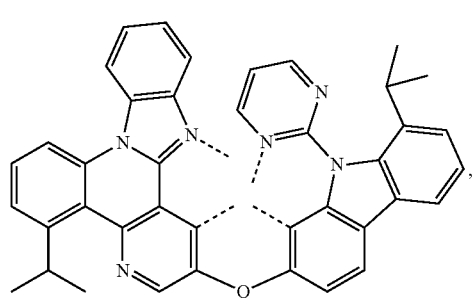

191
-continued
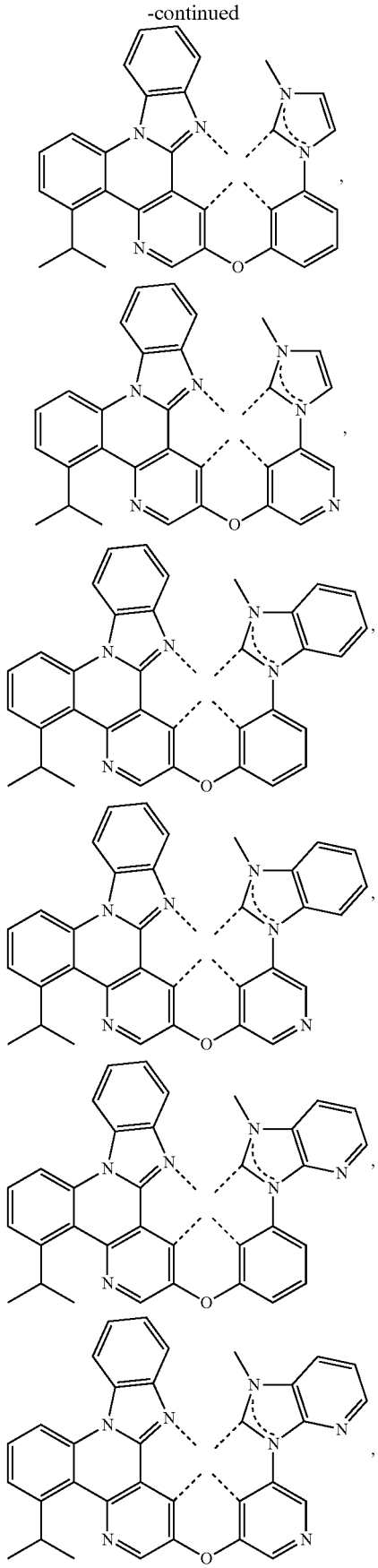
192
-continued
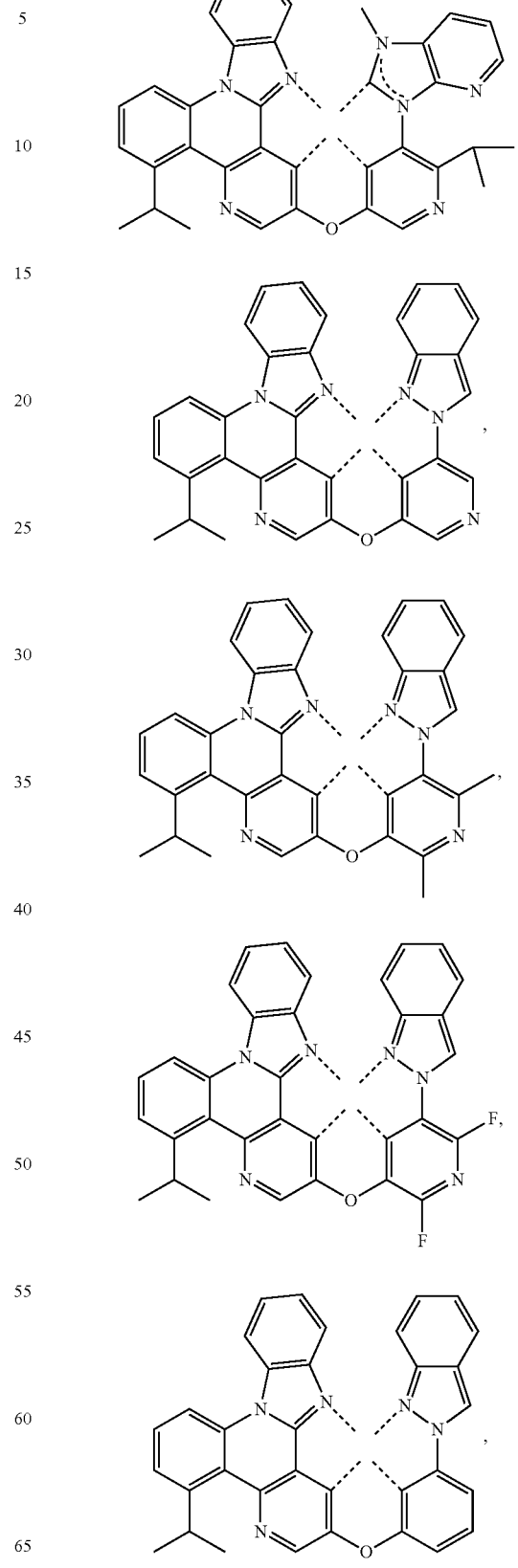

193
-continued
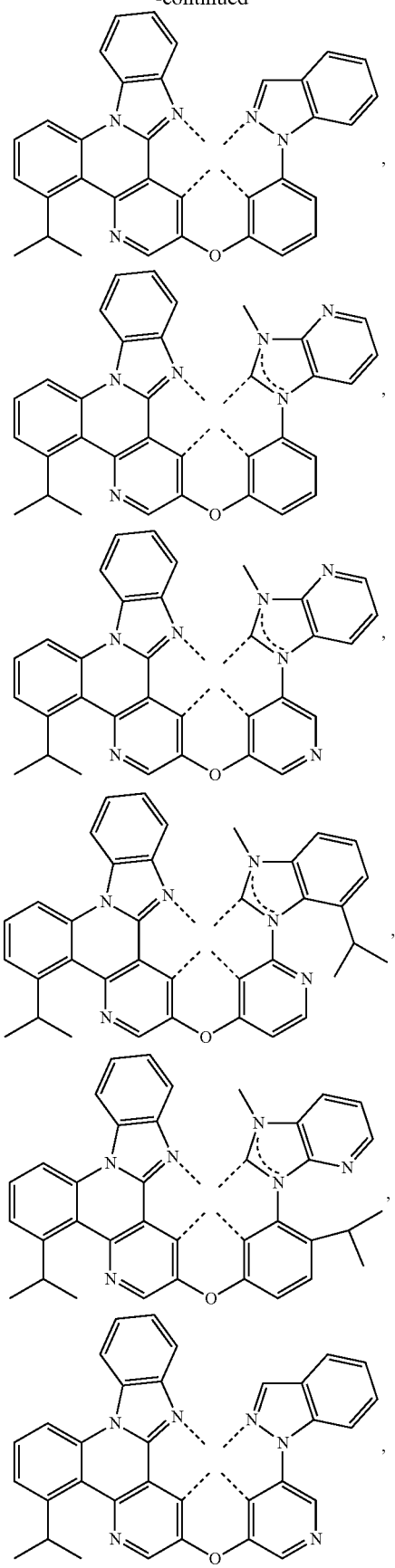
194
-continued
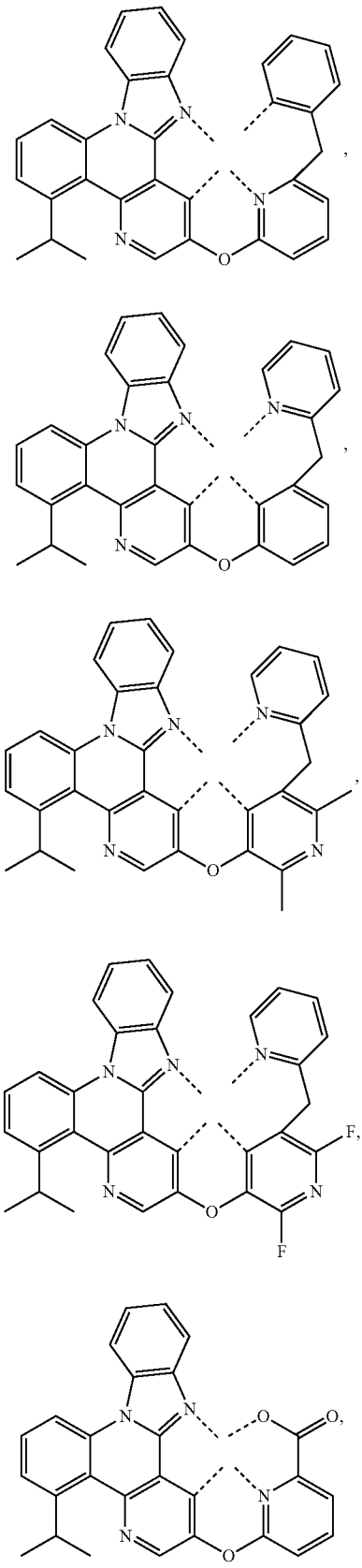

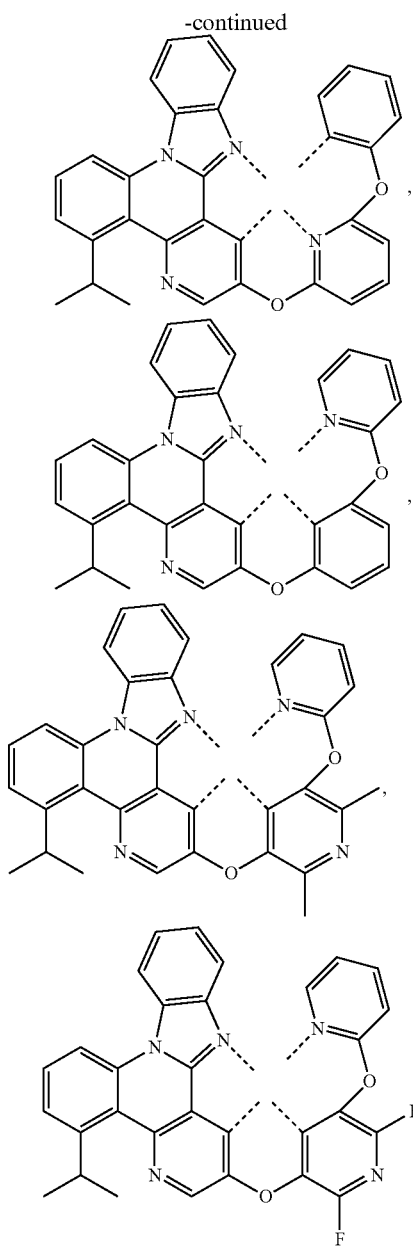
7. The compound of claim 1, wherein the compound is selected from the group consisting of:
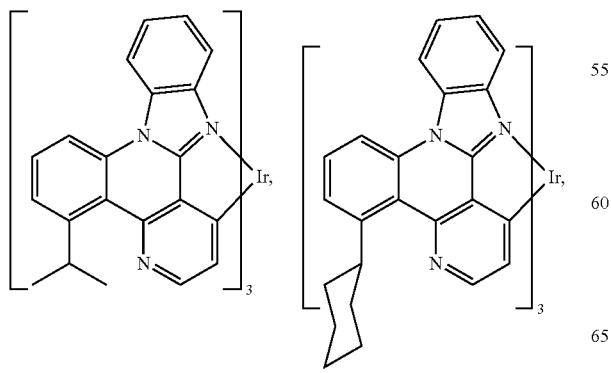
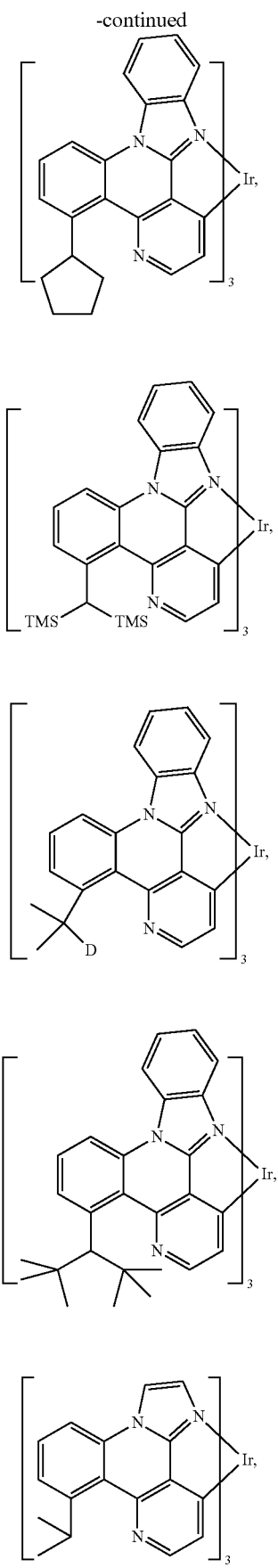

197
-continued
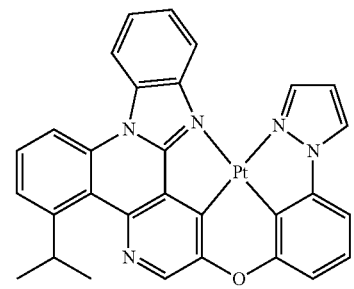
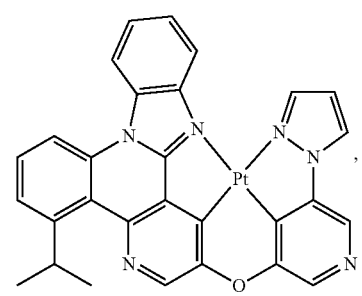
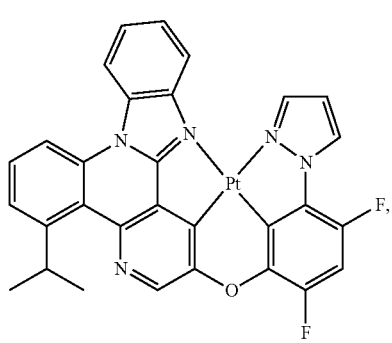
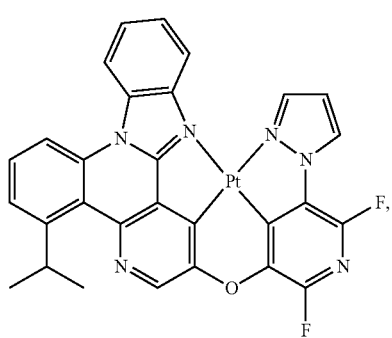
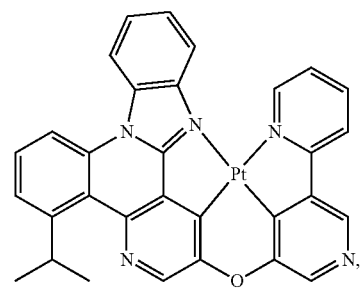
198
-continued
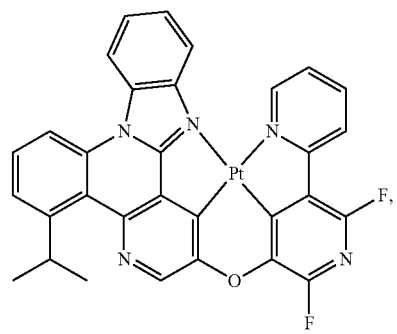
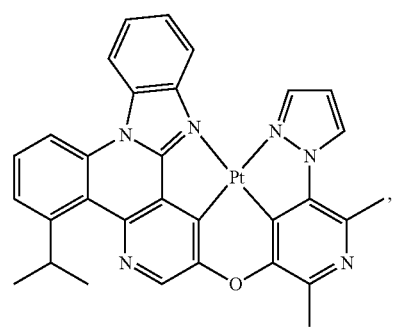
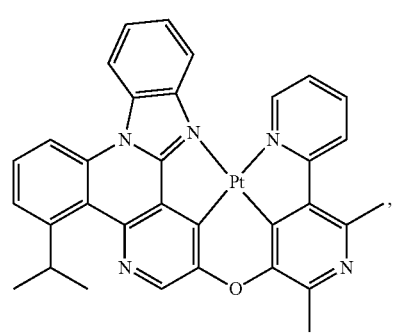
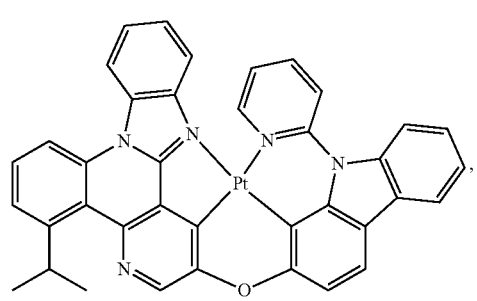
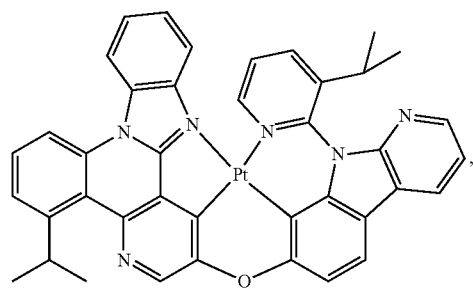

199
-continued
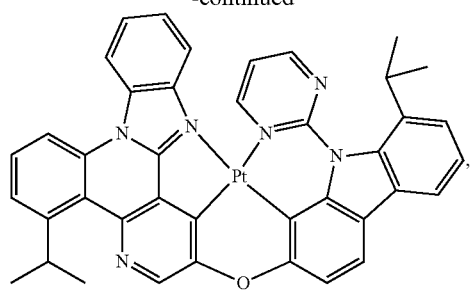
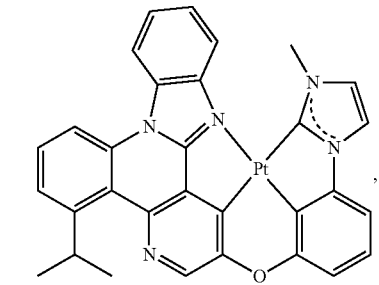
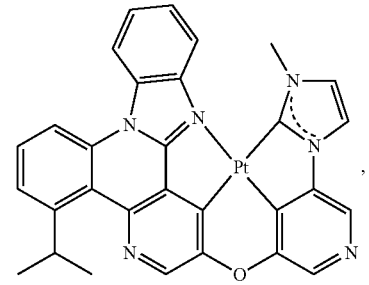
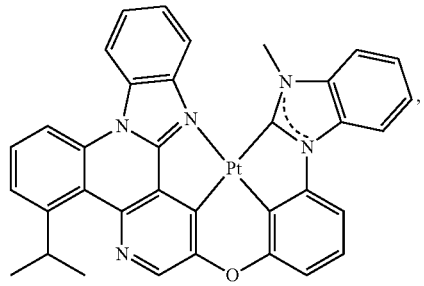
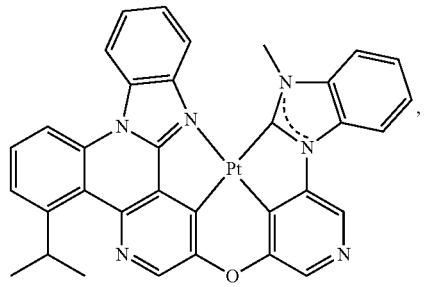
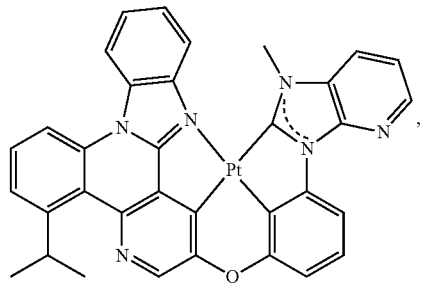
200
-continued
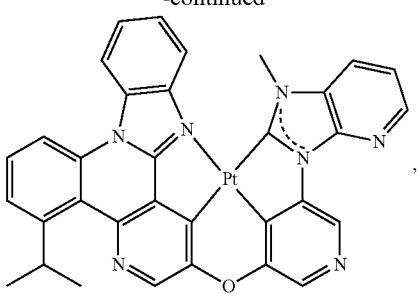
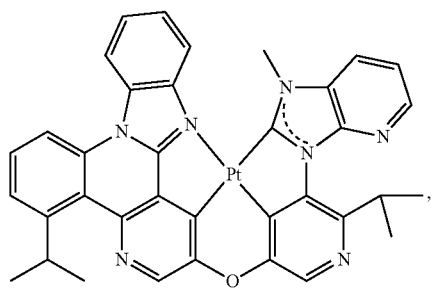
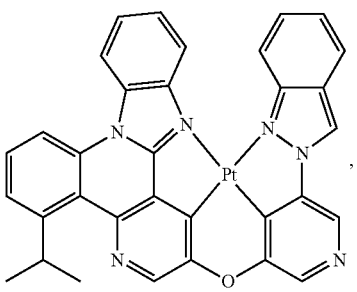
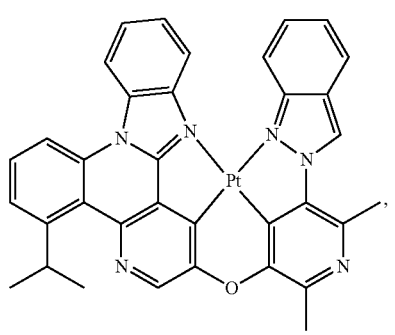
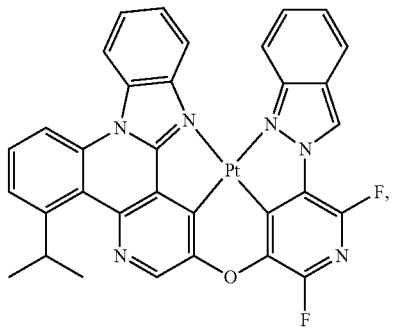

201
-continued
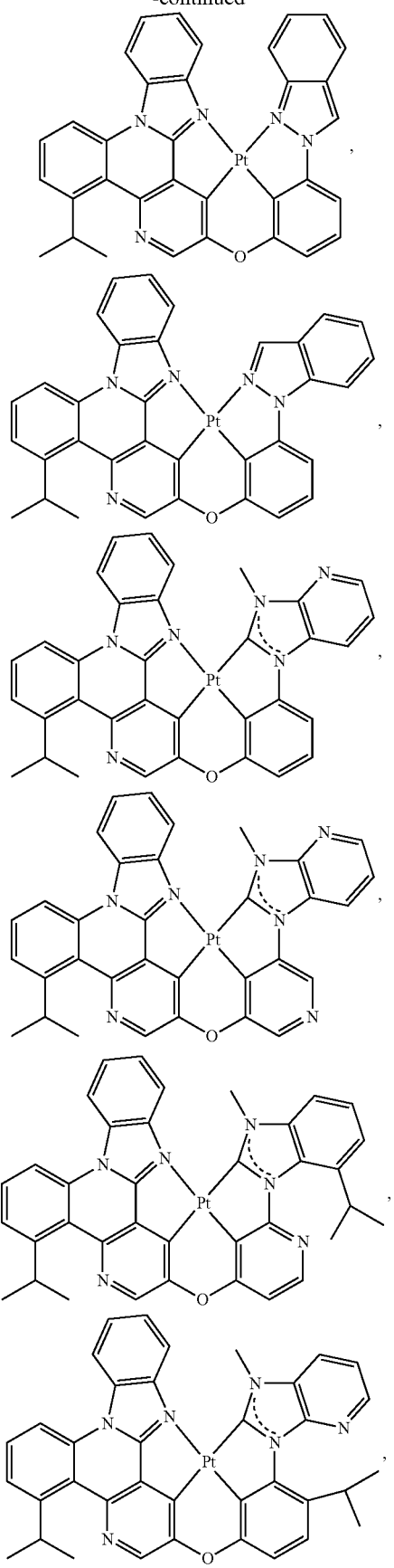
202
-continued
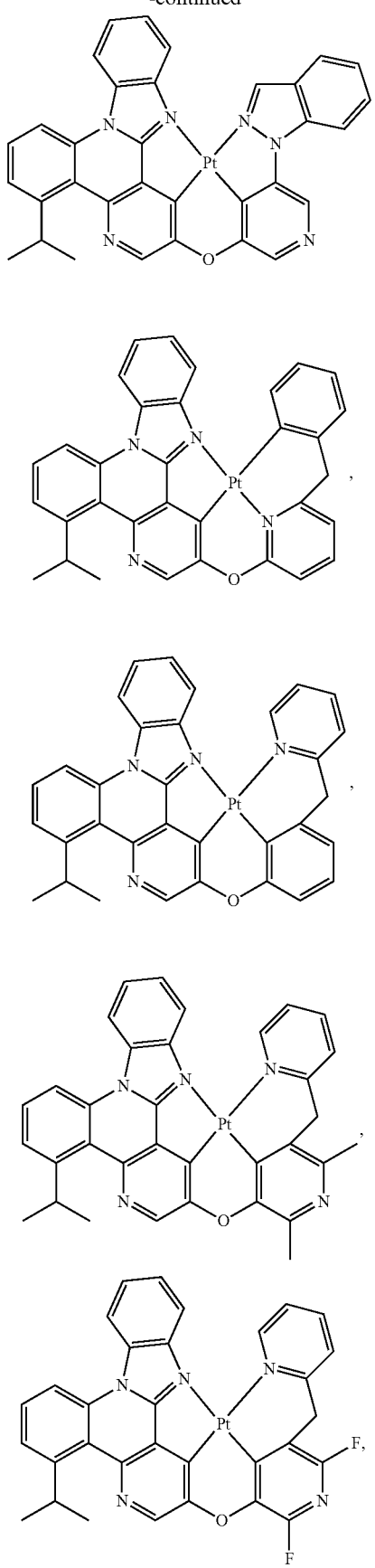

203
-continued
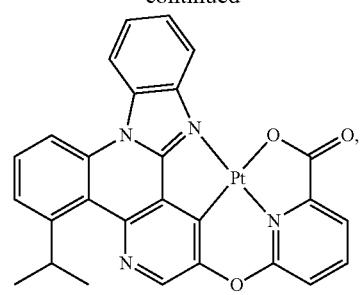
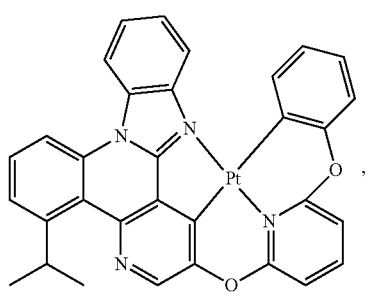
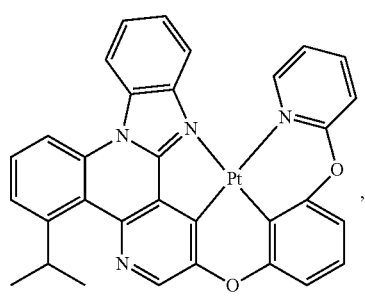
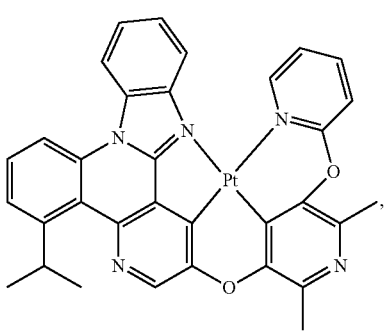
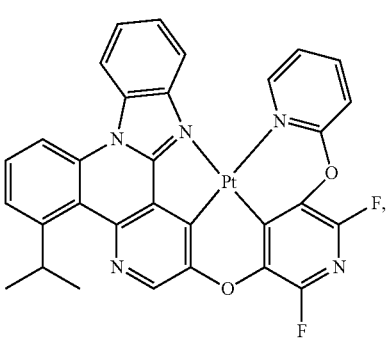
204
-continued
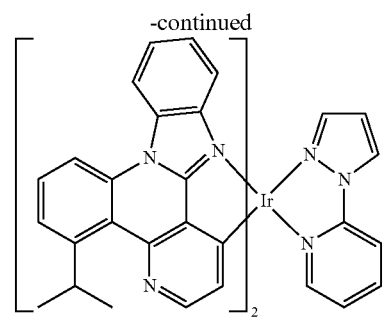
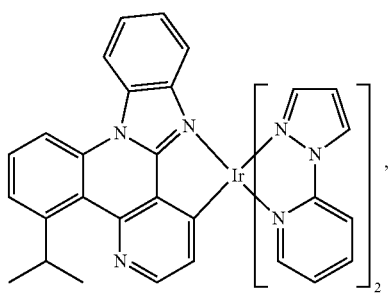
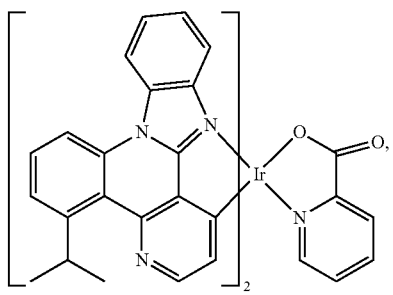
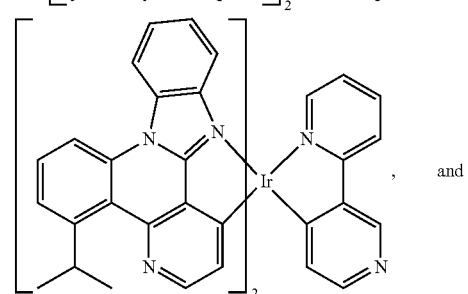, and
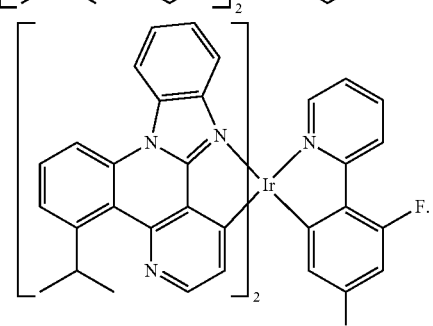
8. A first device comprising a first organic light emitting device, the first organic light emitting device comprising:
   an anode;
   a cathode; and
   an organic layer, disposed between the anode and the cathode, comprising a compound comprising a ligand L of claim 1.

9. The first device of claim 8, wherein the first device is selected from the group consisting of a consumer product, an electronic component module, an organic light-emitting device, and a lighting panel.

10. The first device of claim 8, wherein the organic layer is an emissive layer and the compound is an emissive dopant or a non-emissive dopant.

11. The first device of claim 8, wherein the organic layer further comprises a host; wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1$-$Ar_2$, $C_nH_{2n}$—$Ar_1$, or no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

12. The first device of claim 8, wherein the organic layer further comprises a host, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

13. The first device of claim 8, wherein the organic layer further comprises a host and the host is selected from the group consisting of:

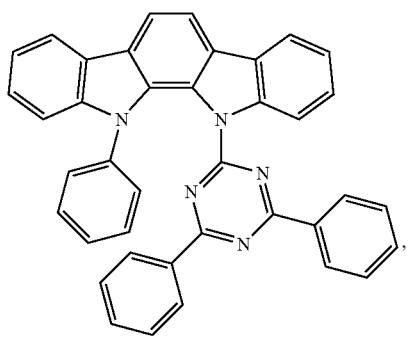

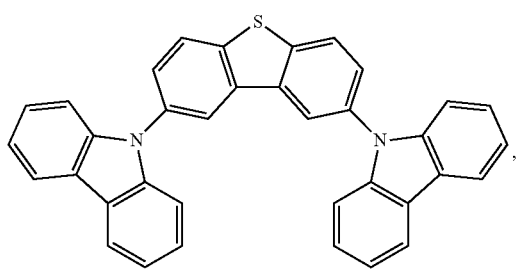

-continued

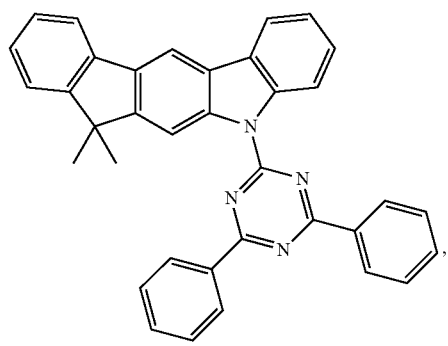

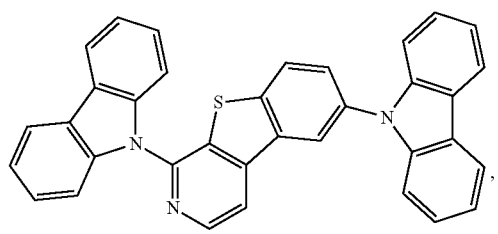

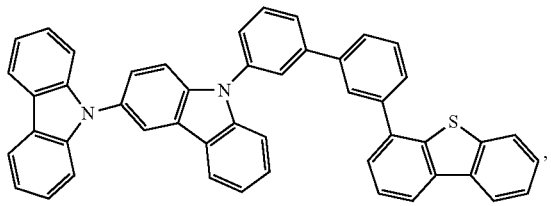

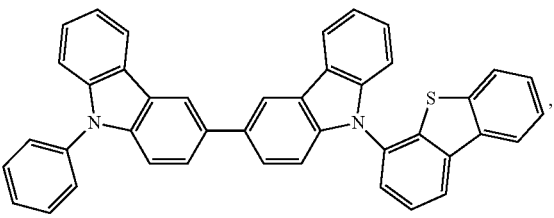

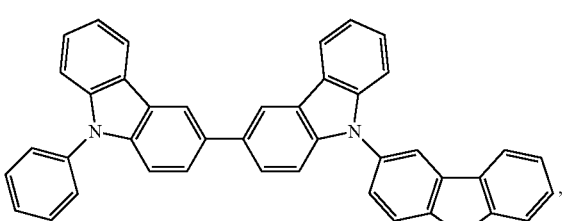

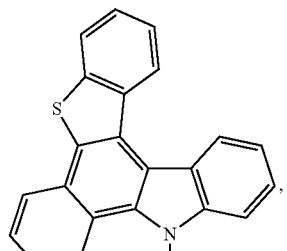

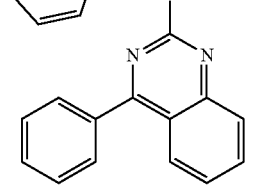

207
-continued
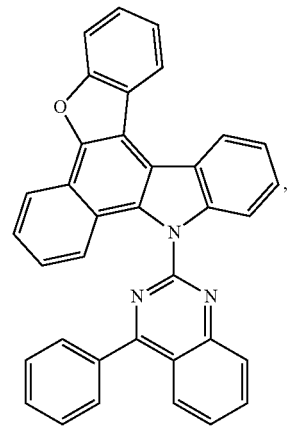
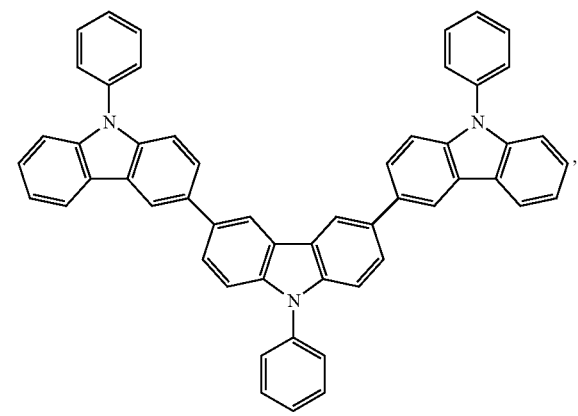
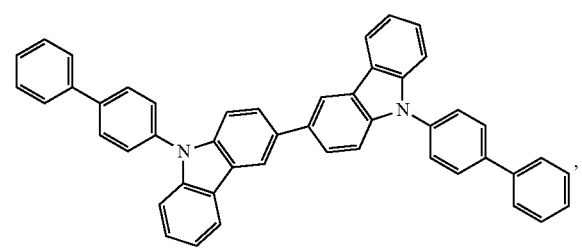
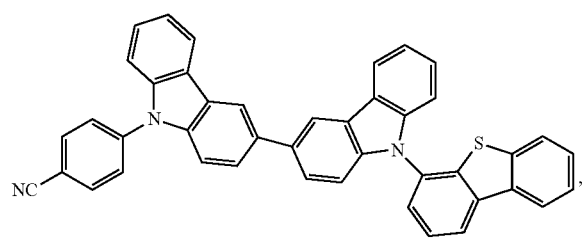
208
-continued
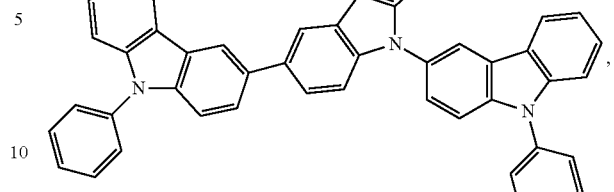
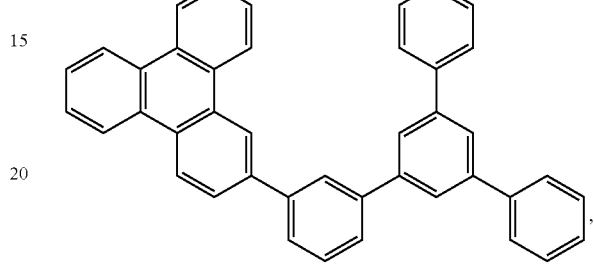
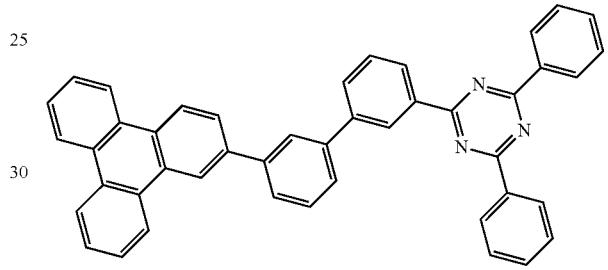
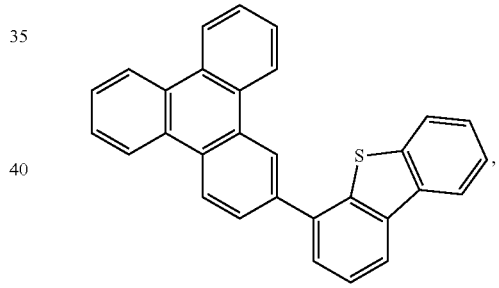
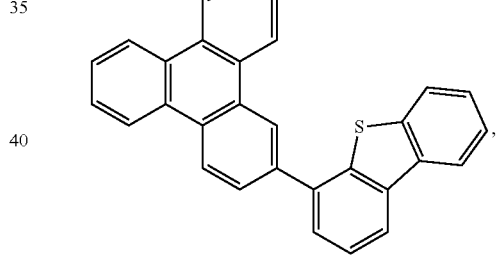
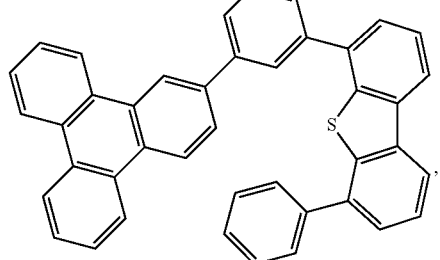

-continued

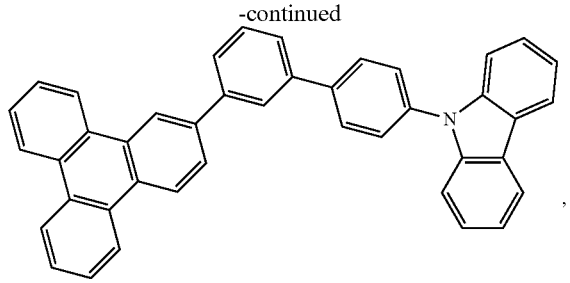

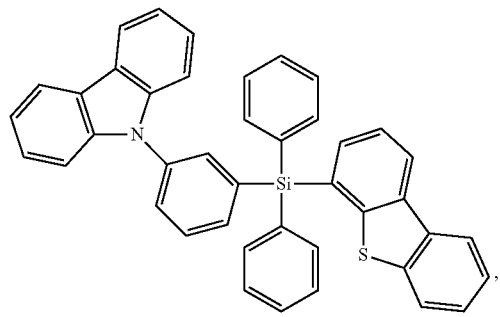

-continued

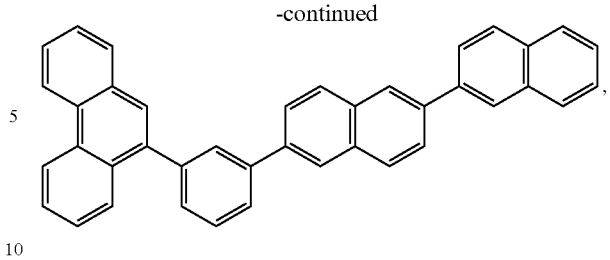

and combinations thereof.

14. The compound of claim 1, wherein $X^5$, $X^6$, and $X^8$ are carbon, and are each substituted with $R_b$, wherein $R_b$ is selected from the group consisting of alkyl, cycloalkyl, heteroalkyl, arylalkyl, alkoxy, aryloxy, amino, silyl, alkenyl, cycloalkenyl, aryl, and heteroaryl.

15. The compound of claim 14, wherein $X^6$ and $X^9$ are $Z^2$.

16. The compound of claim 1, wherein $X^6$, $X^7$, and $X^9$ are carbon, and are each substituted with $R_c$, wherein $R_c$ is selected from the group consisting of alkyl, cycloalkyl, heteroalkyl, arylalkyl, alkoxy, aryloxy, amino, silyl, alkenyl, cycloalkenyl, aryl, and heteroaryl.

17. The compound of claim 16, wherein $X^5$ and $X^8$ are $Z^2$.

* * * * *